United States Patent
May et al.

(10) Patent No.: US 9,677,119 B2
(45) Date of Patent: *Jun. 13, 2017

(54) MULTI-PRIMER AMPLIFICATION METHOD FOR TAGGING OF TARGET NUCLEIC ACIDS

(71) Applicant: Fluidigm Corporation, South San Francisco, CA (US)

(72) Inventors: Andrew May, San Francisco, CA (US); Peilin Chen, Richmond, CA (US); Jun Wang, Palo Alto, CA (US); Fiona Kaper, Solano Beach, CA (US); Megan Anderson, Washington, DC (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/180,262

(22) Filed: Feb. 13, 2014

(65) Prior Publication Data

US 2014/0272952 A1 Sep. 18, 2014

Related U.S. Application Data

(62) Division of application No. 12/753,703, filed on Apr. 2, 2010, now Pat. No. 8,691,509.

(Continued)

(51) Int. Cl.
*C12Q 1/68* (2006.01)
*C07H 21/02* (2006.01)
(Continued)

(52) U.S. Cl.
CPC ...... *C12Q 1/6806* (2013.01); *B01L 3/502738* (2013.01); *C12Q 1/686* (2013.01);
(Continued)

(58) Field of Classification Search
CPC ........ C12Q 2525/155; C12Q 2525/161; C12Q 2527/143; C12Q 2535/122;
(Continued)

(56) References Cited

U.S. PATENT DOCUMENTS 4,683,202 A   7/1987   Mullis
5,066,584 A   11/1991  Gyllensten et al.
(Continued)

FOREIGN PATENT DOCUMENTS

CN    101067156 A    11/2007
EP     0197196 A1    10/1986
(Continued)

OTHER PUBLICATIONS

U.S. Appl. No. 61/605,016, filed Feb. 29, 2012, Fowler et al.
(Continued)

*Primary Examiner* — Teresa Strzelecka
(74) *Attorney, Agent, or Firm* — Emily M. Haliday; Weaver Austin Villeneuve & Sampson LLP

(57) ABSTRACT

In certain embodiments, the present invention provides amplification methods in which nucleotide tag(s) and, optionally, a barcode nucleotide sequence are added to target nucleotide sequences. In other embodiments, the present invention provides a microfluidic device that includes a plurality of first input lines and a plurality of second input lines. The microfluidic device also includes a plurality of sets of first chambers and a plurality of sets of second chambers. Each set of first chambers is in fluid communication with one of the plurality of first input lines. Each set of second chambers is in fluid communication with one of the plurality of second input lines. The microfluidic device further includes a plurality of first pump elements in fluid communication with a first portion of the plurality of second input lines and a plurality of second pump elements in fluid (Continued)

communication with a second portion of the plurality of second input lines.

16 Claims, 26 Drawing Sheets

Related U.S. Application Data

(60) Provisional application No. 61/166,181, filed on Apr. 2, 2009, provisional application No. 61/166,105, filed on Apr. 2, 2009, provisional application No. 61/186,327, filed on Jun. 11, 2009, provisional application No. 61/305,907, filed on Feb. 18, 2010.

(51) Int. Cl.
    *B01L 3/00* (2006.01)
    *B01L 7/00* (2006.01)

(52) U.S. Cl.
    CPC .............. *B01L 3/50273* (2013.01); *B01L 7/52* (2013.01); *B01L 2300/087* (2013.01); *B01L 2300/0816* (2013.01); *B01L 2300/0864* (2013.01); *B01L 2300/0867* (2013.01); *B01L 2400/0487* (2013.01); *B01L 2400/0655* (2013.01)

(58) Field of Classification Search
    CPC ........ C12Q 2549/119; C12Q 2563/179; C12Q 2565/629; C12Q 1/6806; C12Q 1/686; B01L 2300/0864; B01L 2300/087; B01L 2400/0487; B01L 2400/0655
    See application file for complete search history.

(56) References Cited

U.S. PATENT DOCUMENTS

| | | | |
|---|---|---|---|
| 6,605,451 B1 | 8/2003 | Marmaro et al. |
| 6,824,981 B2 | 11/2004 | Chait et al. |
| 7,097,980 B2 | 8/2006 | Barany et al. |
| 7,153,658 B2 | 12/2006 | Andersen et al. |
| 7,312,034 B2 | 12/2007 | Virgos et al. |
| 7,851,148 B2 | 12/2010 | Han |
| 8,318,434 B2 | 11/2012 | Cuppens |
| 8,450,063 B2 | 5/2013 | Dube et al. |
| 8,628,923 B2 | 1/2014 | Hamilton et al. |
| 8,691,509 B2 | 4/2014 | May et al. |
| 8,697,363 B2 | 4/2014 | Mir et al. |
| 9,074,204 B2 | 7/2015 | Anderson et al. |
| 2001/0046681 A1 | 11/2001 | Senapathy |
| 2002/0160361 A1 | 10/2002 | Loehrlein et al. |
| 2003/0119004 A1 | 6/2003 | Wenz et al. |
| 2004/0005594 A1 | 1/2004 | Holliger et al. |
| 2004/0081993 A1 | 4/2004 | Cantor et al. |
| 2004/0086892 A1 | 5/2004 | Crothers et al. |
| 2004/0091879 A1 | 5/2004 | Nolan et al. |
| 2004/0110153 A1 | 6/2004 | Dong et al. |
| 2004/0110191 A1 | 6/2004 | Winkler et al. |
| 2004/0209299 A1 | 10/2004 | Pinter et al. |
| 2004/0229349 A1 | 11/2004 | Daridon |
| 2005/0064488 A1 | 3/2005 | Huh et al. |
| 2005/0095634 A1 | 5/2005 | Baker et al. |
| 2005/0170373 A1 | 8/2005 | Monforte |
| 2005/0252773 A1 | 11/2005 | McBride et al. |
| 2005/0260640 A1 | 11/2005 | Andersen et al. |
| 2006/0040297 A1 | 2/2006 | Leamon et al. |
| 2006/0053503 A1 | 3/2006 | Culiat et al. |
| 2006/0105380 A1 | 5/2006 | Slepnev |
| 2007/0020640 A1 | 1/2007 | McCloskey et al. |
| 2007/0077570 A1 | 4/2007 | Lao et al. |
| 2007/0172873 A1 | 7/2007 | Brenner et al. |
| 2007/0219364 A1 | 9/2007 | Andersen et al. |
| 2007/0224613 A1 | 9/2007 | Strathmann |
| 2008/0108063 A1 | 5/2008 | Lucero et al. |
| 2008/0131937 A1 | 6/2008 | Schroeder |
| 2008/0223721 A1 | 9/2008 | Cohen et al. |
| 2009/0053719 A1 | 2/2009 | Lo et al. |
| 2009/0163366 A1 | 6/2009 | Nickerson et al. |
| 2009/0170713 A1 | 7/2009 | van Eijk et al. |
| 2009/0233802 A1 | 9/2009 | Bignell et al. |
| 2009/0239308 A1 | 9/2009 | Dube et al. |
| 2009/0317798 A1 | 12/2009 | Heid et al. |
| 2010/0069250 A1 | 3/2010 | White, III et al. |
| 2010/0120038 A1 | 5/2010 | Mir et al. |
| 2010/0143908 A1 | 6/2010 | Gillevet |
| 2010/0178655 A1 | 7/2010 | Hamilton et al. |
| 2010/0203538 A1 | 8/2010 | Dube et al. |
| 2010/0273219 A1 | 10/2010 | May et al. |
| 2010/0285537 A1 | 11/2010 | Zimmermann |
| 2011/0053806 A1 | 3/2011 | Amin |
| 2011/0129841 A1 | 6/2011 | Heid et al. |
| 2011/0143949 A1 | 6/2011 | Heid et al. |
| 2011/0207134 A1 | 8/2011 | Faham et al. |
| 2013/0005585 A1 | 1/2013 | Anderson et al. |
| 2013/0323732 A1 | 12/2013 | Anderson et al. |
| 2014/0087973 A1 | 3/2014 | Amin |
| 2014/0154679 A1 | 6/2014 | Dube et al. |
| 2014/0186827 A1 | 7/2014 | Jones et al. |
| 2014/0193812 A1 | 7/2014 | Hamilton et al. |
| 2014/0227691 A1 | 8/2014 | May et al. |
| 2014/0296090 A1 | 10/2014 | Mir et al. |
| 2016/0208322 A1 | 7/2016 | Anderson et al. |

FOREIGN PATENT DOCUMENTS

| | | |
|---|---|---|
| EP | 2201143 B1 | 11/2012 |
| WO | WO/01/59161 | 8/2001 |
| WO | WO02/081729 | 10/2002 |
| WO | WO2004/040001 | 5/2004 |
| WO | WO/2004/051218 | 6/2004 |
| WO | WO 2004/081183 | 9/2004 |
| WO | WO 2005/003394 | 1/2005 |
| WO | WO/2005/064020 | 7/2005 |
| WO | WO/2005/107938 | 11/2005 |
| WO | WO/2006/023919 | 3/2006 |
| WO | WO/2006/128010 | 11/2006 |
| WO | WO/2007/024798 | 3/2007 |
| WO | WO2007/033385 | 3/2007 |
| WO | WO/2007/044091 | 4/2007 |
| WO | WO 2007/104816 | 9/2007 |
| WO | WO 2008/015396 | 2/2008 |
| WO | WO/2010/027870 | 3/2010 |
| WO | WO/2010/115154 | 10/2010 |
| WO | WO/2011/142836 | 11/2011 |
| WO | WO/2011/143659 | 11/2011 |
| WO | WO/2012/162267 | 11/2012 |

OTHER PUBLICATIONS

U.S. Appl. No. 13/869,804, filed Apr. 24, 2013, Dube et al.
U.S. Appl. No. 13/977,622, filed Jun. 28, 2013, May et al.
U.S. Appl. No. 13/977,629, filed Jun. 28, 2013, Jones et al.
U.S. Appl. No. 14/029,676, filed Sep. 17, 2013, Amin.
U.S. Appl. No. 14/102,331, filed Dec. 10, 2013, Hamilton et al.
International Search Report and Written Opinion dated May 10, 2010 issued in PCT/US2009/055083.
International Preliminary Examination Report dated Mar. 10, 2011 issued in PCT/US2009/055083.
International Search Report and Written Opinion dated Aug. 30, 2010 issued in PCT/US2010/029854.
International Preliminary Examination Report dated Oct. 13, 2011 issued in PCT/US2010/029854.
International Search Report and Written Opinion dated Dec. 7, 2012 issued in PCT/US2012/038894.
CN Office Action dated Nov. 1, 2012 issued in CN200980142505.9.
CN Second Office Action dated Sep. 17, 2013 issued in CN200980142505.9.
CN Office Action dated Mar. 4, 2013 issued in CN201080021508.X.
CN Office Action dated Jan. 13, 2014 issued in CN201080021508.X.

(56) References Cited

OTHER PUBLICATIONS

EA Office Action dated Nov. 27, 2013 issued in EA201171206.
EP Extended Search Report dated Oct. 15, 2012 issued in EP09812052.0.
EP Extended Search Report dated Jul. 19, 2012 issued in EP10759511.8.
EP Office Action dated Mar. 15, 2013 issued in EP10759511.8.
Singapore Written Opinion dated Oct. 31, 2013 issued in SG201107142-0.
US Office Action dated May 3, 2012 issued in U.S. Appl. No. 12/548,132.
US Final Office Action dated Feb. 12, 2013 issued in U.S. Appl. No. 12/548,132.
US Notice of Allowance dated Nov. 18, 2013 issued in U.S. Appl. No. 12/548,132.
US Office Action dated Jun. 28, 2012 issued in U.S. Appl. No. 12/753,703.
US Final Office Action dated Mar. 25, 2013 issued in U.S. Appl. No. 12/753,703.
US Office Action dated Jul. 10, 2013 issued in U.S. Appl. No. 12/753,703.
US Notice of Allowance dated Nov. 14, 2013 issued in U.S. Appl. No. 12/753,703.
Binladen et al. (2007) "The use of coded PCR Primers enables High-Throughput Sequencing of multiple homolog amplification products by 454 parallel sequencing" *PLOS One* 2(e197): 1-9.
Brownie et al. (1997) "The elimination of primer-dimer accumulation in PCR" *Nucleic Acids Research* 25(16): 3235-3241.
Guo et al. (2003) "Methodology for using a universal primer to label amplified DNA segments for molecular analysis" *Biotechnology Letters* 25:2079-2083.
Hayden et al. (2008) "Multiplex-Ready PCR: A new method for multiplexed SSR and SNP genotyping" *BMC Genomics* 9(1): 80(1-12).
Kita-Matsuo et al. (2005) "Adaptor-tagged competitive polymerase chain reaction: amplification bias and quantified gene expression levels" *Analytical Biochemistry* 339(1): 15-28.
Makrigiorgos et al. (2002) "A PCR-based amplification method retaining the quantitative difference between two complex genomes" *Nature Biotechnology* 20: 936-39 (Published online: Aug. 5, 2002, doi:1 0.1 038/nbt724).
Neilan et al. (1997) "A universal procedure for primer labelling of amplicons" *Nucleic Acids Research* 25(14): 2938-2939.
Sawasaki et al. (2002) "A cell-free protein synthesis system for high-throughput proteomics" *PNAS* 99(23):14652-14657.
Sellner et al. (2004) "MLPA and MAPH: New Techniques for Detection of Gene Deletion" *Human Mutation* 23(5): 413-419.
Stiirzenbaum (1999) "Transfer RNA Reduces the Formation of Primer Artifacts During Quantitative PCR" *BioTechniques* 27:50-52.
Teo et al. (2002) "Reliable and reproducible LightCycler qPCR for HIV-1 DNA 2-LTR circles" *Journal of Immunological Methods* 270: 109-118.
Uematsu et al. (2001) "Multiplex polymerase chain reaction (PCR) with color-tagged module-shuffling primers for comparing gene expression levels in various cells" *Nucleic Acids Research, Oxford University Press, GB* 29(16): E84(1-6).
International Preliminary Report on Patentability dated Apr. 8, 2014 issued in PCT/US2012/038894.
AU Office Action dated May 23, 2014 issued in AU2010232439.
CN Third Office Action dated Apr. 9, 2014 issued in CN200980142505.9.
U.S. Appl. No. 14/184,499, filed Feb. 19, 2014, Mir et al.
CN Decision of Rejection dated Oct. 21, 2014 issued in CN200980142505.9.
EA Office Action dated Jul. 18, 2014 issued in EA201171206.
EP Extended Search Report dated Sep. 16, 2014 issued in EP14158911.9.
Japanese Office Action dated Aug. 25, 2014 issued in JP2012-503757.
US Office Action dated Feb. 28, 2014 issued in U.S. Appl. No. 13/476,911.
US Final Office Action dated Sep. 17, 2014 issued in U.S. Appl. No. 13/476,911.
Gill et al. (2008) "Nucleic Acid Isothermal Amplification Technologiesa Review" *Nucleosides, Nucleotides, and Nucleic Acids* 27:224-243.
Gillevet et al. (May 2010) "Quantitative Assessment of the Human Gut Microbiome using Multitag Pyrosequencing" *Chem Biodivers.*7 (5): 1065-1075; NIH Public Access, Author Manuscript doi:10. 1002/cbdv.200900322 [14 pages].
Kaper et al. (Apr. 19, 2010) "Parallel preparation of targeted resequencing libraries from 480 genomic regions using multiplex PCR on the Access Array system," *AACR 2010 Abstract & presentation*, 3 pages.
Life Technologies (Feb. 10, 2011) "Ion Torrent Amplicon Sequencing," 6 Pages.
Canadian Office Action dated Jul. 8, 2015 issued in CA 2,734,868.
U.S. Appl. No. 14/723,872, filed May 28, 2015, Anderson et al.
Chinese First Office Action dated Jun. 15, 2015 issued in CN201410139163.8.
Chinese First Office Action dated Mar. 2, 2015 issued in CN201410138786.3.
Chinese Office Action [English description & Chinese Office Action] dated May 6, 2015 issued in CN 201280033406.9.
Chinese Second Office Action dated Dec. 22, 2015 issued in CN201410138786.3.
European Extended Search Report dated May 20, 2015 issued in EP 12 789 957.3.
Israel Office Action [Notification of Technical Defects Prior to Allowance of Application] dated Feb. 11, 2015 issued in IL215462.
Israel Office Action dated Mar. 3, 2014 issued in IL215462 [translation only].
Japanese Final Rejection dated Jul. 17, 2015 issued in JP2012-503757.
US Notice of Allowance dated Mar. 6, 2015 issued in U.S. Appl. No. 13/476,911.
US Office Action dated Feb. 2, 2016 issued in U.S. Appl. No. 14/184,499.
Hayden et al. (Feb. 18, 2008) "Multiplex-Ready PCR: A new method for multiplexed SSR and SNP Genotyping," *BMC Genomics*, 9(80):22 pages.
Hoffman et al. (2007) "DNA bar coding and pyrosequencing to identify rare HIV drug resistance mutations," *Nucleic Acids Research*,35(13):e91, 8pp [Published online Jun. 18, 2007].
Parameswaran et al. (2007) "A pyrosequencing-tailored nucleotide barcode design unveils opportunities for large-scale sample multiplexing," *Nucleic Acids Research*, 35(19):e130, 31 pages. [Published online Oct. 11, 2007].
Windbichler et al. (2006) "Isolation of specific RNA-binding proteins using the streptomycin-binding RNA aptamer," *Nature Protocols*,1(2):638-641.
US Final Office Action dated Aug. 15, 2016 issued in U.S. Appl. No. 14/184,499.
Chinese Notification of Reexamination dated Jul. 28, 2016 issued in CN200980142505.9.
Canadian Office Action dated Feb. 26, 2016 issued in CA 2,757,560.
Chinese Second Office Action dated Apr. 22, 2016 issued in CN201410139163.8.
European Office Action dated May 6, 2016 issued in EP 14 158 911.9.
Japanese Final Rejection dated Mar. 18, 2016 issued in JP2012-503757.
Chinese Office Action [partial English Description] dated Mar. 24, 2016 issued in CN 201280033406.9.
Chao et al., (2008) "Microfluidic single-cell analysis of intracellular compounds," *J. R. Soc. Interface*, Suppl 2, 5:S139-S150.
Marcus et al., (2006) "Microfluidic single-cell mRNA isolation and analysis," and Supporting information for: Microfluidic single cell mRNA isolation and analysis, *Anal. Chem.*, 78(9):3084-3089 (14 pages).
Marcus,(2006) "Single Cell Gene Expression Analysis Using Microfluidics," dissertation, [available at http://thesis.library.

(56) References Cited

OTHER PUBLICATIONS caltech.edu/2755/, deposited Jul. 12, 2006]; also entitled "Single mammalian cell gene expression analysis using microfluidics," 179pp.
Ottesen et al., (2006) "Microfluidic Digital PCR Enables Multigene Analysis of Individual Environment Bacteria," *Science*, 314:1464-1467.
Rickert et al., (2004) "Multiplixed Real-Time PCR Using Univeral Reporters," *Clin. Chem.*, 50(9):1680-1683 (9 pages).
Warren, (2008) "Single-Cell Gene-Expression Analysis by Quantitative RT-PCT," dissertation, [available at http://thesis.library.caltech.edu/2996/, deposited Aug. 7, 2007], 225 pages.

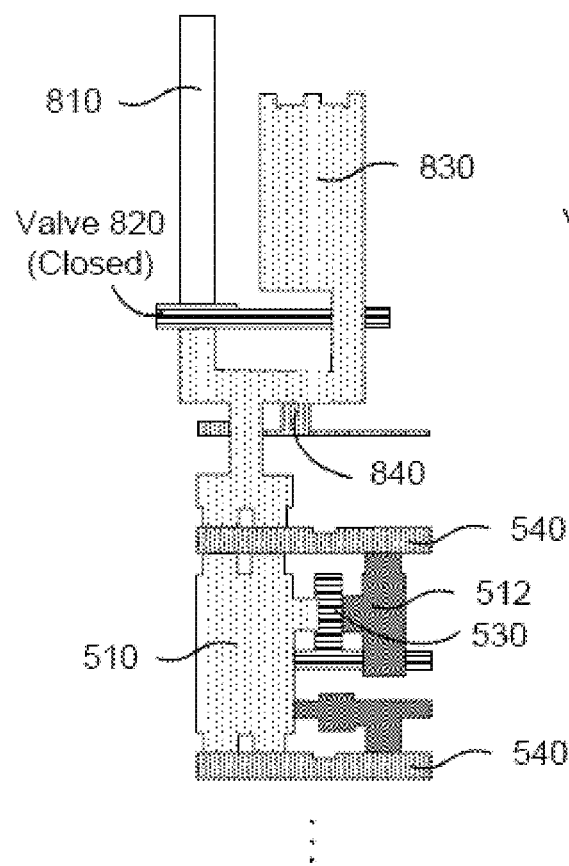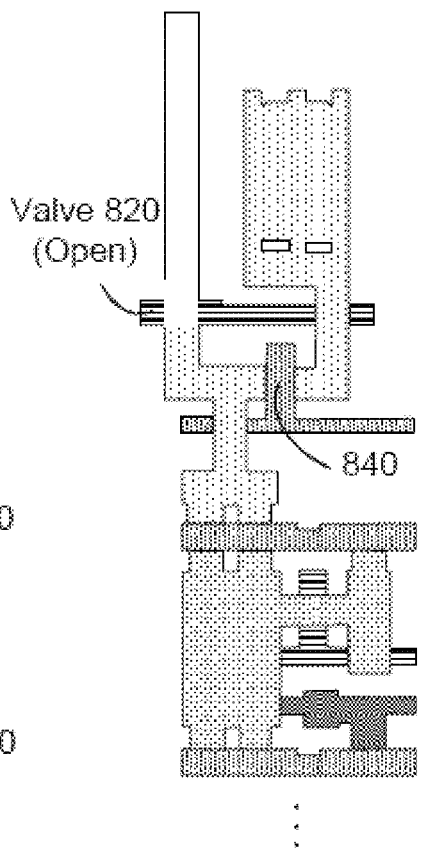
*Fig. 9A*                    *Fig. 9B*

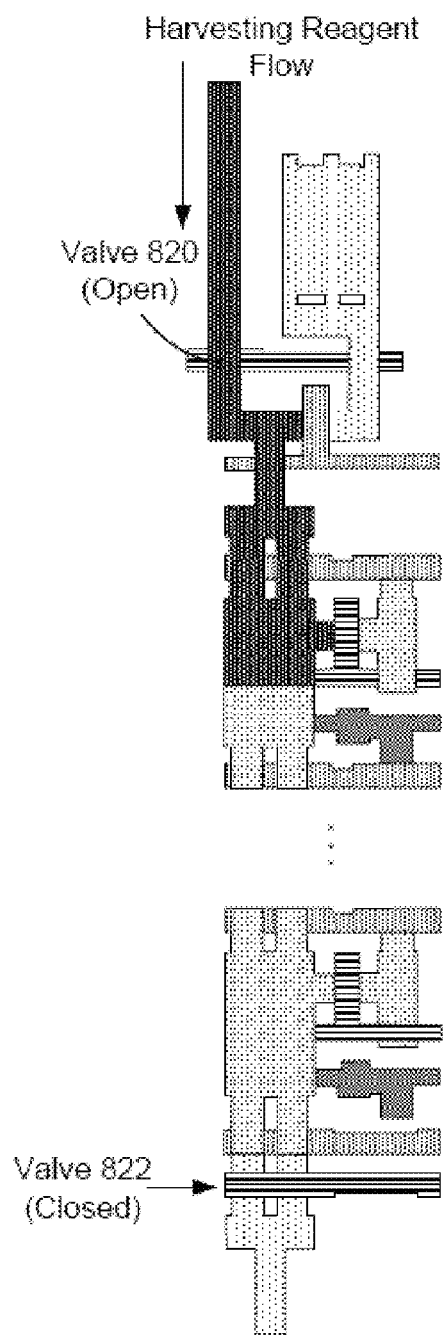
*Fig. 9C*     *Fig. 9D*

8A & 5B same amplicon
8B & 5A same amplicon

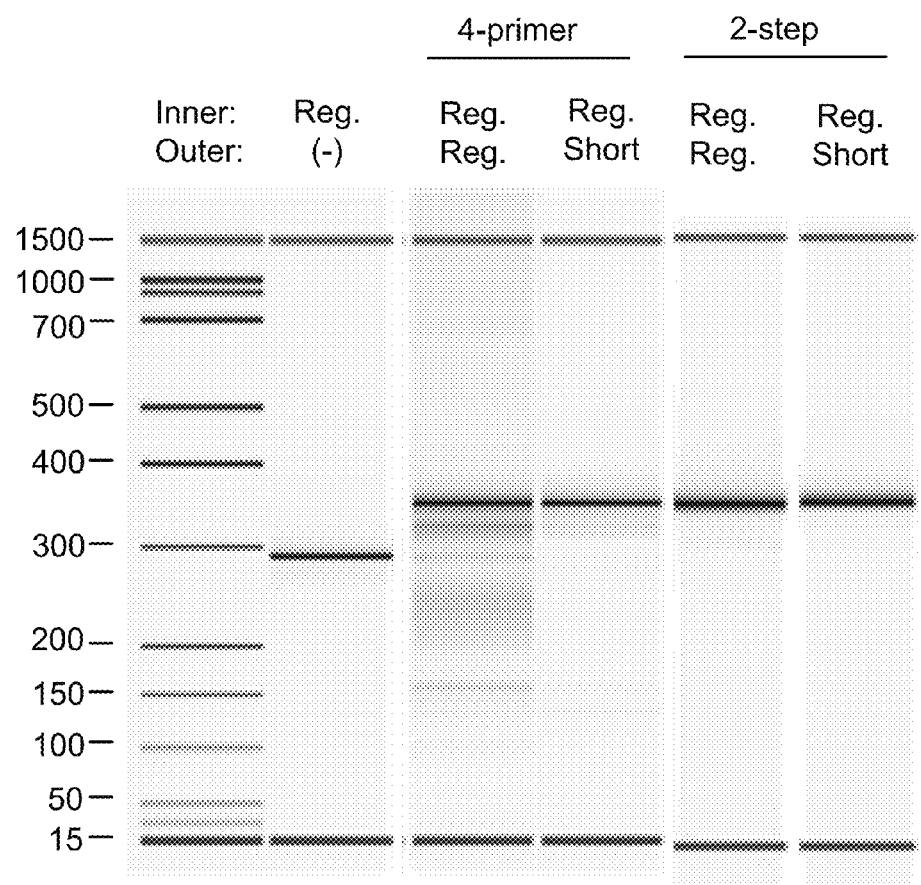
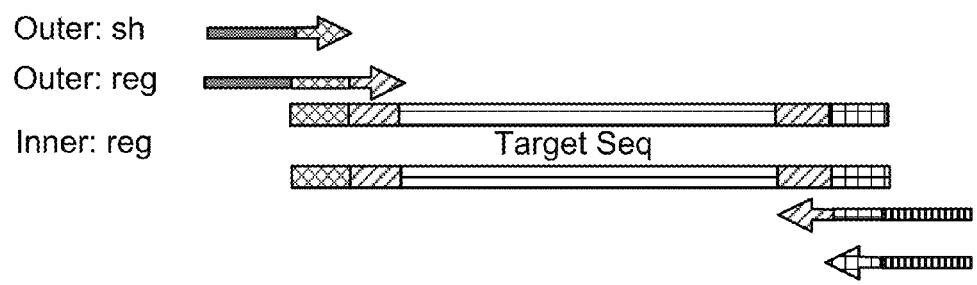
FIG. 17

MULTI-PRIMER AMPLIFICATION METHOD FOR TAGGING OF TARGET NUCLEIC ACIDS

CROSS-REFERENCE TO RELATED APPLICATIONS

This application is a division of U.S. application Ser. No. 12/753,703, filed Apr. 2, 2010, which claims the benefit of prior U.S. provisional application No. 61/166,181, filed Apr. 2, 2009; prior U.S. provisional application No. 61/166,105, filed Apr. 2, 2009; prior U.S. provisional application No. 61/186,327, filed Jun. 11, 2009; and prior U.S. provisional application No. 61/305,907, filed Feb. 18, 2010, which are all hereby incorporated by reference in their entireties.

FIELD OF THE INVENTION

The present invention relates generally to the area of high-throughput assays for detection and/or sequencing of particular target nucleic acids. In certain embodiments, the present invention provides amplification methods in which nucleotide tag(s) and a barcode nucleotide sequence are added to target nucleotide sequences.

BACKGROUND OF THE INVENTION

The ability to detect specific nucleic acid sequences in a sample has resulted in new approaches in diagnostic and predictive medicine, environmental, food and agricultural monitoring, molecular biology research, and many other fields. In addition, new sequencing methodologies provide the means for rapid high-throughput nucleic acid sequencing.

Additional methods, especially methods that facilitate analysis of many targets and/or the analysis of many samples simultaneously across a broad range of concentrations in a sample would be of great benefit.

Microfluidic devices can be used for analytical, preparative, metering, and other manipulative functions on a scale not imagined until recently. The advantages of microfluidic devices include conservation of precious reagents and samples, high density and throughput of sample analysis or synthesis, fluidic precision and accuracy at a level scarcely visible to the unaided eye, and a space reduction accompanying the replacement of counterpart equipment operating at the macrofluidic scale. Associated with the reduction in size and the increased density of microfluidic devices is increased complexity and higher engineering and fabrication costs associated with increasingly intricate device architecture.

Recently, there have been concerted efforts to develop and manufacture microfluidic systems to perform various chemical and biochemical analyses and syntheses. Additionally, microfluidic devices have the potential to be adapted for use with automated systems, thereby providing the additional benefits of further cost reductions and decreased operator errors because of the reduction in human involvement. Microfluidic devices have been proposed for use in a variety of applications, including, for instance, capillary electrophoresis, gas chromatography, and cell separations.

However, realization of these benefits has often been thwarted because of various complications associated with the microfluidic devices that have thus far been manufactured. For instance, many of the current microfluidic devices are manufactured from silica-based substrates, which are difficult and complicated to machine. As a result, many devices made from such materials are fragile. Furthermore, transport of fluid through many existing microfluidic devices requires regulation of complicated electrical fields to transport fluids in a controlled fashion through the device.

Thus, in view of the foregoing benefits that can be achieved with microfluidic devices but the current limitations of existing devices, there remains a need for microfluidic devices designed for use in conducting a variety of chemical and biochemical analyses. Because of its importance in modern biochemistry, there is a particular need for devices that can be utilized to conduct a variety of nucleic acid amplification reactions, while having sufficient versatility for use in other types of analyses as well.

Devices with the ability to conduct nucleic acid amplifications would have diverse utilities. For example, such devices could be used as an analytical tool to determine whether a particular target nucleic acid of interest is present or absent in a sample. Thus, the devices could be utilized to test for the presence of particular pathogens (e.g., viruses, bacteria, or fungi), and for identification purposes (e.g., paternity and forensic applications). Such devices could also be utilized to detect or characterize specific nucleic acids previously correlated with particular diseases or genetic disorders. When used as analytical tools, the devices could also be utilized to conduct genotyping analyses and gene expression analyses (e.g., differential gene expression studies). Alternatively, the devices can be used in a preparative fashion to amplify sufficient nucleic acid for further analysis such as sequencing of amplified product, cell-typing, DNA fingerprinting, and the like. Amplified products can also be used in various genetic engineering applications, such as insertion into a vector that can then be used to transform cells for the production of a desired protein product.

Despite these advances in microfluidic design and use, it would be useful to reduce the complexity of microfluidic chips and simplify their operation. Additionally, a need exists for an increased ability to recover reaction products from microfluidic devices. Thus, there is a need in the art for improved methods and systems related to microfluidic devices.

SUMMARY OF THE INVENTION

In certain embodiments, the invention provides a method for amplifying, tagging, and barcoding a plurality of target nucleic acids in a plurality of samples. The method entails preparing an amplification mixture for each target nucleic acid. Each amplification mixture includes:

a forward primer comprising a target-specific portion;

a reverse primer comprising a target-specific portion, wherein the forward primer additionally comprises a first nucleotide tag and/or the reverse primer additionally comprises a second nucleotide tag; and at least one barcode primer including a barcode nucleotide sequence and a first and/or second nucleotide tag-specific portion, wherein the barcode primer is in excess of the forward and/or reverse primer(s).

Each amplification mixture is subjected to amplification to produce a plurality of target amplicons, wherein each target amplicon includes a tagged target nucleotide sequence, with first and/or second nucleotide tags flanking the target nucleotide sequence, and at least one barcode nucleotide sequence at the 5' or 3' end of the target amplicon.

In specific embodiments, the forward primer additionally includes a first nucleotide tag. If desired, the reverse primer can additionally include a second nucleotide tag.

In certain embodiments of the tagging/barcoding method, the concentration of the barcode primer in the amplification mixtures is at least 4-fold the concentration of the forward and/or reverse primer(s). In variations of such embodiments, the concentration of the barcode primer in the amplification mixtures is at least 50-fold the concentration of the forward and/or reverse primer(s).

In particular embodiments of the barcoding/tagging method, the first and/or second nucleotide tags and/or the barcode nucleotide sequence are selected so as to avoid substantial annealing to the target nucleic acids. In illustrative embodiments, the barcode nucleotide sequence identifies a particular sample. Where the barcode primer includes a barcode nucleotide sequence and a first nucleotide tag-specific portion, in certain embodiments, a plurality of forward primers include the same first nucleotide tag. For, example, where multiple targets are to be amplified in different samples, the set of forward primers corresponding to the set of targets can all have the same first nucleotide tag.

In particular embodiments of the barcoding/tagging method, the forward and reverse primers for each target are initially combined separately from the sample, and each barcode primer is initially combined with its corresponding sample. For example, where T targets are to be amplified in S samples, T and S being integers greater than one, the method can additionally include preparing S×T amplification mixtures wherein the initially combined forward and reverse primers are added to the initially combined samples and barcode primers.

In certain embodiments of the barcoding/tagging method, the amplification is carried out for at least 3 cycles to introduce the first and second nucleotide tags and the barcode nucleotide sequence. In variations of these embodiments, the amplification is carried out for between 5 and 50 cycles. In particular embodiments, the amplification is carried out for a sufficient number of cycles to normalize target amplicon copy number across targets and across samples.

In certain embodiments of the barcoding/tagging method, at least 50 percent of the target amplicons produced upon amplification are present at greater than 50 percent of the average number of copies of target amplicons and less than 2-fold the average number of copies of target amplicons.

In other embodiments, the invention provides a method in which barcoding is, optionally, omitted and the target nucleotide sequences are tagged after amplification. This method entails amplifying a plurality of target nucleic acids, typically, in a plurality of samples. An amplification mixture is prepared for each target nucleic acid, wherein each amplification mixture includes:

a forward primer including a target-specific sequence; and
a reverse primer including a target-specific sequence;

Each amplification mixture is subjected to amplification to produce a plurality of target nucleotide sequences. The target nucleotide sequences are then tagged (e.g., by ligation of nucleotide tags unto one or both ends of the target nucleotide sequences) to produce a plurality of target amplicons. Each target amplicon includes first and/or second nucleotide tags flanking the target nucleotide sequence. In particular embodiments, at least 50 percent of the target amplicons are present at greater than 50 percent of the average number of copies of target amplicons and less than 2-fold the average number of copies of target amplicons.

In certain embodiments of the amplification methods described herein, at least 70 percent of the target amplicons are present at greater than 50 percent of the average number of copies of target amplicons and less than 2-fold the average number of copies of target amplicons. In illustrative embodiments, at least 90 percent of the target amplicons are present at greater than 50 percent of the average number of copies of target amplicons and less than 2-fold the average number of copies of target amplicons.

In various embodiments, the average length of the target amplicons is at least 25 bases, 50 bases, 100 bases, 200 bases, 500 bases, and 750 bases. Longer average lengths, such as 1 kilobase or more are also possible, as, for example, when amplification is carried out by long-range PCR. In such embodiments, amplification may yield target amplicons wherein at least 70 percent of the target amplicons are present at greater than 50 percent of the average number of copies of target amplicons and less than 2-fold the average number of copies of target amplicons.

An advantage of the methods described herein is that amplification can (but need not) be carried out in small reaction volumes. In particular embodiments, the volume of the amplification mixtures is in the range of about 1 picoliter to about 50 nanoliters. In certain embodiments, the volume of the amplification mixtures is in the range of about 5 picoliters to about 25 nanoliters.

The methods described herein can, optionally, include recovering the target amplicons from the amplification mixtures. In certain embodiments, the target amplicons are recovered in a volume and/or copy number that varies less than about 50% among the recovered target amplicons. The recovered amplicons can be employed for further amplification and/or analysis (e.g., DNA sequencing). In some embodiments, at least one target amplicon can be subjected to amplification using primers specific for the first and second nucleotide tags to produce a target amplicon lacking the barcode nucleotide sequence, if such is desired.

In particular embodiments of the methods described herein, the target nucleic acids include genomic DNA. In variations of these embodiments, the genomic DNA can be DNA intended for DNA sequencing, e.g., automated DNA sequencing In certain embodiments, one or more of the forward primer, reverse primer, and barcode primer can include at least one additional primer binding site. For example, if a barcode primer is employed, the barcode primer can include at least a first additional primer binding site upstream of the barcode nucleotide sequence, which is upstream of the first nucleotide tag. In such an embodiment, the reverse primer can include at least a second additional primer binding site downstream of the second nucleotide tag. In particular embodiments, where the target nucleotide sequences are to be sequenced by automated DNA sequencing, the first and second additional primer binding sites are capable of being bound by DNA sequencing primers.

If a barcode primer is not employed, and the target nucleotide sequences are tagged after amplification, the first and second nucleotide tags can be capable of being bound by DNA sequencing primers.

Thus, the methods described herein can, optionally, include subjecting at least one target amplicon to DNA sequencing.

In certain embodiments, the method can, optionally, include quantifying the amount of target amplicons in the amplification mixtures. This step may be carried out, for example, prior to automated DNA sequencing. In particular embodiments, quantification includes recovering the target amplicons and subjecting them to digital amplification. Digital amplification includes, in particular embodiments, distributing the preamplified target amplicons into discrete reaction mixtures, wherein each reaction mixture, on average, includes no more than one amplicon per reaction mixture; and subjecting the reaction mixtures to amplification.

Quantification in digital amplification may be carried out by real-time PCR and/or endpoint PCR.

The amplification methods described herein can, optionally, include determining the amount of each target nucleic acid present in each sample. In certain embodiments, the methods can be performed in determining the copy numbers of the target nucleic acids in each sample. In particular embodiments, the methods can be performed in determining the genotypes at loci corresponding to the target nucleic acids. In other embodiments, the methods can be performed in determining the expression levels of the target nucleic acids.

In particular embodiments, the present invention relates to microfluidic devices. More particularly, the present invention relates to a microfluidic device that provides for recovery of reaction products. Merely by way of example, the method and apparatus has been applied to a PCR sample preparation system used to prepare libraries for next generation sequencing. However, it would be recognized that the invention has a much broader range of applicability.

According to an embodiment of the present invention, a microfluidic device is provided. The microfluidic device includes a plurality of first input lines and a plurality of second input lines. The microfluidic device also includes a plurality of sets of first chambers and a plurality of sets of second chambers. Each set of first chambers is in fluid communication with one of the plurality of first input lines and each set of second chambers is in fluid communication with one of the plurality of second input lines. The microfluidic device further includes a plurality of first pump elements in fluid communication with a first portion of the plurality of second input lines and a plurality of second pump elements in fluid communication with a second portion of the plurality of second input lines.

According to another embodiment of the present invention, a method of operating a microfluidic device having an assay chamber, a sample chamber, and a harvesting port is provided. The method includes closing a fluid line between the assay chamber and the sample chamber, flowing a sample into the sample chamber via a sample input line, and flowing an assay into the assay chamber via an assay input line. The method also includes opening the fluid line between the assay chamber and the sample chamber, combining at least a portion of the sample and at least a portion of the assay to form a mixture, and reacting the mixture to form a reaction product. The method further includes closing the fluid line between the assay chamber and the sample chamber, flowing a harvesting reagent from the harvesting port to the sample chamber, and removing the reaction product from the microfluidic device.

According to a particular embodiment of the present invention, a method of preparing reaction products is provided. The method includes providing M samples and providing N assays. The method also includes mixing the M samples and N assays to form M×N pairwise combinations. Each of the M×N pairwise combinations are contained in a closed volume. The method further includes forming M×N reaction products from the M×N pairwise combinations and recovering the M×N reaction products.

Many benefits are achieved by way of the present invention over conventional techniques. For example, embodiments of the present invention provide for mixing and reaction of M×N samples and assays followed by recovery of the reaction products in sample-by-sample pools. Additionally, dilation pumping is utilized to remove substantially all of the reaction products from the microfluidic device, providing uniformity between the various reaction product pools. Utilizing the systems and methods described herein, the time and labor required to prepare libraries is reduced in comparison with conventional techniques. These and other embodiments of the invention along with many of its advantages and features are described in more detail in conjunction with the text below and attached figures.

BRIEF DESCRIPTION OF THE DRAWINGS

The invention may be understood by reference to the following description taken in conjunction with the accompanying drawings that illustrate certain specific embodiments of the present invention.

FIGS. 9A-9D are simplified schematic diagrams illustrating fluid flow through a microfluidic device that permits recovery of reaction products during operation.

FIG. 17 shows the results from Example 6: Successful amplication of a PCR product using the 4-primer strategy designed for use on the Illumina GA II sequencer. The barcode primers listed in Table 14 are labelled as Outer Short.

DETAILED DESCRIPTION

Figure 1:
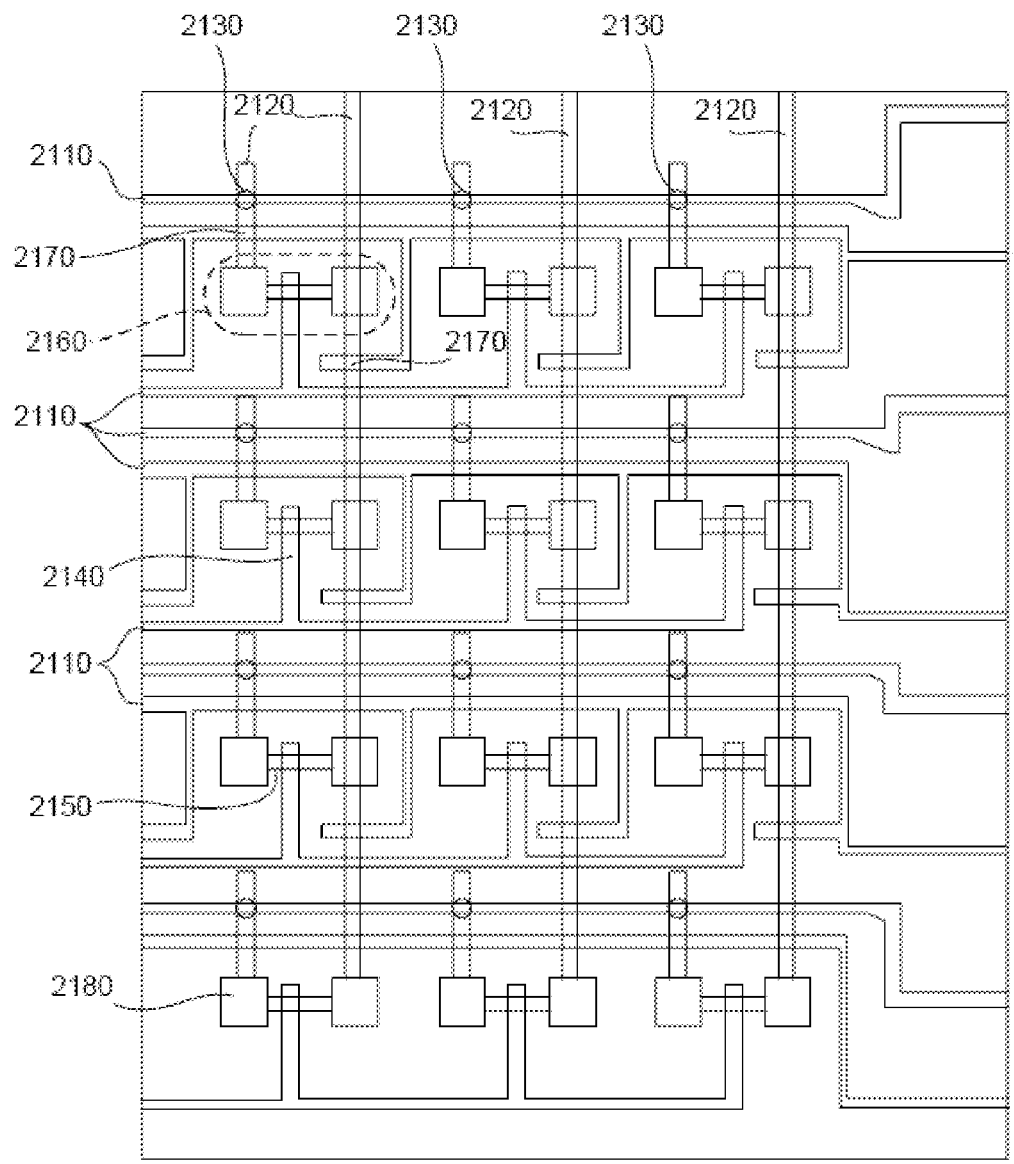
FIG. 1 depicts an illustrative matrix-type microfluidic device in plan view.

In certain embodiments, the present invention provides amplification methods in which nucleotide tag(s) and a barcode nucleotide sequence are added to target nucleotide sequences. The added sequences can then serve as primer and/or probe-binding sites. The barcode nucleotide sequence can encode information, such as, e.g., sample origin, about the target nucleotide sequence to which it is attached. Tagging and/or barcoding target nucleotide sequences can increase the number of samples that can be analyzed for one or multiple targets in a single assay, while minimizing increases in assay cost. The methods are particularly well-suited for increasing the efficiency of assays performed on microfluidic devices.

In particular embodiments, the methods are used to prepare nucleic acids for DNA sequencing by, e.g., adding binding sites for DNA sequencing primers, optionally followed by sample calibration for DNA sequencing. In specific, illustrative embodiments, the method can be employed to add binding sites for DNA sequencing primers in a microfluidic device that permits recovery of reaction products. In illustrative devices of this type, dilation pumping can utilized to remove substantially all of the reaction products from the microfluidic device, providing uniformity between the various reaction product pools. Thus, it is possible to produce pools of barcoded reaction products that are uniform with respect to volume and copy number. In various embodiments, the volume and/or copy number uniformity is such that the variability, with respect to volume and/or copy number, of each pool recovered from the device is less than about 100 percent, less than about 90 percent, less than about 80 percent, less than about 70 percent, less than about 60 percent, less than about 50 percent, less than about 40 percent, less than about 30 percent, less than about 20 percent, less than about 17 percent, or less than about 15, 12, 10, 9, 8, 7, 6, 5, 4.5, 4, 3.5, 3, 2.5, 2, 1.5, 1, or 0.5 percent. Those of skill in the art appreciate that the volume and/or copy number variability may fall within any range bounded by any of these values (e.g., about 2 to about 7 percent). In an illustrative embodiment, the volume samples recovered from a microfluidic device vary by no more than approximately 10%. Standard pipetting error is on the order of between 5 and 10%. Thus, the observed variability in volumes is largely attributable to pipetting error. Utilizing the systems and methods described herein, the time and labor required to prepare sequencing libraries is reduced in comparison with conventional techniques.

It is understood that the invention is not limited to the particular methodology, protocols, and reagents, etc., described herein, as these can be varied by the skilled artisan. It is also understood that the terminology used herein is used for the purpose of describing particular illustrative embodiments only, and is not intended to limit the scope of the invention. It also noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention.

Definitions

Terms used in the claims and specification are defined as set forth below unless otherwise specified. These terms are defined specifically for clarity, but all of the definitions are consistent with how a skilled artisan would understand these terms.

The term "adjacent," when used herein to refer two nucleotide sequences in a nucleic acid, can refer to nucleotide sequences separated by 0 to about 20 nucleotides, more specifically, in a range of about 1 to about 10 nucleotides, or sequences that directly abut one another.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to particular nucleic acids to be detected in the methods of the invention.

As used herein the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% G+C)$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence. For example, in certain embodiments, amplification primers used herein are said to "anneal to a nucleotide tag." This description encompasses primers that anneal wholly to the nucleotide tag, as well as primers that anneal partially to the nucleotide tag and partially to an adjacent nucleotide sequence, e.g., a target nucleotide sequence. Such hybrid primers can increase the specificity of the amplification reaction.

As used herein, the selection of primers "so as to avoid substantial annealing to the target nucleic acids" means that primers are selected so that the majority of the amplicons detected after amplification are "full-length" in the sense that they result from priming at the expected sites at each end of the target nucleic acid, as opposed to amplicons resulting from priming within the target nucleic acid, which produces shorter-than-expected amplicons. In various embodiments, primers are selected to that at least 55%, at least 60%, at least 65%, at least 70%, at least 75%, at least 80%, at least 85%, at least 90%, at least 95%, at least 96%, at least 97%, at least 98%, or at least 99% are full-length.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

The term "nucleotide tag" is used herein to refer to a predetermined nucleotide sequence that is added to a target nucleotide sequence. The nucleotide tag can encode an item of information about the target nucleotide sequence, such the identity of the target nucleotide sequence or the identity of the sample from which the target nucleotide sequence was derived. In certain embodiments, such information may be encoded in one or more nucleotide tags, e.g., a combination of two nucleotide tags, one on either end of a target nucleotide sequence, can encode the identity of the target nucleotide sequence.

As used herein the term "barcode primer" refers to a primer that includes a specific barcode nucleotide sequence that encodes information about the amplicon produced when the barcode primer is employed in an amplification reaction. For example, a different barcode primer can be employed to amplify one or more target sequences from each of a number of different samples, such that the barcode nucleotide sequence indicates the sample origin of the resulting amplicons.

As used herein, the term "encoding reaction" refers to reaction in which at least one nucleotide tag is added to a target nucleotide sequence. Nucleotide tags can be added, for example, by an "encoding PCR" in which the at least one primer comprises a target-specific portion and a nucleotide tag located on the 5' end of the target-specific portion, and a second primer that comprises only a target-specific portion or a target-specific portion and a nucleotide tag located on the 5' end of the target-specific portion. For illustrative examples of PCR protocols applicable to encoding PCR, see pending WO Application US03/37808 as well as U.S. Pat. No. 6,605,451. Nucleotide tags can also be added by an "encoding ligation" reaction that can comprise a ligation reaction in which at least one primer comprises a target-specific portion and nucleotide tag located on the 5' end of the target-specific portion, and a second primer that comprises a target-specific portion only or a target-specific portion and a nucleotide tag located on the 5' end of the target specific portion. Illustrative encoding ligation reactions are described, for example, in U.S. Patent Publication No. 2005/0260640, which is hereby incorporated by reference in its entirety, and in particular for ligation reactions.

As used herein an "encoding reaction" produces a "tagged target nucleotide sequence," which includes a nucleotide tag linked to a target nucleotide sequence.

As used herein with reference to a portion of a primer, the term "target-specific" nucleotide sequence refers to a sequence that can specifically anneal to a target nucleic acid or a target nucleotide sequence under suitable annealing conditions.

As used herein with reference to a portion of a primer, the term "nucleotide tag-specific nucleotide sequence" refers to a sequence that can specifically anneal to a nucleotide tag under suitable annealing conditions.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO00056927A3, and PCT Publication No. W09803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

The term "qPCR" is used herein to refer to quantitative real-time polymerase chain reaction (PCR), which is also known as "real-time PCR" or "kinetic polymerase chain reaction."

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "universal detection probe" is used herein to refer to any probe that identifies the presence of an amplification product, regardless of the identity of the target nucleotide sequence present in the product.

The term "universal qPCR probe" is used herein to refer to any such probe that identifies the presence of an amplification product during qPCR. In particular embodiments, nucleotide tags according to the invention can comprise a nucleotide sequence to which a detection probe, such as a universal qPCR probe binds. Where a tag is added to both ends of a target nucleotide sequence, each tag can, if desired, include a sequence recognized by a detection probe. The combination of such sequences can encode information about the identity or sample source of the tagged target nucleotide sequence. In other embodiments, one or more amplification primers can comprise a nucleotide sequence to which a detection probe, such as a universal qPCR probe binds. In this manner, one, two, or more probe binding sites can be added to an amplification product during the amplification step of the methods of the invention. Those of skill in the art recognize that the possibility of introducing multiple probe binding sites during preamplification (if carried out) and amplification facilitates multiplex detection, wherein two or more different amplification products can be detected in a given amplification mixture or aliquot thereof.

The term "universal detection probe" is also intended to encompass primers labeled with a detectable label (e.g., a fluorescent label), as well as non-sequence-specific probes, such as DNA binding dyes, including double-stranded DNA (dsDNA) dyes, such as SYBR Green.

The term "target-specific qPCR probe" is used herein to refer to a qPCR probe that identifies the presence of an amplification product during qPCR, based on hybridization of the qPCR probe to a target nucleotide sequence present in the product.

"Hydrolysis probes" are generally described in U.S. Pat. No. 5,210,015, which is incorporated herein by reference in its entirety for its description of hydrolysis probes. Hydrolysis probes take advantage of the 5'-nuclease activity present in the thermostable Taq polymerase enzyme typically used in the PCR reaction (TagMan® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe anneals downstream of one of the primers that defines one end of the target nucleic acid in a PCR reaction. Using the polymerase activity of the Taq enzyme, amplification of the target nucleic acid is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, hydrolysis probes suitable for use in the invention can be capable of detecting 8-mer or 9-mer motifs that are common in the human and other genomes and/or transcriptomes and can have a high $T_m$ of about 70° C. enabled by the use of linked nucleic acid (LNA) analogs.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

A "polymorphic marker" or "polymorphic site" is a locus at which nucleotide sequence divergence occurs. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

Amplification Methods

In General

In particular embodiments, the invention provides an amplification method for introducing a plurality (e.g., at least three) of selected nucleotide sequences into one or more target nucleic acid(s). The method entails amplifying a plurality of target nucleic acids, typically, in a plurality of samples. In illustrative embodiments, the same set of target nucleic acids can be amplified in each of two or more different samples. The samples can differ from one another in any way, e.g., the samples can be from different tissues, subjects, environmental sources, etc. At least three primers can be used to amplify each target nucleic acid, namely: forward and reverse amplification primers, each primer including a target-specific portion and one or both primers including a nucleotide tag. The target-specific portions can specifically anneal to a target under suitable annealing conditions. The nucleotide tag for the forward primer can have a sequence that is the same as, or different from, the nucleotide tag for the reverse primer. Generally, the nucleotide tags are 5' of the target-specific portions. The third primer is a barcode primer comprising a barcode nucleotide sequence and a first and/or second nucleotide tag-specific portion. The barcode nucleotide sequence is a sequence selected to encode information about the amplicon produced when the barcode primer is employed in an amplification reaction. The tag-specific portion can specifically anneal to the one or both nucleotide tags in the forward and reverse primers. The barcode primer is generally 5' of the tag-specific portion.

The barcode primer is typically present in the amplification mixture in excess of the forward and/or reverse primer(s). More specifically, if the barcode primer anneals to the nucleotide tag in the forward primer, the barcode primer is generally present in excess of the forward primer. If the barcode primer anneals to the nucleotide tag in the reverse primer, the barcode primer is generally present in excess of the reverse primer. In each instance the third primer in the amplification mixture, i.e., the reverse primer or the forward primer, respectively, can be present, in illustrative embodiments, at a concentration approximately similar to that of the barcode primer. Generally the barcode primer is present in substantial excess. For example, the concentration of the barcode primer in the amplification mixtures can be at least 2-fold, at least 4-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 500-fold, at least $10^3$-fold, at least $5 \times 10^3$-fold, at least $10^4$-fold, at least $5 \times 10^4$-fold, at least $10^5$-fold, at least $5 \times 10^5$-fold, at least $10^6$-fold, or higher, relative to the concentration of the forward and/or reverse primer(s). In addition, the concentration excess of the barcode primer can fall within any range having any of the above values as endpoints (e.g., 2-fold to $10^5$-fold). In illustrative embodiments, where the barcode primer has a tag-specific portion that is specific for the nucleotide tag on the forward primer, the forward primer can be present in picomolar to nanomolar concentrations, e.g., about 5 pM to 500 nM, about 5 pM to 100 nM, about 5 pM to 50 nM, about 5 pM to 10 nM, about 5 pM to 5 nM, about 10 pM to 1 nM, about 50 pM to about 500 pM, about 100 pM or any other range having any of these values as endpoints (e.g., 10 pM to 50 pM). Suitable, illustrative concentrations of barcode primer that could be used on combination with any of these concentrations of forward primer include about 10 nM to about 10 µM, about 25 nM to about 7.5 µM, about 50 nM to about 5 µM, about 75 nM to about 2.5 µM, about 100 nM to about 1 µM, about 250 nM to about 750 nM, about 500 nM or any other range having any of these values as endpoints (e.g., 100 nM to 500 nM). In amplification reactions using such concentrations of forward and barcode primers, the reverse primer have a concentration on the same order as the barcode primer (e.g. within about 10-fold, within about 5-fold, or equal).

Each amplification mixture can be subjected to amplification to produce target amplicons comprising tagged target nucleotide sequences, each comprising first and second nucleotide tags flanking the target nucleotide sequence, and at least one barcode nucleotide sequence at the 5' or 3' end of the target amplicon (relative to one strand of the target amplicon). In certain embodiments, the first and second nucleotide tags and/or the barcode nucleotide sequence are selected so as to avoid substantial annealing to the target nucleic acids. In such embodiments, the tagged target nucleotide sequences can include molecules having the following elements: 5'-(barcode nucleotide sequence)-(first nucleotide tag from the forward primer)-(target nucleotide sequence)-(second nucleotide tag sequence from the reverse primer)-3' or 5'-(first nucleotide tag from the forward primer)-(target nucleotide sequence)-(second nucleotide tag sequence from the reverse primer)-(barcode nucleotide sequence)-3'.

In illustrative embodiments, the barcode nucleotide sequence identifies a particular sample. Thus, for example, a set of T target nucleic acids can be amplified in each of S samples, where S and T are integers, typically greater than one. In such embodiments, amplification can be performed separately for each sample, wherein the same set of forward and reverse primers is used for each sample and the set of forward and reverse primers has at least one nucleotide tag that is common to all primers in the set. A different barcode primer can be used for each sample, wherein the bar code primers have different barcode nucleotide sequences, but the same tag-specific portion that can anneal to the common nucleotide tag. This embodiment has the advantage of reducing the number of different primers that would need to be synthesized to encode sample origin in amplicons produced for a plurality of target sequences. Alternatively, different sets of forward and reverse primers can be employed for each sample, wherein each set has a nucleotide tag that is different from the primers in the other set, and different barcode primers are used for each sample, wherein the barcode primers have different barcode nucleotide sequences and different tag-specific portions. In either case, the amplification produces a set of T amplicons from each sample that bear sample-specific barcodes.

In embodiments, wherein the same set of forward and reverse primers is used for each sample, the forward and reverse primers for each target can be initially combined separately from the sample, and each barcode primer can be initially combined with its corresponding sample. Aliquots of the initially combined forward and reverse primers can then be added to aliquots of the initially combined sample and barcode primer to produce S×T amplification mixtures.

These amplification mixtures can be formed in any article that can be subjected to conditions suitable for amplification. For example, the amplification mixtures can be formed in, or distributed into, separate compartments of a microfluidic device prior to amplification. Suitable microfluidic devices include, in illustrative embodiments, matrix-type microfluidic devices, such as those described below.

Any amplification method can be employed to produce amplicons from the amplification mixtures. In illustrative embodiments, PCR is employed. The amplification is generally carried out for at least three cycles to introduce the first and second nucleotide tags and the barcode nucleotide sequence. In various embodiments, amplification is carried out for 5, 10, 15, 20, 25, 30, 35, 40, 45, or 50 cycles, or for any number of cycles falling within a range having any of these values as endpoints (e.g. 5-10 cycles). In particular embodiments, amplification is carried out for a sufficient number of cycles to normalize target amplicon copy number across targets and across samples (e.g., 15, 20, 25, 30, 35, 40, 45, or 50 cycles, or for any number of cycles falling within a range having any of these values as endpoints).

Particular embodiments of the above-described method provide substantially uniform amplification, yielding a plurality of target amplicons wherein the majority of amplicons are present at a level relatively close to the average copy number calculated for the plurality of target amplicons. Thus, in various embodiments, at least 50, at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicons are present at greater than 50 percent of the average number of copies of target amplicons and less than 2-fold the average number of copies of target amplicons.

The invention also provides, in certain embodiments, a method for amplifying a plurality of target nucleotides in which barcoding is, optionally, omitted and the target nucleotide sequences are tagged after amplification. More specifically, the invention provides a method for amplifying a plurality of target nucleic acids, typically, in a plurality of samples, that entails preparing an amplification mixture for each target nucleic acid. Each amplification mixture includes a forward primer including a target-specific sequence and a reverse primer including a target-specific sequence. The amplification mixtures are subjected to amplification to produce a plurality of target nucleotide sequences. The target nucleotide sequences are then tagged to produce a plurality of target amplicons, each including first and/or second nucleotide tags flanking the target nucleotide sequence. This method produces a plurality of target amplicons, wherein at least 50 percent of the target amplicons are present at greater than 50 percent of the average number of copies of target amplicons and less than 2-fold the average number of copies of target amplicons. In various embodiments of this method at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicons are present at greater than 50 percent of the average number of copies of target amplicons and less than 2-fold the average number of copies of target amplicons.

In various embodiments, the target nucleotide sequence amplified can be, e.g., 25 bases, 50 bases, 100 bases, 200 bases, 500 bases, or 750 bases. In certain embodiments of the above-described methods, a long-range amplification method, such as long-range PCR can be employed to produce amplicons from the amplification mixtures. Long-range PCR permits the amplification of target nucleotide sequences ranging from one or a few kilobases (kb) to over 50 kb. In various embodiments, the target nucleotide sequences that are amplified by long-range PCR are at least about 1, 2, 3, 4, 5, 6, 7, 8, 9, 10, 11, 12, 13, 14, 15, 20, 25, 30, 35, 40, 45, or 50 kb in length. Target nucleotide sequences can also fall within any range having any of these values as endpoints (e.g., 25 bases to 100 bases or 5-15 kb). The use of long-range PCR in the above-described methods can, in some embodiments, yield a plurality of target amplicons wherein at least 50, at least 55, at least 60, at least 65, or at least 70 percent of the target amplicons are present at greater than 50 percent of the average number of copies of target amplicons and less than 2-fold the average number of copies of target amplicons.

Long-range PCR is well known in the art. See, e.g., Cheng S, Fockler C, Barnes W M, Higuchi R (June 1994). "Effective amplification of long targets from cloned inserts and human genomic DNA". Proc. Natl. Acad. Sci. U.S.A. 91 (12): 5695-9. Enzymes, protocols, and kits for long-range PCR that are suitable for use in the methods described here are commercially available; examples include: Sequal-Prep™ Long PCR Kit (Invitrogen, USA), PfuUltra® II Fusion HS DNA polymerase (Stratagene), Phusion® DNA polymerases, Phusion® Flash High Fidelity PCR Master Mix (Finnzymes).

In certain embodiments, the target amplicons can be recovered from the amplification mixtures. For example, a matrix-type microfluidic device that is adapted to permit recovery of the contents of each reaction chamber (see below) can be employed for the amplification to generate the target amplicons. In variations of these embodiments, the target amplicons can be subjected to further amplification and/or analysis. For example, one or more target amplicon(s) can be subjected to amplification using primers specific for the first and second nucleotide tags to produce a target amplicon lacking the barcode nucleotide sequence. In certain embodiments, the amount of target amplicons produced in the amplification mixtures can be quantified during amplication, e.g., by quantitative real-time PCR, or after.

In particular embodiments, the above-described amplification methods are employed to produce amplicons suitable for automated DNA sequencing. In particular, the ability of the methods to provide substantially uniform amplification, as described above, of target nucleotide sequences is helpful in preparing DNA sequencing libraries having good coverage. In the context of automated DNA sequencing, the term "coverage" refers to the number of times the sequence is measured upon sequencing. A DNA sequencing library that has substantially uniform coverage can yield sequence data where the coverage is also substantially uniform. Thus, in various embodiments, upon performing automated sequencing of a plurality of target amplicons prepared as described herein, the sequences of at least 50 percent of the target amplicons are present at greater than 50 percent of the average number of copies of target amplicon sequences and less than 2-fold the average number of copies of target amplicon sequences. In various embodiments of this method at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicon sequences are present at greater than 50 percent of the average number of copies of target amplicon sequences and less than 2-fold the average number of copies of target amplicon sequences.

Preparation of Nucleic Acids for DNA Sequencing

Many current DNA sequencing techniques rely on "sequencing by synthesis." These techniques entail library creation, massively parallel PCR amplification of library molecules, and sequencing. Library creation starts with conversion of sample nucleic acids to appropriately sized fragments, ligation of adaptor sequences onto the ends of the fragments, and selection for molecules properly appended with adaptors. The presence of the adaptor sequences on the ends of the library molecules enables amplification of random-sequence inserts. The above-described methods for tagging nucleotide sequences can be substituted for ligation, to introduce adaptor sequences, as described in greater detail below.

In particular embodiments, the number of library DNA molecules produced in the massively parallel PCR step is low enough that the chance of two molecules associating with the same substrate, e.g. the same bead (in 454 DNA sequencing) or the same surface patch (in Solexa DNA sequencing) is low, but high enough so that the yield of amplified sequences is sufficient to provide a high throughput. As discussed further below, after suitable adaptor sequences are introduced, digital PCR can be employed to calibrate the number of library DNA molecules prior to sequencing by synthesis.

Addition of DNA Sequencing Primers to Nucleic Acids

The DNA to be sequenced can be any type of DNA. In particular embodiments, the DNA is genomic DNA from an organism. In variations of such embodiments, total genomic DNA obtained from a sample taken from an organism or from a DNA library is prepared for sequencing.

As described above, at least three primers are employed to prepare the DNA for sequencing: forward, reverse, and barcode primers. However, one or more of the forward primer, reverse primer, and barcode primer includes at least one additional primer binding site. In specific embodiments, the barcode primer includes at least a first additional primer binding site upstream of the barcode nucleotide sequence, which is upstream of the first nucleotide tag-specific portion. In certain embodiments, two of the forward primer, reverse primer, and barcode primer include at least one additional primer binding site (i.e, such that the amplicon produced upon amplification includes the nucleotide tag sequences, the barcode nucleotide sequence, and the two additional binding sites). For example, if the barcode primer includes a first additional primer binding site upstream of the barcode nucleotide sequence, in specific embodiments, the reverse primer can include at least a second additional primer binding site downstream of the second nucleotide tag. Amplification then yields a molecule having the following elements: 5'-(first additional primer binding site)-(barcode nucleotide sequence)-(first nucleotide tag from the forward primer)-(target nucleotide sequence)-(second nucleotide tag from the reverse primer)-(second additional primer binding site)-3'. In specific embodiments, the first and second additional primer binding sites are capable of being bound by DNA sequencing primers, to facilitate sequencing of the entire amplicon, including the barcode, which can, as discussed above, indicate sample origin.

In some embodiments, more than three primers can be employed to add desired elements to a target nucleotide sequence. For example, four primers can be employed to produce molecules having the same five elements discussed above, plus an optional additional barcode e.g., 5'-(first additional primer binding site)-(barcode nucleotide sequence)-(first nucleotide tag from the forward primer)-(target nucleotide sequence)-(second nucleotide tag from the reverse primer)-(additional barcode nucleotide sequence)-

(second additional primer binding site)-3'. In an illustrative four-primer embodiment, the forward primer includes a target-specific portion and first nucleotide tag, and the reverse primer includes a target-specific portion and a second nucleotide tag. Together, these two primers constitute the "inner primers." The remaining two primers are the "outer primers," which anneal to the first and second nucleotide tags present in the inner primers. One outer primer is the barcode primer, which can contain at least a first additional primer binding site upstream of the barcode nucleotide sequence, which is upstream of the first nucleotide tag-specific portion (i.e., the same barcode primer discussed in the previous paragraph). The second outer primer can include a second tag-specific portion, an additional barcode nucleotide sequence and, downstream of this, a second additional primer binding site.

Amplification to incorporate elements from more than three primers can be carried out in one or multiple amplification reactions. For example, a four-primer amplification can be carried out in one amplification reaction, in which all four primers are present. Alternatively, a four-primer amplification can be carried out, e.g., in two amplification reactions: one to incorporate the inner primers and a separate amplification reaction to incorporate the outer primers. Where all four primers are present in one amplification reaction, the outer primers are generally present in the reaction mixture in excess. The relative concentration values give above for the barcode primer relative to the forward and/or reverse primers also apply to the relative concentrations of the outer primers relative to inner primers in a one-step, four-primer amplification reaction.

In an illustrative embodiment of the four-primer amplification reaction, each of the outer primers contains a unique barcode. For example, one barcode primer would be constructed of the elements 5'-(first additional primer binding site)-(first barcode nucleotide sequence)-(first nucleotide tag)-3', and the second barcode primer would be constructed of the elements 5'-(second additional primer binding site)-(second barcode nucleotide sequence)-(second nucleotide tag)-3'. In this embodiment, a number (J) of first barcode primers can be combined with a number (K) of second barcode primers to create J×K unique amplification products.

In a further illustrative embodiment of the invention, more than four primers can be combined in a single reaction to append different combinations of additional primer binding sites, barcode sequences, and nucleotide tags. For example, outer barcode primers containing the following elements: 5'-(first additional primer binding site)-(first barcode nucleotide sequence)-(first nucleotide tag)-3', 5'-(first additional primer binding site)-(first barcode nucleotide sequence)-(second nucleotide tag)-3', 5'-(second additional primer binding site)-(first barcode nucleotide sequence)-(first nucleotide tag)-3', 5'-(second additional primer binding site)-(first barcode nucleotide sequence)-(second nucleotide tag)-3', can be combined with inner target-specific primers as described above to produce amplification product pools containing all combinations of the barcode primers with the desired amplicon sequence.

In other illustrative embodiments of the invention, outer barcode primers in any of the combinations described above, or other combinations that would be obvious to one of skill in the art, can be combined with more than one pair of target primer sequences bearing the same first and second nucleotide tag sequences. For example, inner primers containing up to ten different target-specific forward primer sequences combined with the same first nucleotide tag and up to ten different target-specific reverse primer sequences combined with the same second nucleotide tag can be combined with the up to 2 or up to 4 outer barcode primers to generate multiple amplification products as described above. In various embodiments, at least 10, at least 20, at least 50, at least 100, at least 200, at least 500, at least 1000, at least 2000, at least 5000 or at least 10000 different target-specific primer pairs bearing the same first nucleotide tag and second nucleotide tag would be combined with the up to 2 or up to 4 outer barcode primers to generate multiple amplification products.

The methods of the invention can include subjecting at least one target amplicon to DNA sequencing using any available DNA sequencing method. In particular embodiments, a plurality of target amplicons is sequenced using a high throughput sequencing method. Such methods typically use an in vitro cloning step to amplify individual DNA molecules. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (also known as "polony sequencing") and SOLiD sequencing, (Applied Biosystems Inc., Foster City, Calif.). See M. Margulies, et al. (2005) "Genome sequencing in microfabricated high-density picolitre reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslaysky et al. developed a single-molecule method (commercialized by Helicos Biosciences Corp., Cambridge, Mass.) that omits this amplification step, directly fixing DNA molecules to a surface. I. Braslaysky, et al. (2003) "Sequence information can be obtained from single DNA molecules" Proceedings of the National Academy of Sciences of the United States of America 100: 3960-3964.

DNA molecules that are physically bound to a surface can be sequenced in parallel. "Sequencing by synthesis," like dye-termination electrophoretic sequencing, uses a DNA polymerase to determine the base sequence. Reversible terminator methods (commercialized by Illumina, Inc., San Diego, Calif. and Helicos Biosciences Corp., Cambridge, Mass.) use reversible versions of dye-terminators, adding one nucleotide at a time, and detect fluorescence at each position in real time, by repeated removal of the blocking group to allow polymerization of another nucleotide. "Pyrosequencing" also uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89.

Sample Preparation by Digital PCR

In some embodiments, samples are loaded into an amplification device, for example, a PCR plate or a microfluidic device, at sample concentrations containing on average less than one amplification template per well or chamber. Each well or chamber in the device is prepared such that it contains suitable tagged target-specific primers and a unique combination of forward and reverse barcode primers. For example, one well can contain barcode primers containing the elements 5'-(first additional primer binding site)-(first barcode sequence)-(first nucleotide tag)-3', 5'-(second additional primer binding site)-(second barcode sequence)-(second nucleotide tag)-3'. A second well or chamber can contain barcode primers containing the elements 5'-(first additional primer binding site)-(third barcode sequence)-(first nucleotide tag)-3', 5'-(second additional primer binding site)-(fourth barcode sequence)-(second nucleotide tag)-3'. Amplification products produced in each well would be labeled uniquely with the combinations of barcode sequences loaded into these wells.

Sample Calibration by Digital PCR

In particular embodiments, the number of target amplicons produced, e.g. from a DNA library, using the above-described methods can be calibrated using a digital amplification method. The step is finds particular application in preparing DNA for sequencing by synthesis. For discussions of "digital PCR" see, for example, Vogelstein and Kinzler, 1999, *Proc Natl Acad Sci USA* 96:9236-41; McBride et al., U.S Patent Application Publication No. 20050252773, especially Example 5 (each of these publications are hereby incorporated by reference in their entirety, and in particular for their disclosures of digital amplification). Digital amplification methods can make use of certain-high-throughput devices suitable for digital PCR, such as microfluidic devices typically including a large number and/or high density of small-volume reaction sites (e.g., nano-volume reaction sites or reaction chambers). In illustrative embodiments, digital amplification is performed using a microfluidic device, such as the Digital Array microfluidic devices described below. Digital amplification can entail distributing or partitioning a sample among hundreds to thousands of reaction mixtures disposed in a reaction/assay platform or microfluidic device. In such embodiments, a limiting dilution of the sample is made across a large number of separate amplification reactions such that most of the reactions have no template molecules and give a negative amplification result. In counting the number of positive amplification results, e.g, at the reaction endpoint, one is counting the individual template molecules present in the input sample one-by-one. A major advantage of digital amplification is that the quantification is independent of variations in the amplification efficiency—successful amplifications are counted as one molecule, independent of the actual amount of product.

In certain embodiments, digital amplification can be carried out after preamplification of sample nucleic acids. Typically, preamplification prior to digital amplification is performed for a limited number of thermal cycles (e.g., 5 cycles, or 10 cycles). In certain embodiments, the number of thermal cycles during preamplification can range from about 4 to 15 thermal cycles, or about 4-10 thermal cycles. In certain embodiments the number of thermal cycles can be 3, 4, 5, 6, 7, 8, 9, 10, 11, 12, 13, 14, 15, or more than 15. The above-described amplification to produce adaptor sequence-containing amplicons for DNA sequencing can be substituted for the typical preamplification step.

Digital amplication methods are described in U.S. Publication No. 20090239308, published Sep. 24, 2009, which is hereby incorporated by reference in its entirety and, in particular, for its disclosure of digital amplification methods and devices. Generally, in digital amplification, identical (or substantially similar) amplification reactions are run on a nucleic acid sample, such as genomic DNA. The number of individual reactions for a given nucleic acid sample may vary from about 2 to over 1,000,000. Typically, the number of reactions performed on a sample is about 100 or greater, more typically about 200 or greater, and even more typically about 300 or greater. Larger scale digital amplification can also be performed in which the number of reactions performed on a sample is about 500 or greater, about 700 or greater, about 765 or greater, about 1,000 or greater, about 2,500 or greater, about 5,000 or greater, about 7,500 or greater, or about 10,000 or greater. The number of reactions performed may also be significantly higher, such up to about 25,000, up to about 50,000, up to about 75,000, up to about 100,000, up to about 250,000, up to about 500,000, up to about 750,000, up to about 1,000,000, or even greater than 1,000,000 assays per genomic sample.

In particular embodiments, the quantity of nucleic acid subjected to digital amplification is generally selected such that, when distributed into discrete reaction mixtures, each individual amplification reaction is expected to include one or fewer amplifiable nucleic acids. One of skill in the art can determine the concentration of target amplicon(s) produced as described above and calculate an appropriate amount for use in digital amplification. More conveniently, a set of serial dilutions of the target amplicon(s) can be tested. For example, a device that is commercially available from Fluidigm Corp. as the 12.765 Digital Array microfluidic device allows 12 different dilutions to be tested simultaneously. Optionally, a suitable dilution can be determined by generating a linear regression plot. For the optimal dilution, the line should be straight and pass through the origin. Subsequently the concentration of the original samples can be calculated from the plot.

The appropriate quantity of target amplicon(s) can be distributed into discrete locations or reaction wells or chambers such that each reaction includes, for example, an average of no more than about one amplicon per volume. The target amplicon(s) can be combined with reagents selected for quantitative or nonquantitative amplification, prior to distribution or after.

Following distribution, the reaction mixtures are subjected to amplification to identify those reaction mixtures that contained a target amplicon. Any amplification method can be employed, but conveniently, PCR is used, e.g., real-time PCR or endpoint PCR. This amplification can employ any primers capable of amplifying the target amplicon(s). Thus, in particular embodiments, the primers can be DNA sequencing primers that anneal to the primer binding sites introduced in the previous amplification step.

The concentration of any target amplicon (copies/µL) is correlated with the number of positive (i.e., amplification product-containing) reaction mixtures. See copending U.S. application Ser. No. 12/170,414, entitled "Method and Apparatus for Determining Copy Number Variation Using Digital PCR," which is incorporated by reference for all purposes, and, in particular, for analysis of digital PCR results. Also see Dube et al., 2008, "Mathematical Analysis of Copy Number Variation in a DNA Sample Using Digital PCR on a Nanofluidic Device" PLoS ONE 3(8): e2876. doi:10.1371/journal.pone.0002876, which is incorporated by reference for all purposes and, in particular, for analysis of digital PCR results.

In an illustrative embodiment of sample calibration for DNA sequencing by digital PCR, a PCR reaction mix containing roughly 100-360 amplicons per µl can be loaded onto a Digital Array microfluidic device, such as Fluidigm Corporation's (South San Francisco, Calif.) 12.765 Digital Array microfluidic device, described below. The microfluidic chip has 12 panels and each panel contains 765 chambers. Replicate panels on the digital chip can be assayed in order to obtain absolute quantification of the initial concentration of library. The diluted samples having typical relative coefficients of variation (between replicates) within 9-12% (or lower) can be used for sequencing. See. e.g., White III RA, Blainey P C, Fan C H, Quake S R. "Digital PCR provides sensitive and absolute calibration for high throughput sequencing" BMC Genomics 10:116 doi:10.1186/1471-2164-10-116.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, particularly mammals, and more particularly humans. Suitable nucleic acids can also be obtained from environmental sources (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo or from maternal blood. Samples can be obtained from live or dead organisms or from in vitro cultures. Illustrative samples can include single cells, paraffin-embedded tissue samples, and needle biopsies. Nucleic acids useful in the invention can also be derived from one or more nucleic acid libraries, including cDNA, cosmid, YAC, BAC, Pl, PAC libraries, and the like.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification steps of the methods of the invention to be performed. Where the target nucleic acids are RNA, the RNA can be reversed transcribed into cDNA by standard methods known in the art and as described in Sambrook, J., Fritsch, E. F., and Maniatis, T., *Molecular Cloning: A Laboratory Manual*. Cold Spring Harbor Laboratory Press, NY, Vol. 1, 2, 3 (1989), for example. The cDNA can then be analyzed according to the methods of the invention.

Target Nucleic Acids

Any target nucleic acid that can be tagged in an encoding reaction of the invention (described herein) can be detected using the methods of the invention. In typical embodiments, at least some nucleotide sequence information will be known for the target nucleic acids. For example, if the encoding reaction employed is PCR, sufficient sequence information is generally available for each end of a given target nucleic acid to permit design of suitable amplification primers. In an alternative embodiment, the target-specific sequences in primers could be replaced by random or degenerate nucleotide sequences.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, and/or mutated) in genetic diseases or other pathologies; sequences that are associated with desirable or undesirable traits; and/or sequences that uniquely identify an individual (e.g., in forensic or paternity determinations).

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) *Meth. Mol. Biol.*, 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; the solid support method of U.S. Pat. No. 4,458,066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods of the invention.

Microfluidic Devices

In certain embodiments, any of the methods of the invention can be carried out using a microfluidic device. In illustrative embodiments, the device is a matrix-type microfluidic device is one that allows the simultaneous combination of a plurality of substrate solutions with reagent solutions in separate isolated reaction chambers. It will be recognized, that a substrate solution can comprise one or a plurality of substrates and a reagent solution can comprise one or a plurality of reagents. For example, the microfluidic device can allow the simultaneous pair-wise combination of a plurality of different amplification primers and samples. In certain embodiments, the device is configured to contain a different combination of primers and samples in each of the different chambers. In various embodiments, the number of separate reaction chambers can be greater than 50, usually greater than 100, more often greater than 500, even more often greater than 1000, and sometimes greater than 5000, or greater than 10,000.

In particular embodiments, the matrix-type microfluidic device is a Dynamic Array ("DA") microfluidic device, an example of which is shown in FIG. 1. A DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DA microfluidic devices are described in PCT publication WO05107938A2 (Thermal Reaction Device and Method For Using The Same) and US Pat. Publication US20050252773A1, both incorporated herein by reference in their entireties for their descriptions of DA microfluidic devices. DA microfluidic devices may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DA microfluidic devices may be designed so that all of the reagent and sample channels are in the same elastomeric layer, with control channels in a different layer.

U.S. Patent Publication No. 2008/0223721 and PCT Publication No. WO 05/107938A2 describe illustrative matrix-type devices that can be used to practice the methods described herein. FIG. 21 of the latter is reproduced as FIG. 1 and shows an illustrative matrix design having a first elastomeric layer 2110 (1st layer) and a second elastomeric layer 2120 (2d layer) each having fluid channels formed therein. For example, a reagent fluid channel in the first layer 2110 is connected to a reagent fluid channel in the second layer 2120 through a via 2130, while the second layer 2120 also has sample channels therein, the sample channels and the reagent channels terminating in sample and reagent chambers 2180, respectively. The sample and reagent chambers 2180 are in fluid communication with each other through an interface channel 2150 that has an interface valve 2140 associated therewith to control fluid communication between each of the chambers 2180 of a reaction cell 2160. In use, the interface is first closed, then reagent is introduced into the reagent channel from the reagent inlet and sample is introduced into the sample channel through the sample inlet; containment valves 2170 are then closed to isolate each reaction cell 2160 from other reaction cells 2160. Once the reaction cells 2160 are isolated, the interface valve 2140 is opened to cause the sample chamber and the reagent chamber to be in fluid communication with each other so that a desired reaction may take place. It will be apparent from this (and the description in WO 05/107938A2) that the DA microfluidic device may be used for reacting M number of different samples with N number of different reagents.

Although the DA microfluidic devices described above in WO 05/107938 are well suited for conducting the methods described herein, the invention is not limited to any particular device or design. Any device that partitions a sample and/or allows independent pair-wise combinations of reagents and sample may be used. U.S. Patent Publication No. 20080108063 (which is hereby incorporated by reference it its entirety) includes a diagram illustrating the 48.48 Dynamic Array IFC (Integrated Fluidic Circuit), a commercially available device available from Fluidigm Corp. (South San Francisco Calif.). It will be understood that other configurations are possible and contemplated such as, for example, 48×96; 96×96; 30×120; etc.

In specific embodiments, the microfluidic device can be a Digital Array microfluidic device, which is adapted to perform digital amplification. Such devices can have integrated channels and valves that partition mixtures of sample and reagents into nanolitre volume reaction chambers. In some embodiments, the Digital Array microfluidic device is fabricated, at least in part, from an elastomer. Illustrative Digital Array microfluidic devices are described in copending U.S. Applications owned by Fluidigm, Inc., such as U.S. application Ser. No. 12/170,414, entitled "Method and Apparatus for Determining Copy Number Variation Using Digital PCR." One illustrative embodiment has 12 input ports corresponding to 12 separate sample inputs to the device. The device can have 12 panels, and each of the 12 panels can contain 765 6 nL reaction chambers with a total volume of 4.59 µL per panel. Microfluidic channels can connect the various reaction chambers on the panels to fluid sources. Pressure can be applied to an accumulator in order to open and close valves connecting the reaction chambers to fluid sources. In illustrative embodiments, 12 inlets can be provided for loading of the sample reagent mixture. 48 inlets can be used to provide a source for reagents, which are supplied to the biochip when pressure is applied to accumulator. Additionally, two or more inlets can be provided to provide hydration to the biochip. Hydration inlets are in fluid communication with the device to facilitate the control of humidity associated with the reaction chambers. As will be understood to one of skill in the art, some elastomeric materials that can utilized in the fabrication of the device are gas permeable, allowing evaporated gases or vapor from the reaction chambers to pass through the elastomeric material into the surrounding atmosphere. In a particular embodiment, fluid lines located at peripheral portions of the device provide a shield of hydration liquid, for example, a buffer or master mix, at peripheral portions of the biochip surrounding the panels of reaction chambers, thus reducing or preventing evaporation of liquids present in the reaction chambers. Thus, humidity at peripheral portions of the device can be increased by adding a volatile liquid, for example water, to hydration inlets. In a specific embodiment, a first inlet is in fluid communication with the hydration fluid lines surrounding the panels on a first side of the biochip and the second inlet is in fluid communication with the hydration fluid lines surrounding the panels on the other side of the biochip.

While the Digital Array microfluidic devices are well-suited for carrying out the digital amplification methods described herein, one of ordinary skill in the art would recognize many variations and alternatives to these devices. The microfluidic device which is the 12.765 Dynamic Array commercially available from Fluidigm Corp. (South San Francisco, Calif.), includes 12 panels, each having 765 reaction chambers with a volume of 6 nL per reaction chamber. However, this geometry is not required for the digital amplification methods described herein. The geometry of a given Digital Array microfluidic device will depend on the particular application. Additional description related to devices suitable for use in the methods described herein is provided in U.S. Patent Application Publication No. 2005/0252773, incorporated herein by reference for its disclosure of Digital Array microfluidic devices.

In certain embodiments, the methods described herein can be performed using a microfluidic device that provides for recovery of reaction products. Such devices are described in detail in copending U.S. Application No. 61/166,105, filed Apr. 2, 2009, which is hereby incorporated by reference in its entirety and specifically for its description of microfluidic devices that permit reaction product recovery and related methods. For example, the digital PCR method for calibrating DNA samples prior to sequencing can be preformed on such devices, permitting recovery of amplification products, which can then serve as templates for DNA sequencing.

Figure 2:
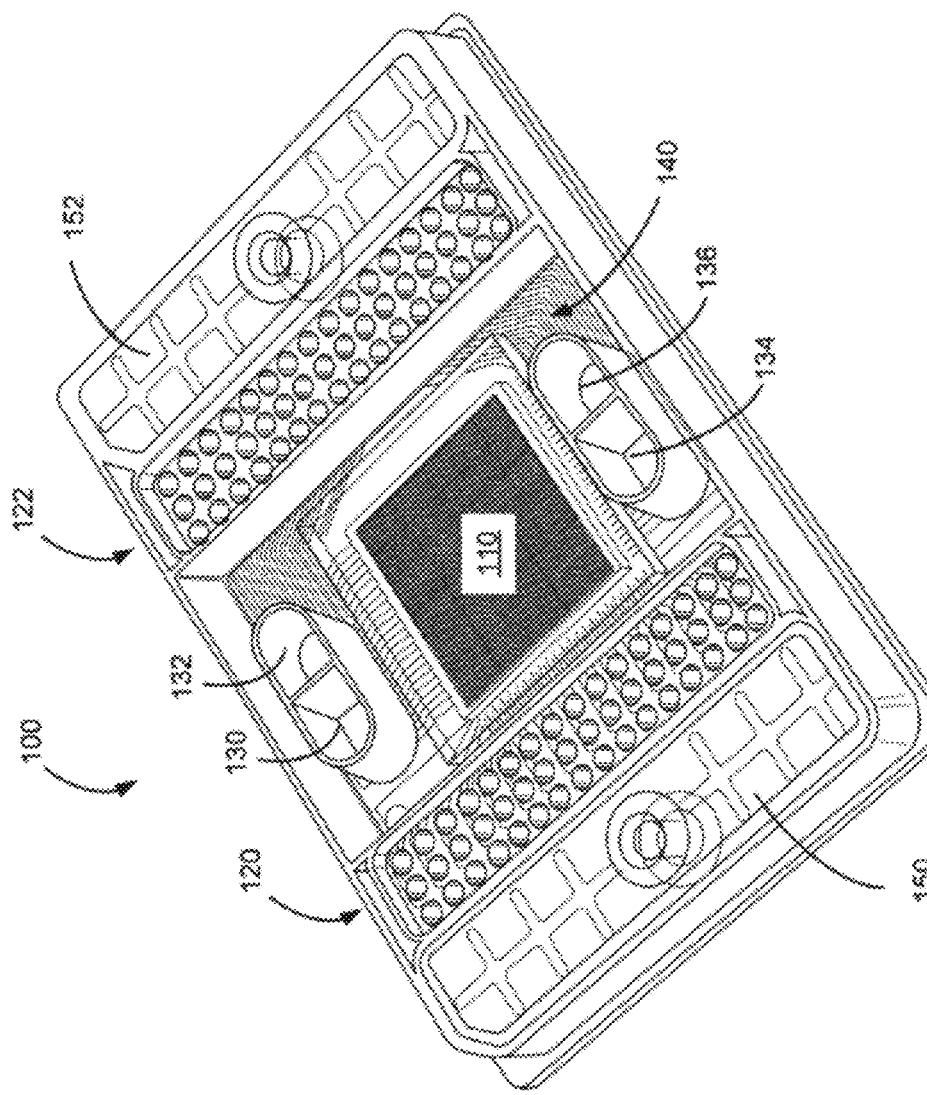
FIG. 2 is a simplified perspective illustration of a carrier and a microfluidic device that permits recovery of reaction products.

FIG. 2 is a simplified perspective illustration of a carrier and a microfluidic device according to an embodiment of the present invention. As illustrated in FIG. 2, the carrier 100 supports a microfluidic device 110, which may also be referred to as a Digital Array microfluidic device. The carrier 100 may be made from materials providing suitable mechanical support for the various elements of the carrier. As an example, the carrier is made using a plastic or other suitable material. The outer portion of the carrier has the same footprint as a standard 384-well microplate and enables stand-alone valve operation. Additionally, the carrier 100 is compatible with conventional stand-alone thermal cyclers. As described below, there are 48 sample input ports 120 located on a first side of the carrier 100 and 48 assay input ports 122 located on an opposing side of the carrier. The banks of sample input ports 120 and assay input ports 122 are recessed with respect to the top of the carrier. Utilizing these recessed features, pressure can be applied concurrently to all of the sample input ports or the assay input ports, driving fluids present in the respective ports through fluid lines 140 connecting the input ports and either vias, fluid input lines, or combinations thereof, present on the microfluidic device 110. The samples may include encoded primers and the assays may also be referred to as amplicon-specific (AS) primers.

The carrier 100 also includes four sources 130, 132, 134, and 136, which may be used to actuate control lines present in the microfluidic device. In an embodiment, sources 130, 132, and 134 are used to pressurize control lines operable to open and close valves present in the microfluidic device. For example, application of pressure greater than atmospheric pressure to source 132 will result in the liquid present in source 132 flowing into control lines present on the microfluidic device, thereby actuating valves operable to obstruct flow through one or more fluid input lines also present on the microfluidic device. In an embodiment, source 130 is used as a fluid well containing harvesting reagent. Pressure can be applied to source 130, forcing the harvesting reagent to flow through fluid lines provided on the carrier to fluid lines provided on the microfluidic device. Thus, application of pressure to source 130 can result in the flow of a harvesting reagent or other suitable fluid through the microfluidic device. The control lines that are in fluid communication with the sources 130-136 can include control lines for interface valves, containment valves, valves used in dilation pumping, fluid lines for the flow of harvesting reagent, or the like. In a particular embodiment, valve 1 is controlled by source 132, valve 2 is controlled by source 134, harvesting reagent is provided in source 130, and hydration reagent is provided in source 136. In this particular embodiment, the interface valves are controlled by source 150 and containment valves are controlled by source 152. This particular embodiment is not intended to limit the present invention, but merely to provide an example of one configuration. Other configurations can be utilized as appropriate to the particular application.

Figure 3:
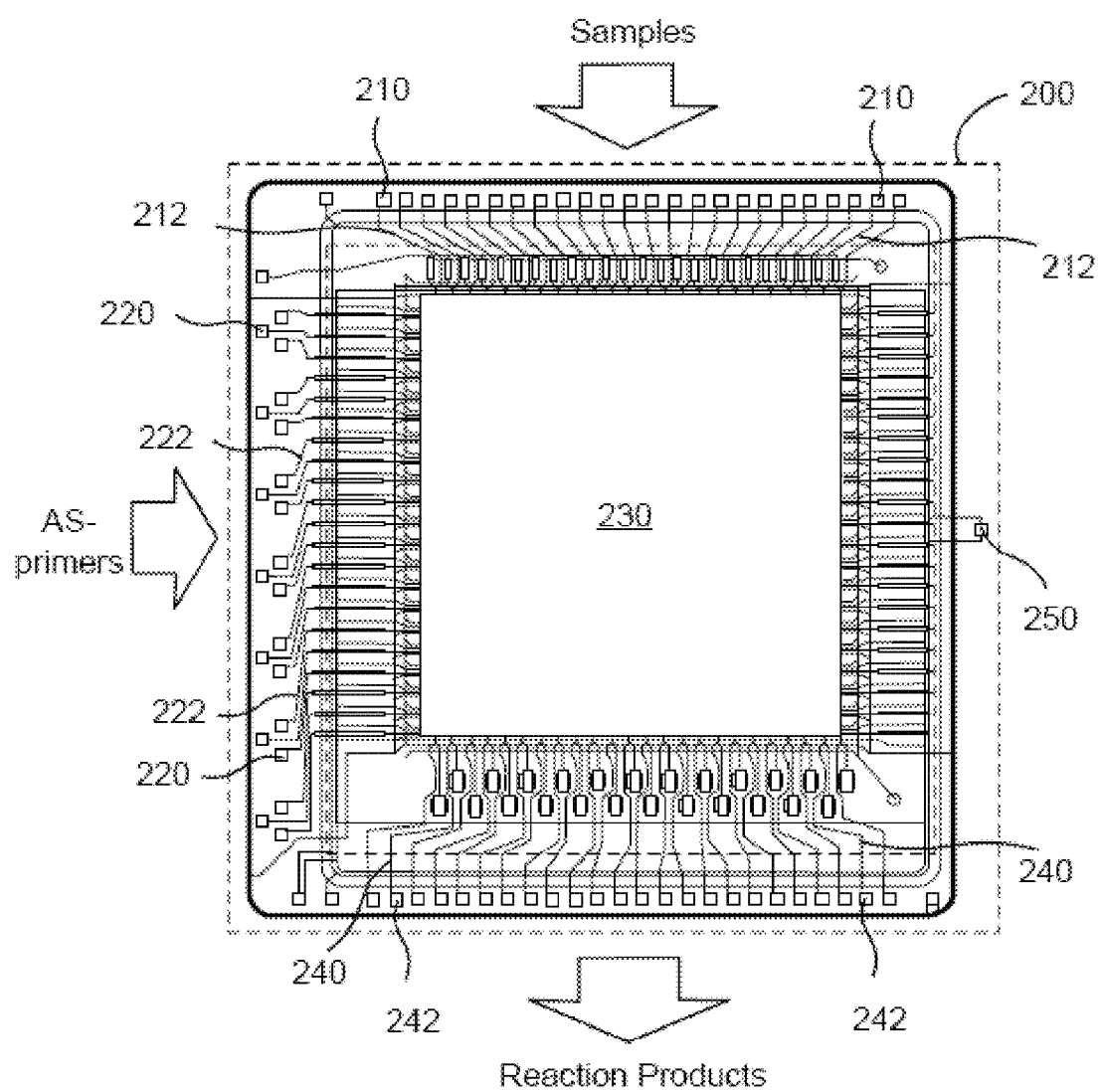
FIG. 3 is a simplified schematic diagram of a microfluidic device that permits recovery of reaction products.

As described more fully in relation to FIG. 3, fluid lines 140 present on the carrier 100 are in fluid communication with one or more fluid lines present on the microfluidic device 110. These fluid lines can serve to carry fluids into and out of the microfluidic device or may be used as control lines to actuate valves present on the microfluidic device. Thus, fluids provided in sample input ports 120 or assay input ports 122 can be loaded into appropriate fluid input lines and chambers of the microfluidic device. Other fluids (e.g., liquids) provided in sources 130-136 can also be loaded into either fluid input lines or control lines of the microfluidic device. Reaction products from the chambers of the microfluidic device can be recovered as they are pumped through fluid lines on the microfluidic device, back into the fluid lines 140 present on the carrier and into the sample or assay input ports 120 or 122.

Pressure accumulators 150 and 152 may be utilized to pressurize other control lines, provide for hydration of the microfluidic device, or they may not be used in some embodiments. Although 48 sample input ports and 48 assay input ports are shown in the embodiment of the present invention illustrated in FIG. 2, this is not required by the present invention. Other embodiments utilize a different number of samples and assays depending on the particular application. One of ordinary skill in the art would recognize many variations, modifications, and alternatives.

Figure 4:
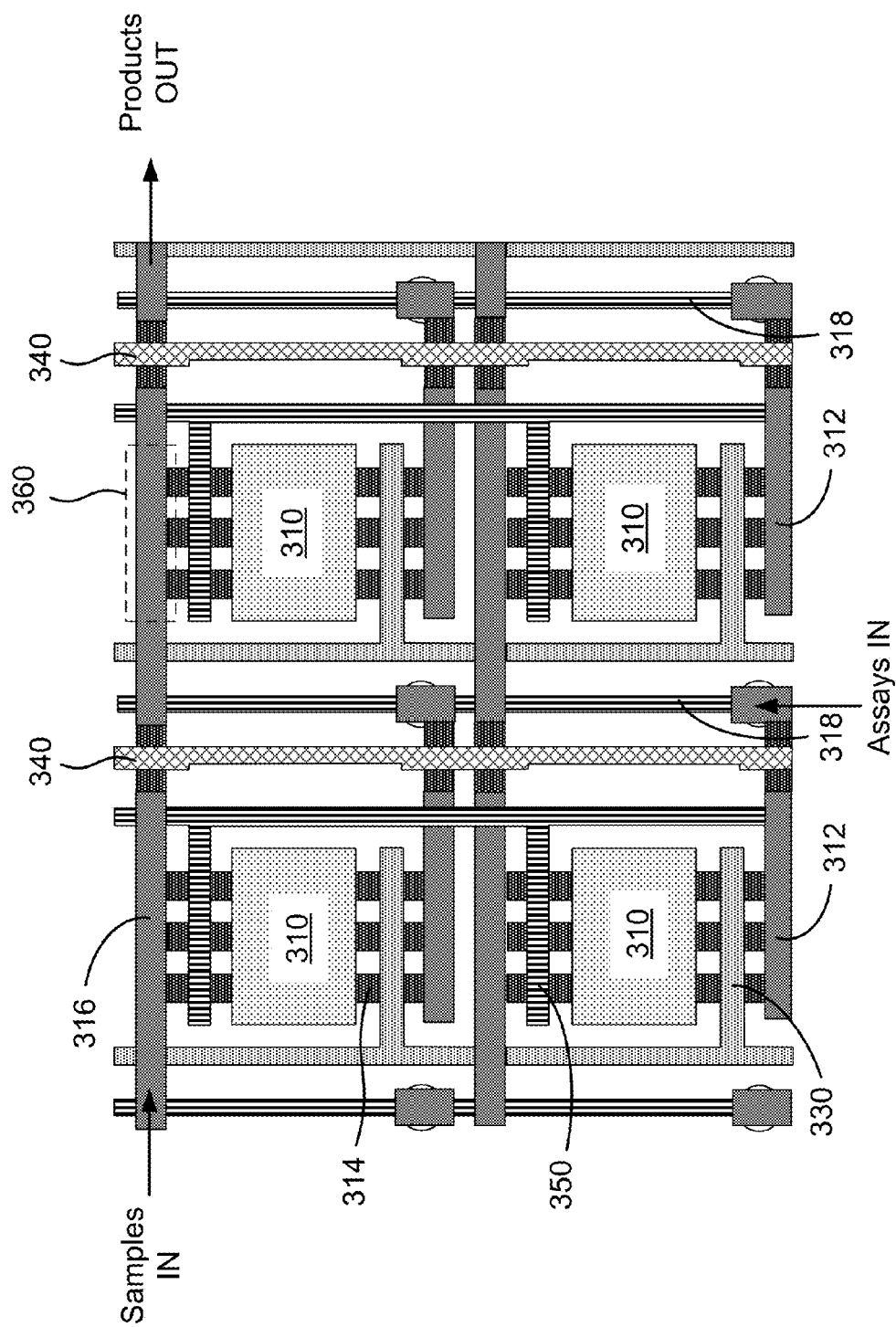
FIG. 4 is a simplified schematic diagram of several unit cells of the microfluidic device illustrated in FIG. 3.

FIG. 3 is a simplified schematic diagram of a microfluidic device according to an embodiment of the present invention. The microfluidic device 200 includes vias 210 connected to fluid input lines 212 that are used to provide fluid flow paths for 24 different samples. The 24 samples, which can be loaded into a subset of the sample input ports 120 illustrated in FIG. 1, flow through vias 210 and fluid input lines 212 to sample input lines 312 and eventually to sample chambers 310 as illustrated in FIG. 4. The microfluidic device 200 also includes vias 220 connected to fluid input lines 222 that are used to provide fluid flow paths for 21 different assays. The via 250 on the side of the microfluidic device opposing the assay input fluid lines provides for hydration, actuation of a control line, or other suitable operations. The array portion 230 of the microfluidic device is illustrated (in part) in FIG. 4. In the array portion 230, the samples and assays are loaded into sample and assay chambers and then can be mixed to form pairwise combinations.

As described more fully throughout the present specification, after samples and assays are mixed and reacted, the reaction products can be recovered from the microfluidic device by flowing a recovery fluid through the fluid input lines 212, through the array portion 230 of the microfluidic device as illustrated in FIG. 4, and through the output fluid lines 240 and vias 242. These output fluid lines are in fluid communication with output ports provided on a carrier. Thus, reaction products pooled from the combination of a sample with each of the various assays are separately provided through each of the independent output fluid lines 240.

The particular number of sample and assay input lines illustrated in FIG. 3 are provided merely by way of example and particular implementations are not limited to these particular numbers. In other embodiments, additional sample and assay input lines are provided in order to facilitate additional pairwise combinations of samples and assays in the microfluidic device.

FIG. 4 is a simplified schematic diagram of several unit cells of the microfluidic device illustrated in FIG. 3. In FIG. 4, four unit cells from the array portion 230 are illustrated for purposes of clarity. The sample input lines 316 are in fluid communication with the fluid input lines 212 and the assay input lines 318 are in fluid communication with the assay input lines 222 as illustrated in FIG. 3. The unit cell section of the microfluidic device includes sample chambers 310 and assay chambers 312. Fluid lines 314 provide for fluid communication between the sample chambers and the assay chambers when the interface valves 330 are in the open position. In a specific embodiment, sample input lines 316 are provided in a layer of the microfluidic device underlying the layer containing the sample chambers. In a similar manner, assay input lines 318 are provided in a layer of the microfluidic device underlying the layer containing the assay chambers. Samples flow from the sample input lines 212 illustrated in FIG. 3 to sample input lines 316 and up through one or more vias (not shown) passing from the sample input lines 316 to the sample chambers 310. Although the sample input lines 316 are illustrated as branching into three input lines as the fluid passes to the sample chambers, this particular number is not required by the present invention and other numbers of sample input lines, for example, 1 input line, 2, 4, or more than 4 sample input lines may be utilized. Similar design criteria are applicable to the three fluid lines 314 connecting the sample chambers and corresponding assay chambers. The sample input lines 316 provide a continuous flow path in the row direction of the figure, enabling a single sample to be distributed evenly among multiple sample chambers, for example, the top row of sample chambers or the bottom row of sample chambers.

Utilizing interface valves 330 and containment valves 340, each of the sample chambers can be isolated from each of the other sample chambers as well as the assay chambers. The assay chambers can be isolated from the other assay chambers using the containment valves. Both the isolation and containment valves are actuated by application of pressure to a corresponding control line present on the carrier or by other means, for example, electrostatic actuation.

FIG. 4 illustrates assay input lines 318, which provide for assay flow from assay input lines 222 illustrated in FIG. 3 to the assay chambers 312. When the containment valves are in the open position, assays are able to flow from the assay input lines to the assay chambers 312. In a specific embodiment, the assays flow through vias connecting the input lines and the assay chambers in a manner similar to the filling of the sample chambers. The loading of assays along the columns of the microfluidic device provide a different assay for each row of samples, resulting in M×N pairwise combinations.

Opening of the interface valves 330 enables the samples and the assays to mix in pairwise combinations via free interface diffusion. After the samples and assays are mixed, thermocycling can be performed to form reaction products. Reaction products are recovered from the microfluidic device by opening harvest valves 350, which enable the reaction products to flow into portions 360 of the sample input lines adjacent the sample chambers. Using sample input lines 316 and on-chip pumps (not shown), reaction products flow through the sample input lines toward recovery ports on the carrier.

In the embodiment illustrated in FIG. 4, samples load from a first side of the microfluidic device. The assays load from an adjacent side of the microfluidic device. After processing, a harvesting reagent is input from the first side of the device using the sample input lines and reaction products exit the microfluidic device out fluid lines running toward the side of the microfluidic device opposing the first side. In this embodiment, the remaining side of the microfluidic device is not used for sample or assay loading or reaction product unloading. Other configurations are included within the scope of the present invention and the example configuration illustrated in FIG. 4 is merely provided by way of example. One of ordinary skill in the art would recognize many variations, modifications, and alternatives.

A benefit provided by the systems described herein is that the volume of samples and assays used in the reactions are fixed, regardless of the pipetting volume dispensed into the sample input and the assay input ports. If the volume in the sample and/or assay input ports is above a predetermined threshold sufficient to fill the sample/assay input lines and the sample/assay chambers, then application of pressure to the sample/assay input ports will result in complete filling of the sample/assay chambers. The completely filled chambers thus provide a fixed reaction volume not available with conventional microtiter plate techniques.

Although systems have been developed by the present assignee to perform many simultaneous binding assays, including, but not limited to immunological experiments such as ELISA assays, embodiments of the present invention provide for dilation pumping "on-chip" as well as separate sample and assay chambers. Thus, pairwise combinations of samples and assays are possible using embodiments described herein that are not possible with previously developed techniques. Additional description of binding assays is provided in U.S. Patent Application Publication No. 2007/0074972, filed on Sep. 13, 2006, the disclosure of which is hereby incorporated by reference in its entirety for all purposes.

Embodiments of the present invention provide a system suitable for PCR sample preparation that features reduced cost, time, and labor in the preparation of amplicon libraries from an input DNA template. In a typical use case, the first amplification will be used to generate libraries for next-generation sequencing. Utilizing embodiments of the present invention, samples and encoded primers are combined with amplicon-specific (AS) primers to create a mixture that is suitable for desired reactions. Based on an M×N architecture of the microfluidic device, each of the M samples is combined with each of the N AS primers (i.e., assays) to form M×N pairwise combinations. That is, one reaction site is provided for each sample and assay pair. After the completion of the reaction (e.g., PCR), the reaction products are recovered from the system, typically using a harvest reagent that flows through the microfluidic device. In a specific embodiment, reaction products associated with each sample are recovered in a separate reaction pool, enabling further processing or study of the pool containing a given sample reacted with each of the various assays.

Thus, in embodiments described herein, a microfluidic device is provided in which independent sample inputs are combined with primer inputs in an M×N array configuration. Thus, each reaction is a unique combination of a particular sample and a particular primer. As described more fully throughout the present specification, samples are loaded into sample chambers in the microfluidic device through sample input lines arranged as columns in one implementation. AS primers or assays are loaded into assay chambers in the microfluidic device through assay input lines arranged as rows crossing the columns. The sample chambers and the assay chambers are in fluidic isolation during loading. After the loading process is completed, an interface valve operable to obstruct a fluid line passing between pairs of sample and assay chambers is opened to enable free interface diffusion of the pairwise combinations of samples and assays. Precise mixture of the samples and assays enables reactions to occur between the various pairwise combinations, producing a reaction product including a set of specific PCR reactions for which each sample has been effectively coded with a unique barcode. The reaction products are harvested and can then be used for subsequent sequencing processes. The terms "assay" and "sample" as used herein are descriptive of particular uses of the devices in some embodiments. However, the uses of the devices are not limited to the use of "sample(s)" and "assay(s)" in all embodiments. For example, in other embodiments, "sample(s)" may refer to "a first reagent" or a plurality of "first reagents" and "assay(s)" may refer to "a second reagent" or a plurality of "second reagents." The M×N character of the devices enable the combination of any set of first reagents to be combined with any set of second reagents.

According to one particular process implemented using an embodiment of the present invention, after 25 cycles of PCR, the reaction products from the M×N pairwise combinations will be recovered from the microfluidic device in discrete pools, one for each of the M samples. Typically, the discrete pools are contained in a sample input port provided on the carrier. In some processes, the reaction products may be harvested on a "per amplicon" basis for purposes of normalization. Utilizing embodiments of the present invention, it is possible to achieve results (for replicate experiments assembled from the same input solutions of samples and assays) for which the copy number of amplification products varies by no more than ±25% within a sample and no more than ±25% between samples. Thus, the amplification products recovered from the microfluidic device will be representative of the input samples as measured by the distribution of specific known genotypes. Preferably, output sample concentration will be greater than 2,000 copies/amplicon/microliter and recovery of reaction products will be performed in less than two hours.

Applications in which embodiments of the present invention can be used include sequencer-ready amplicon preparation and long-range PCR amplicon library production. For the sequencer-ready amplicon preparation, multiple-forward primer and 3-primer combination protocols can be utilized.

Figure 5A:
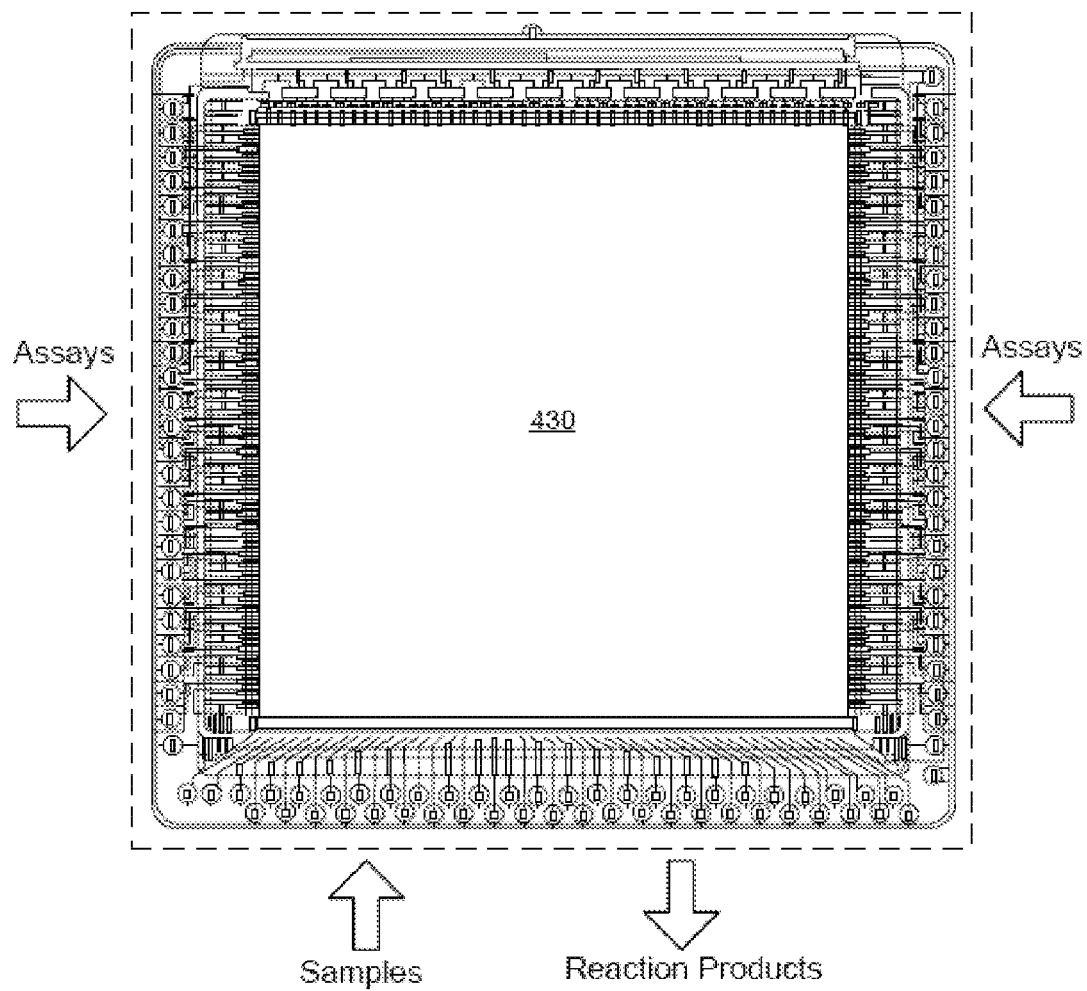
FIG. 5A is simplified schematic diagram of a microfluidic device that permits recovery of reaction products.

FIG. 5A is simplified schematic diagram of a microfluidic device according to another embodiment of the present invention. The microfluidic device illustrated in FIG. 5A shares common features as well as differences with the microfluidic device illustrated in FIG. 2. Samples are loaded into the microfluidic device through 48 vias and corresponding sample input lines provided at one edge of the microfluidic device (i.e., the bottom edge in FIG. 5A). Samples flow through the sample input lines into the array portion 430 of the microfluidic device. The assays are loaded from vias and assay input lines on two sides of the microfluidic device (i.e., the left and right sides in FIG. 5A). Additional discussion of the unit cells present in the array portion 430 is provided in relation to FIG. 6. Reaction products are removed through the sample input lines and are recovered in the sample input ports 120 provided on the carrier 100. Thus, in FIG. 5A, loading of samples and recovery of reaction products are illustrated as flowing through the bottom side of the microfluidic device.

Figure 5B:
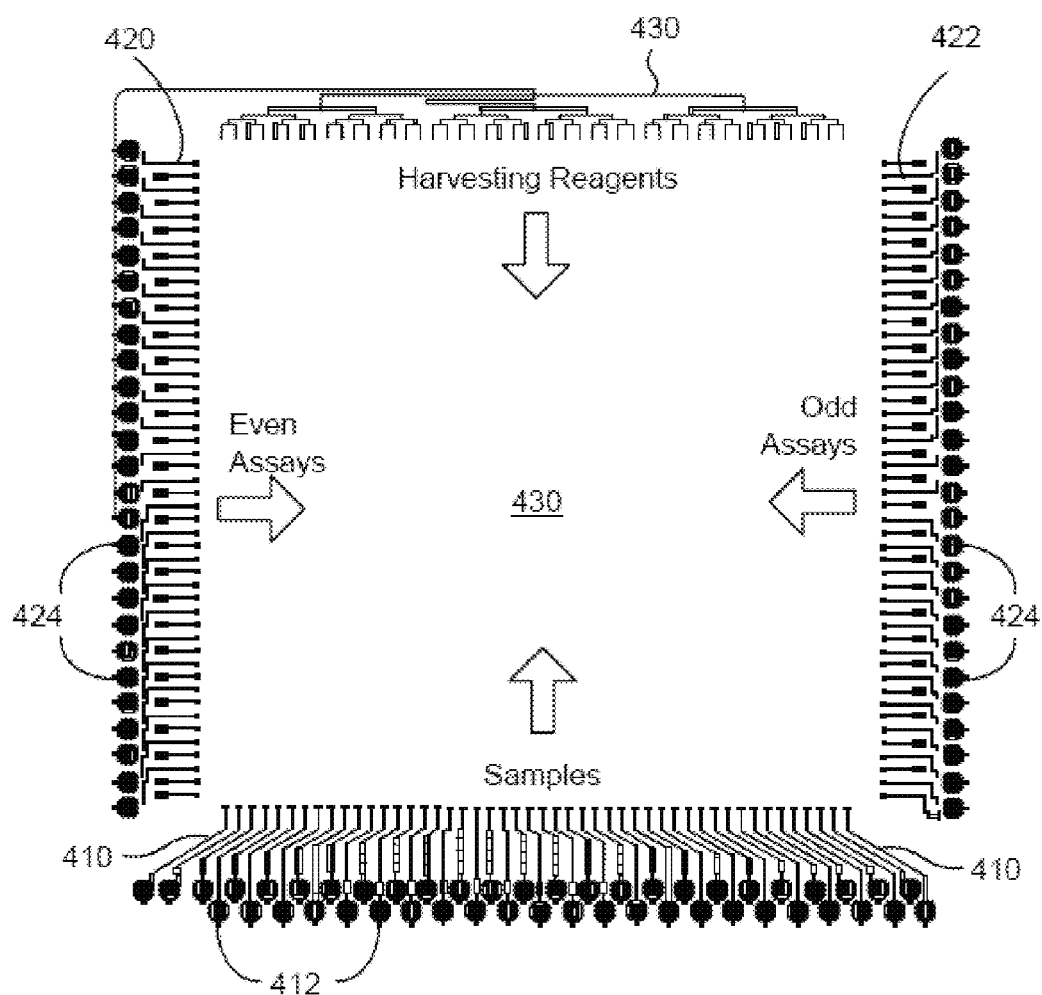
FIG. 5B is a simplified schematic diagram of portions of the microfluidic device illustrated in FIG. 5A.

FIG. 5B is a simplified schematic diagram of portions of the microfluidic device illustrated in FIG. 5A. The portions illustrated in FIG. 5B include sample input lines 410, assay input lines for even assays (assay input lines 420), assay input lines for odd assays (assay input lines 422), and a harvesting reagent input lines 430. In an embodiment, the sample input lines 410 are in fluid communication with vias 412 that are aligned with sample input lines 140, which are in fluid communication with sample input ports 120 as illustrated in FIG. 2. In other embodiments, additional sample input lines (not shown) are provided to enable fluid communication between the sample input ports 120 and the sample input lines 410. Thus, pressurization of the bank of sample input ports will result in flow of the various samples into the illustrated sample input lines 410.

Figure 6:
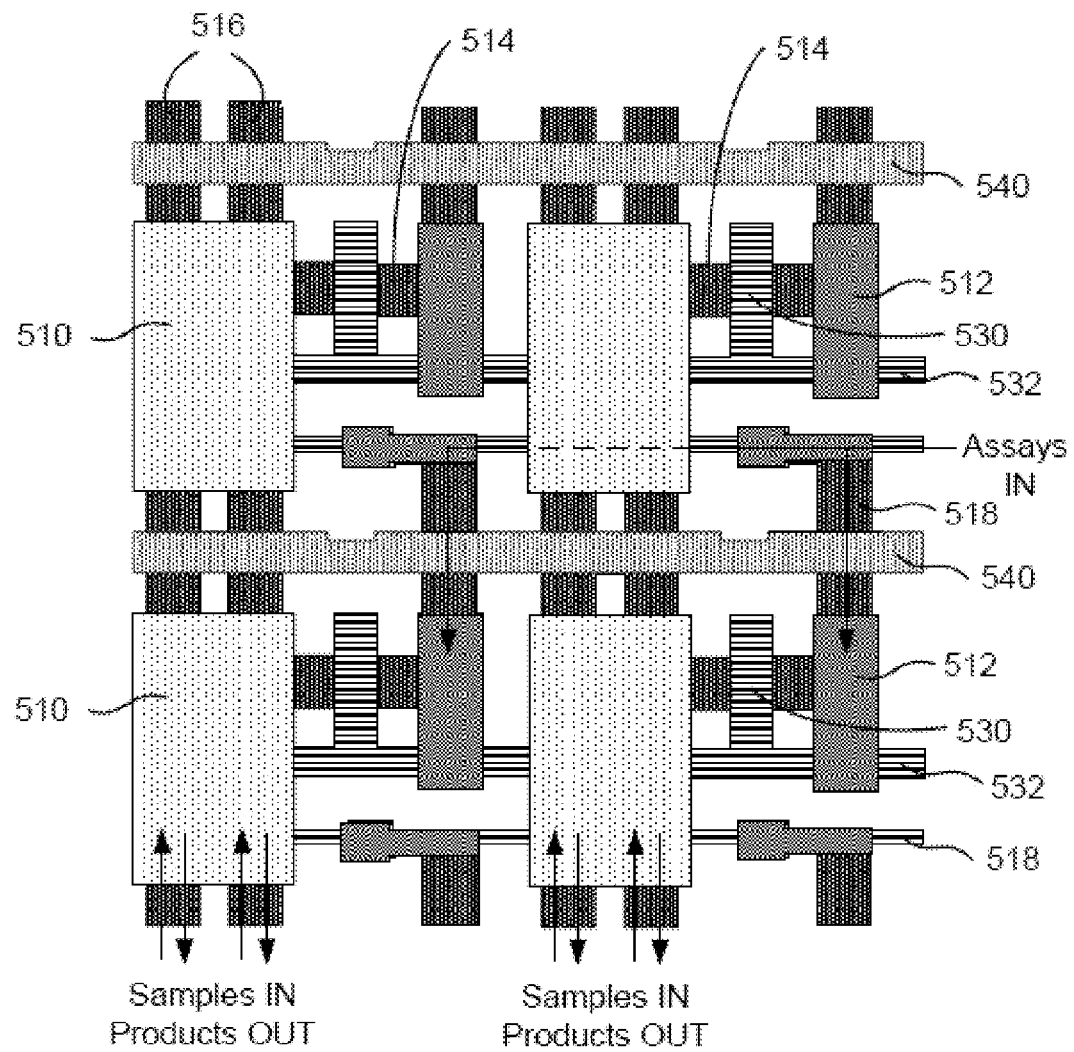
FIG. 6 is a simplified schematic diagram of several unit cells of the microfluidic device illustrated in FIG. 5A.

As discussed in relation to FIG. 6 below, sample input lines 410 are in fluid communication with sample input lines 516 and sample chambers 510 present in the microfluidic device. For an array with 48 sample chambers and 48 assay chambers, the 48 sample input lines 410 illustrated in FIG. 5B will provide samples to 48 separate columns of sample chambers, two of which are illustrated in FIG. 6. It should be noted that the various fluid lines illustrated in FIG. 5B can be integrated in carrier 100, integrated in the microfluidic device 110, or present in one or more other structures, depending on the particular implementation. Thus, the illustration of the sample input lines 410 in FIG. 5B is not intended to limit the scope of the present invention but merely to illustrate fluid lines suitable for providing controlled fluid flow to the various chambers of the microfluidic device.

In an embodiment, even assay input lines 420 and odd assay input lines 422 are in fluid communication with vias 424 that are aligned with assay input lines 140, which are in fluid communication with assay input ports 122 as illustrated in FIG. 2. In other embodiments, additional assay input lines (not shown) are provided to enable fluid communication between the assay input ports 122 and the assay input lines 420 and 422. Thus, pressurization of the bank of assay input ports 122 will result in flow of the various assays into the illustrated assay input lines. After flowing through the input lines illustrated in FIG. 5B, the various fluids will eventually enter into the unit cells illustrated in FIG. 6.

As discussed above, the various fluid lines can be integrated into the carrier, the microfluidic device, or other suitable structure. In a 48 sample×48 assay array configuration, the 24 even assay input lines 420 will provide inputs to half of the rows of assay input lines 518 shown in FIG. 6. The 24 odd assay input lines 422 will provide inputs to half of the rows of assay inputs lines 518 shown in FIG. 6. Thus, although loading of assays is only illustrated from the right side of the array in FIG. 6, actual implementation will typically load assays from both sides in an even/odd configuration. In some embodiments, additional vias are provide for loading of hydration fluids or the like. Moreover, in some embodiments, in order to provide compatibility with existing carriers, some fluid lines are unused or modified to provide for such compatibility.

The harvesting reagent input line 430 provides for harvesting reagent used in recovering reaction products from the microfluidic device. The harvesting reagent input line 430 illustrated in FIG. 5B is in fluid communication with the harvesting reagent input port 136 illustrated in FIG. 2 and passes along the microfluidic device adjacent to the even assay input lines to the top portion of the device and then branches off into a plurality of harvesting reagent input lines. The harvesting reagent multiplexor has a substantially equal volume for every sample input line to provide uniform pumping during the reaction product recovery operation. It should be noted that the particular branching system illustrated in FIG. 5B is merely provided as an example and other branching systems are included within the scope of the present invention. The harvesting reagent input lines 430 are in fluid communication with sample input lines 516 discussed in relation to FIG. 6. As discussed in relation to FIGS. 9A-D, embodiments utilize a separate harvesting reagent input line for each column of sample chambers, for example, 48 harvesting reagent input lines for an microfluidic device with a 48×48 array configuration. Additionally, although the harvesting reagent input line enters the microfluidic device at a location adjacent the even assay input lines 420, this is not required by embodiments of the present invention and other configurations are within the scope of the present invention. One of ordinary skill in the art would recognize many variations, modifications, and alternatives.

Figure 8A:
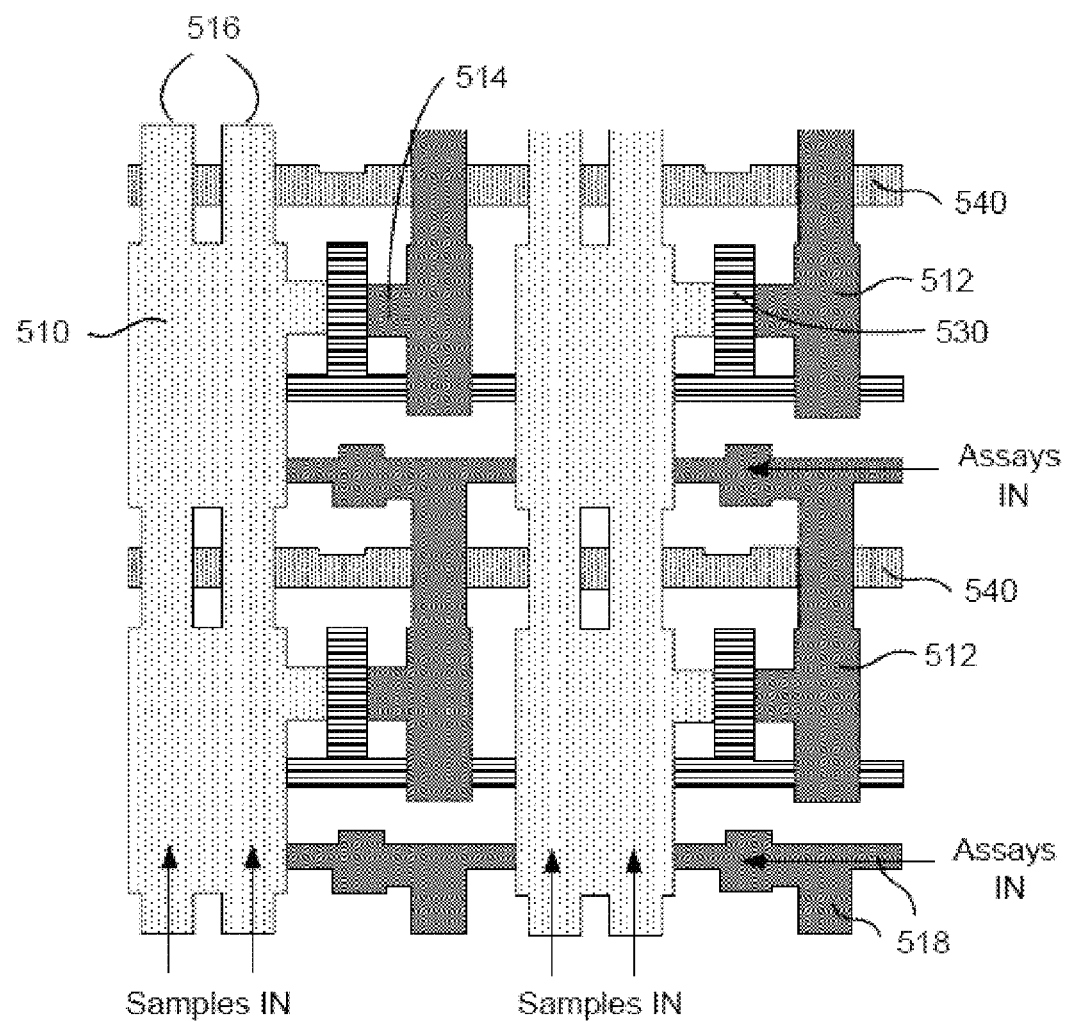
FIGS. 8A-8D are simplified schematic diagrams illustrating fluid flow through unit cells of a microfluidic device that permits recovery of reaction products during operation.
Figure 8B:
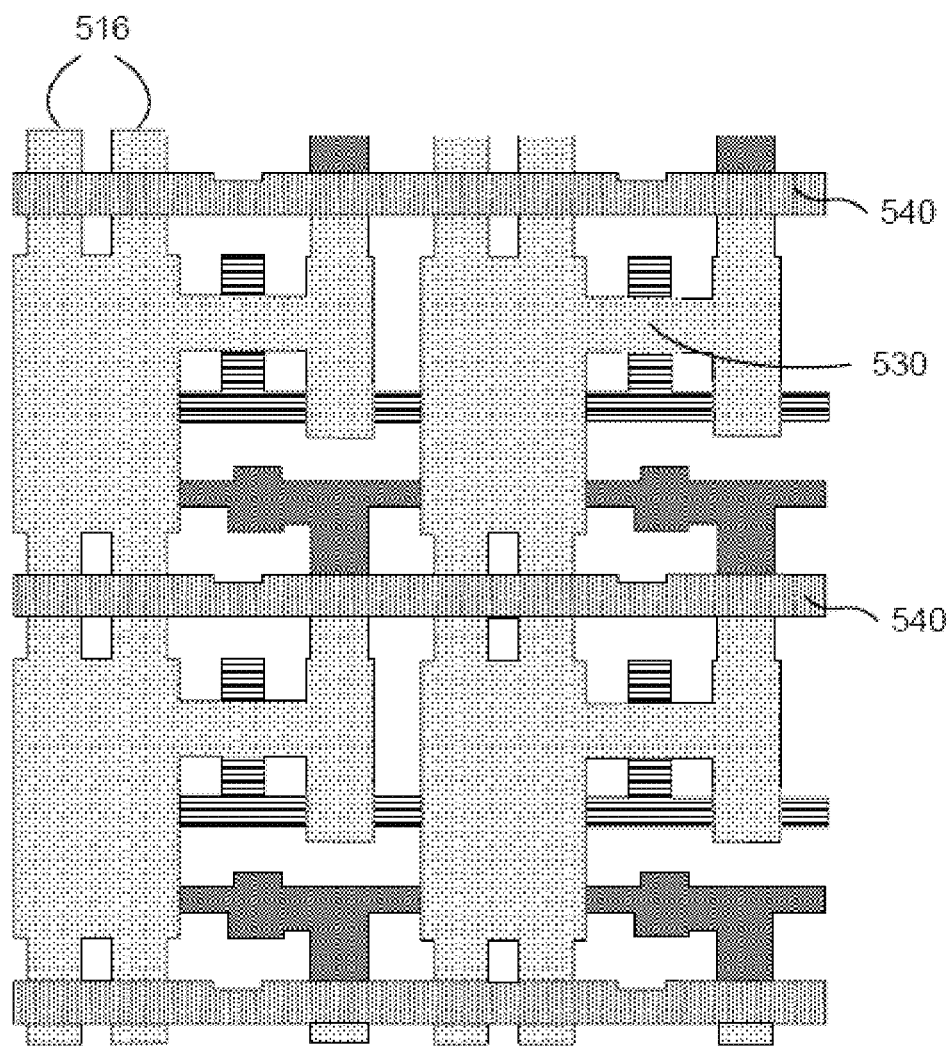
Figure 8C:
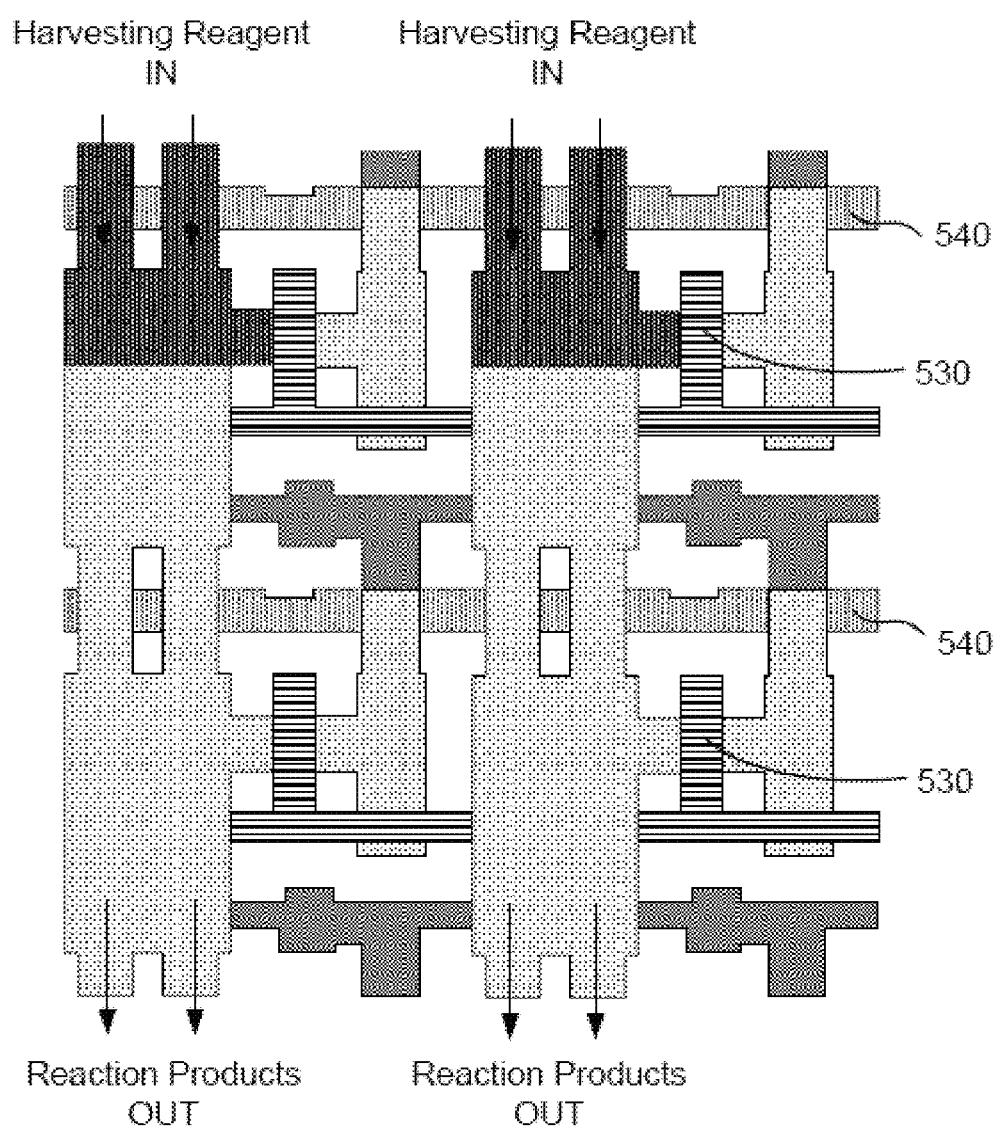

As described in relation to FIG. 8C, harvesting reagent flows from a harvesting reagent input port on the carrier, through the harvesting reagent input lines 430 and into one end of the sample input lines 516. As discussed more fully throughout the present specification, the sample input lines function both as input lines and reaction product recovery lines. For loading, the sample flow path is from the sample input ports 120, through input lines 140, through vias 412, through sample input lines 410, through sample input lines 516, to the reaction chambers 510 and to the loading bowls 830. For reaction product recovery, the product flow path is from the harvesting reagent input port 136, through the harvesting reagent input lines 430, through the sample input lines 516, through the sample input lines 410, through the vias 412, and to the sample input ports 120, which serve during harvesting, as a fluid recovery well. Thus, the use of the term "input" lines should be considered in the context of the particular process being performed, since the "input" lines can serve to both load samples and recover or remove reaction products from the microfluidic device and the carrier.

By applying pressure to the bank of sample input ports 120 and the bank of assay input ports 122, samples and reagents can be loaded through the illustrated sample and assay input lines into sample and assay chambers present in the microfluidic device. By applying pressure to the harvesting reagent input port 136, the reaction products can be recovered from the sample chambers and delivered to the sample input ports. Valves present in the microfluidic device are utilized to control the flow of samples, assays, and reaction products, as described more fully throughout the present specification. FIG. 5B only illustrates a portion of the sample input lines, assay input lines, and harvesting reagent input lines and additional portions of these input lines are illustrated in FIG. 5A and FIG. 6.

FIG. 6 is a simplified schematic diagram of several unit cells of the microfluidic device illustrated in FIG. 5A. In FIG. 6, four unit cells from the array portion 430 shown in FIG. 5A are illustrated for purposes of clarity. The unit cell section of the microfluidic device includes sample chambers 510 and assay chambers 512. Fluid lines 514 provide for fluid communication between the sample chambers and the assay chambers when the interface valves 530 are in the open position. In a specific embodiment, sample input lines 516 are provided in a layer of the microfluidic device underlying the layer containing the sample chambers. In a similar manner, assay input lines 518 are provided in a layer of the microfluidic device underlying the layer containing the assay chambers. Samples flow from the sample input lines 410 illustrated in FIG. 5B to sample input lines 516 and up through one or more vias passing from the sample input lines to the sample chambers. Although two sample lines are illustrated for each sample chambers, this particular number is not required by the present invention and other numbers of sample input lines, for example, 1 input line, 3, 4, or more than 4 sample input lines may be utilized. The sample input lines 516 provide a continuous flow path in the column direction of the figure, enabling a single sample to be distributed evenly among multiple sample chambers.

FIG. 6 illustrates assay input lines 518, which provide for assay flow from assay input lines 420 and 422 illustrated in FIG. 5B to the assay chambers 512. Although FIG. 6 only illustrates assay input lines entering the unit cells from the right side of the figure, it will be evident to one of skill in the art that in the implementation illustrated in FIG. 5B, even and odd assays are loaded from opposing sides of the microfluidic device. The illustration provided in FIG. 6 is merely simplified for purposes of clarity. In a specific embodiment, the assays load through vias connecting the input lines and the assay chambers in a manner similar to the filling of the sample chambers. The loading of assays along the rows of the microfluidic device provide a different assay for each of the samples, resulting in a number of pairwise combinations appropriate for an M×N array.

As described more fully throughout the present specification, reaction products are recovered from the microfluidic device using the sample input lines 516 and pumps (not shown). Containment valves 540 provide for containment between the various sample and assay chambers in each row. Utilizing the interface valves 530 and the containment valves 540, each of the sample chambers can be isolated from each of the other sample chambers as well as the assay chambers. The assay chambers can be isolated from the other assay chambers using the containment valves. Both the isolation and containment valves are actuated by application of pressure to a corresponding control line in fluid communication with sources 130-134 or by other means, for example, electrostatic actuation.

In FIG. 6, four sample chambers 510 are illustrated in an array configuration. The four illustrated chambers are merely shown by way of example and implementations of the present invention are not limited to the four illustrated chambers, but typically provide 2,304 chambers in a 48×48 array configuration, 4,096 chambers in a 64×64 array configuration, 9,216 chambers in a 96×96 array configuration, or the like.

Embodiments of the present invention provide unit cells with dimensions on the order of several hundred microns, for example unit cells with dimension of 500×500 µm, 525×525 µm, 550×550 µm, 575×575 µm, 600×600 µm, 625×625 µm, 650×650 µm, 675×675 µm, 700×700 µm, or the like. The dimensions of the sample chambers and the assay chambers are selected to provide amounts of materials sufficient for desired processes while reducing sample and assay usage. As examples, sample chambers can have dimensions on the order of 100-400 µm in width×200-600 µm in length×100-500 µm in height. For example, the width can be 100 µm, 125 µm, 150 µm, 175 µm, 200 µm, 225 µm, 250 µm, 275 µm, 300 µm, 325 µm, 350 µm, 375 µm, 400 µm, or the like. For example, the length can be 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, or the like. For example, the height can be 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, or the like. Assay chambers can have similar dimensional ranges, typically providing similar steps sizes over smaller ranges than the smaller chamber volumes. In some embodiments, the ratio of the sample chamber volume to the assay chamber volume is about 5:1, 10:1, 15:1, 20:1, 25:1, or 30:1. Smaller chamber volumes than the listed ranges are included within the scope of the invention and are readily fabricated using microfluidic device fabrication techniques.

Higher density microfluidic devices will typically utilize smaller chamber volumes in order to reduce the footprint of the unit cells. In applications for which very small sample sizes are available, reduced chamber volumes will facilitate testing of such small samples.

The dimensions of the interface valves 530 are selected to provide for complete obstruction of the fluid lines 514 connecting the sample and assay chambers. In some embodiments, the valve dimensions range from about 10-200 μm×10-200 μm, for example, 50×50 μm, 50×65 μm, 50×80 μm, 50×100 μm, 65×50 μm, 65×65 μm, 65×80 μm, 65×100 μm, 80×50 μm, 80×65 μm, 80×80 μm, 80×100 μm, 100×50 μm, 100×65 μm, 100×80 μm, 100×100 μm, or the like. The sample input lines may have various widths depending on the number of sample input lines and the sample chamber volumes, and desired flow rates for loading and product recovery. As examples, the sample input lines may have a cross-section of 1-20 μm in height and 50-100 μm in width. For example, the sample input lines may have heights of 1, 2, 3, 4, 5, 6, 7, 8, 9, 10, 11, 12, 13, 14, 15, 16, 17, 18, 19, or 20 μm and widths of 50, 55, 60, 65, 70, 75, 80, 85, 90, 95, or 100 μm.

Other device parameters, including layer to layer alignment, ranging from 20-100 μm, and via size, ranging from 50-200 microns, are selected to provide desired system performance characteristics. One of ordinary skill in the art would recognize many variations, modifications, and alternatives.

In some embodiments, an extra assay inlet is provided at the side of the microfluidic device adjacent the harvesting reagent input lines. Additionally, no assay inlet is provided at the side of the microfluidic device adjacent the sample input ports on the carrier. In this configuration, the extra assay inlet can be used for dehydration chamber loading. Typically, loading of the dehydration chambers will use more than 5 μl of assay solution. Alternatively, a separate dehydration solution could be used to keep assay volumes uniform across the microfluidic device.

Figure 7:
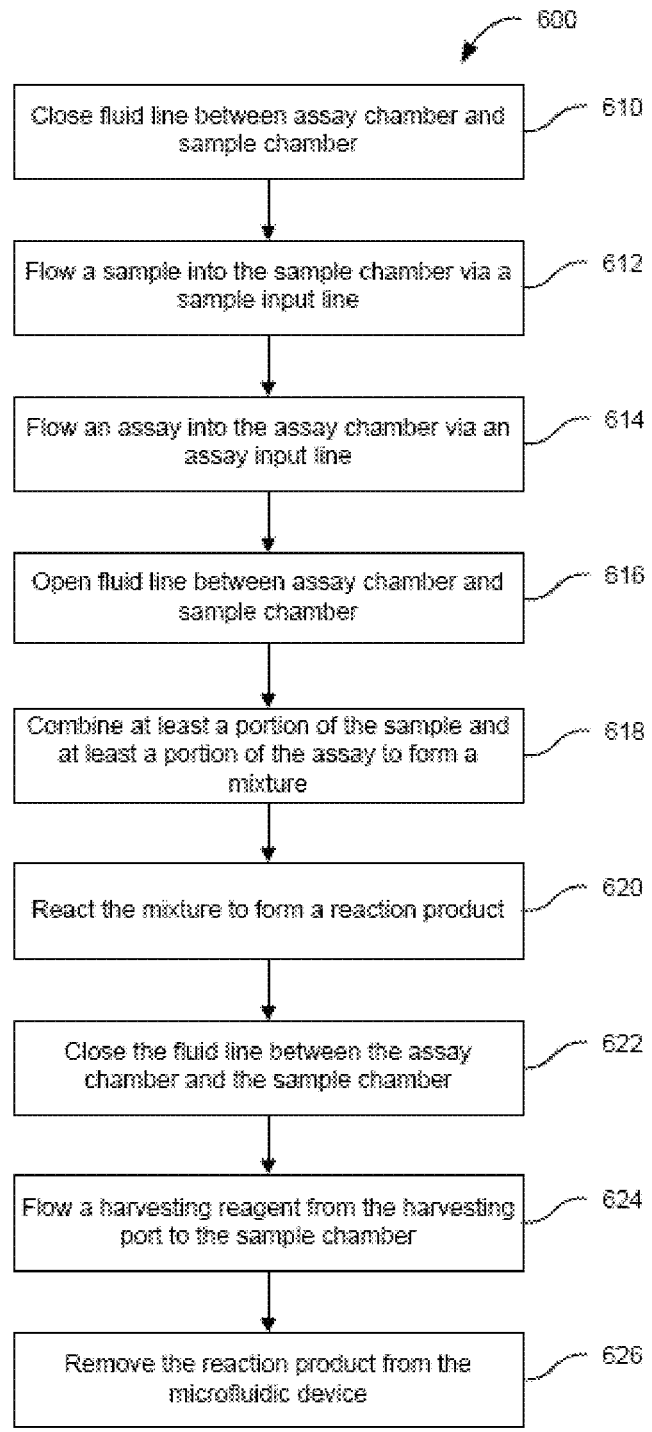
FIG. 7 is a simplified flowchart of a method of operating a microfluidic device that permits recovery of reaction products.

FIG. 7 is a simplified flowchart of a method of operating a microfluidic device according to an embodiment of the present invention. In the illustrated embodiment, the microfluidic device includes at least one assay chamber, at least one sample chamber, and at least one harvesting port. In a particular embodiment, the microfluidic device includes a plurality of assay chambers and a plurality of sample chambers. The method 600 includes closing a fluid line between the assay chamber and the sample chamber (610). Referring to FIG. 6, interface valves 530 are operable to close fluid lines 514 passing between the sample chambers 510 to the assay chambers 512. In some embodiments, the interface valves 530 are "push-up" valves as described more fully below. The interface valves are formed by the intersection of control line 532 or control channel that is at least partially contained in a first layer of the microfluidic device. The fluid lines are at least partially contained in a second layer of the microfluidic device. The control lines 532 are in fluid communication with one or more pressure actuators or accumulators as illustrated in FIG. 2.

The intersection of the control line 532 with the fluid line 514 forms a valve at the intersection, referred to as an interface valve 530 because the valve prevents mixing at the interface between the sample and the assay. The interface valve 530 is actuated in response to fluid pressure in the control line and is operative to prevent fluid flow through the fluid lines. Generally, the multilayer microfluidic device discussed herein includes a number of elastomeric layers and the valves 530 include a deflectable membrane between the first layer and the second layer. In a "push-up" configuration, the deflectable membrane of the valve is deflectable into the fluid line 514 positioned above the intersection with the control line 532. In this configuration, the deflectable membrane deflects up into the fluid line to close the fluid line at the position of the valve, thus the reference to "push-up" valves. Releasing the pressure in the control line will result in the deflectable membrane returning to the undeflected position and thereby opening of the closed valve. Additional description of microfluidic devices including valves is provided in U.S. Patent Application No. 2005/0226742, the entire disclosure of which is hereby incorporated by reference in its entirety for all purposes.

As illustrated in FIG. 6, actuation of control lines 532 will obstruct fluid lines 514. Typically, the control lines 532 are actuated concurrently by application of pressure to a pressure accumulator. Referring once again to FIG. 7, after closing of the interface valves 530, samples flow into sample chambers 510 via sample input lines 516 (612). As illustrated in FIG. 6, each sample chamber 510 is in fluid communication with multiple (e.g., two) sample input lines 516. In other embodiments, other numbers of sample input lines can be utilized. One of ordinary skill in the art would recognize many variations, modifications, and alternatives. Typically, the sample input lines, which are at least partially contained in a second layer of the microfluidic device, pass under the sample chambers, which are at least partially contained in a third layer of the microfluidic device. A via (not illustrated) passing from the sample input line up to the sample chamber, provide for fluid flow from the sample input line to the sample chamber. As shown in FIG. 6, samples flow in, for example, up the columns, past containment valves 540, which are open, through the vias extending out of the plane of the figure, and into the various sample chambers. Fluids such as air present in the sample chambers are expelled during loading of the samples as a result of the permeability of the elastomeric material used to fabricate the microfluidic device.

Referring once again to FIG. 7, assays flow into assay chambers 512 via assay input lines 518 (614). The assays flow through assay input lines 518, past containment valves 540, which are open, and through vias (not shown) passing from the assay input lines to the assay chambers. The closure of the interface valves 530 prevent the samples in the sample chambers and the assays in the assay chambers from mixing. Once the sample and assay are loaded, the fluid line between the assay chamber and the sample chamber is opened (616). In embodiments of the present invention, multiple fluid lines 514 are opened concurrently by opening of interface valves 530. At least a portion of the sample and at least a portion of the assay are combined to form a mixture (618). The mixture of the sample and assay is formed throughout the sample and assay chambers as well as the fluid lines connecting these chambers. Free interface diffusion is a process in which mixing is slow and the rate of species equilibration depends on the species' diffusion constants. Small molecules such as salts have large diffusion constants, and hence equilibrate quickly. Large molecules (e.g., proteins) have small diffusion constants, and equilibrate more slowly.

The mixture is reacted to form a reaction product (620). A typical reaction included within the scope of the present invention is PCR, which involves thermocycling of the microfluidic device through a number of cycles as will be evident to one of skill in the art. The fluid line between the assay chamber and the sample chamber is closed (622) by actuation of interface valves 530. Closure of the interface valves separates the reaction product present in the sample chambers from the reaction products present in the assay chambers. Additionally, the containment valves 540 can be closed during thermocycling in order to prevent precipitation during the thermocycling process. A harvesting reagent flows from the harvesting port to the sample chamber (624) in order to begin the process of harvesting the reaction products present in the sample chambers. The harvesting port 136 is an example of a fluid input port useful in the harvesting process. As illustrated in FIG. 4, the reaction products flow down through the sample input lines 516 toward the sample input ports from which the samples were originally provides. Thus, in the illustrated method, removing the reaction products from the microfluidic device includes flowing the reaction products through at least a portion of the sample input line that was used to load the samples to the sample input port. Thus, the reaction product are removed from the microfluidic device (626) and output to the sample input ports, for example, sample input ports 120 illustrated in FIG. 2.

Dilation pumping is used in the illustrated embodiment to remove the reaction products from the microfluidic device as discussed in additional detail in relation to FIGS. 9A-D. Referring once again to FIG. 2, control ports 130 and 132 or pressure accumulators 150 and 152 can be used to actuate the valves used in dilation pumping. Thus, embodiments provide valves for dilation pumping on the microfluidic device, which provides for removal of the reaction products from the microfluidic device. This contrasts with conventional designs in which such valves were not provided as part of the microfluidic device.

It should be appreciated that the specific steps illustrated in FIG. 7 provide a particular method of operating a microfluidic device according to an embodiment of the present invention. Other sequences of steps may also be performed according to alternative embodiments. For example, alternative embodiments of the present invention may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. One of ordinary skill in the art would recognize many variations, modifications, and alternatives.

FIGS. 8A-8D are simplified schematic diagrams illustrating fluid flow through unit cells of a microfluidic device during operation according to an embodiment of the present invention. Referring to FIG. 8A, the microfluidic device is illustrated during the sample and assay loading process. Containment valves 540 are open, allowing fluid flow along the sample input lines 516 to the various sample chambers 510. The open state of the containment valves also enables the assays to flow in through the assay input lines 518 to the various assay chambers 512. Using a single sample for each set of sample input lines (m of M samples) enables loading of a single sample in each column of sample chambers. Additionally, using a single assay for each assay input line (n of N assays) enables loading of a single assay in each row of assay chambers. The closed state of the interface valves 530 prevent mixing of the samples and the assays.

FIG. 8B illustrates the microfluidic device during a sample and assay mixing process as well as a subsequent reaction process (e.g., amplification). The containment valves 540 are closed, preventing fluid flow along the sample input lines 516. The closure of the containment valves thus isolates the sample chambers along a column from one another (with each column potentially containing a different sample). The closing of the containment valves 540 additionally isolates the assay chambers from other assay chambers in each row. After this chamber isolation is provided, the interface valves 530 are opened, enabling the samples and assays to mix via free interface diffusion (FID) and form M×N pairwise combinations. Although the materials in the pairs of sample/assay chambers are illustrated with the same shading in FIG. 8B, it will be appreciated that four different pairwise combinations are illustrated, one for each pair of sample/assay chambers. The multiple steps involved in mixing the samples and assays, then performing PCR amplification, are represented by a single drawing in FIG. 8B although it will be apparent to one of skill in the art that numerous steps, for example, multiple thermocycling steps, are involved in these processes.

FIG. 8C illustrates the microfluidic device during sample chamber isolation and initial loading of the harvesting reagent. The interface valves 530 are closed to maintain isolation between the sample chambers and the assay chambers. Thus, the reaction products present in the sample chambers are recovered while the reaction products in the assay chambers are not recovered. The containment valves 540 are opened to allow the harvesting reagent to flow into the sample input lines 516 from the harvesting reagent input lines 430 illustrated in FIG. 5B. The harvesting reagent flows through the sample input lines, and into the sample chambers. In the illustrated embodiment, the reaction products are removed as the harvesting reagent flows through the sample input lines and the sample chambers in response to a dilation pumping process described in additional detail in relation to FIGS. 9A-9D. As illustrated in FIG. 8C, the harvesting reagent has only reached the middle region of the upper reaction chambers. As the dilation pumping process continues, the harvesting reagent will be progressively introduced into subsequent sample chambers, thereby displacing the reaction products. Eventually, the reaction products associated with each sample will be recovered as a pooled fluid including the reaction products and the harvesting reagent in the sample input port from which the sample was originally dispensed.

It should be noted that the straight line representing the interface between the harvesting reagent and the reaction products is shown merely for purposes of simplicity and it will be apparent to one of skill in the art that in practice, a more complicated interface will be present.

Figure 8D:
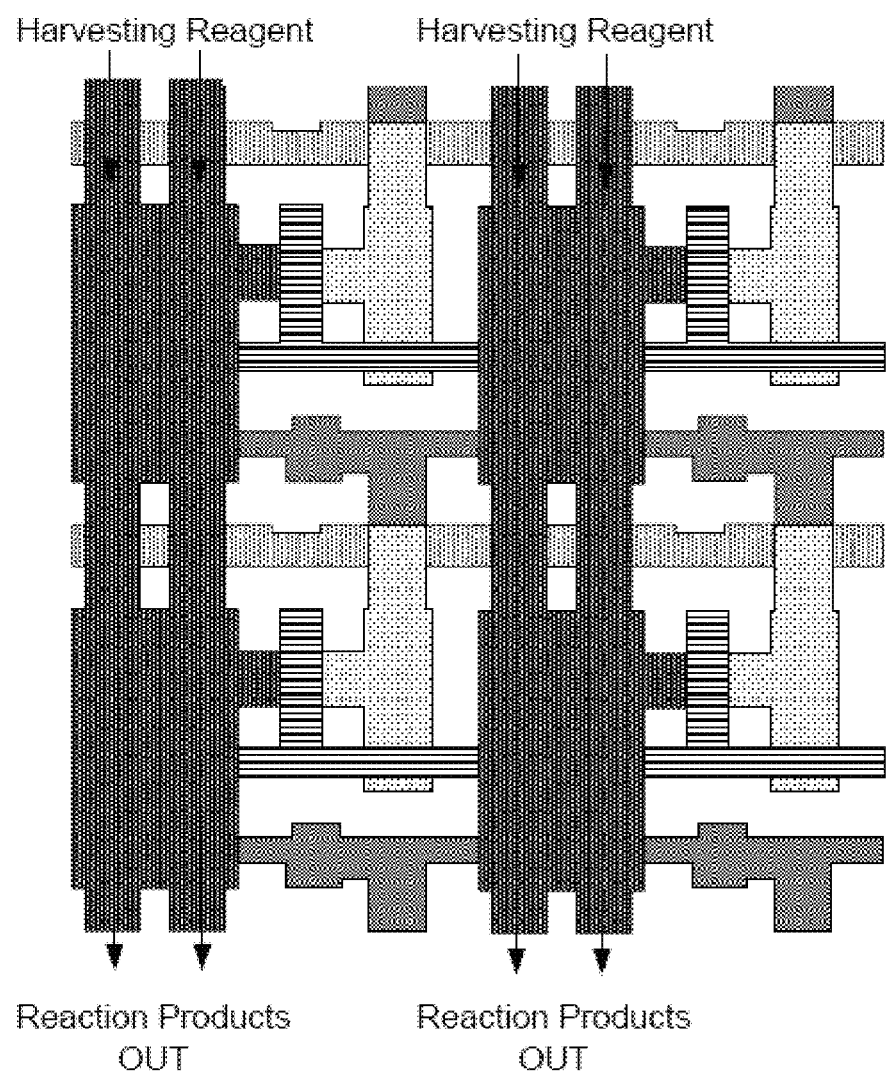

FIG. 8D illustrates the microfluidic device during final loading of the harvesting reagent and recovery of the reaction products. As the dilation pumping process continues, harvesting reagent is introduced into additional sample chambers progressively farther from the harvesting reagent input lines. The state of the recovery process illustrated in FIG. 8D shows that the reaction products have been flushed from the sample chambers, which are now filled with harvesting reagent. Although only four sample chambers are illustrated in FIG. 8D, it will be appreciated that recovery of the reaction products from all the sample chambers in the array is provided by the embodiments described herein.

FIGS. 9A-9D are simplified schematic diagrams illustrating fluid flow through a microfluidic device during operation according to an embodiment of the present invention. FIG. 9A illustrates a portion of a microfluidic device according to an embodiment of the present invention during loading of samples and assays. The illustrated portion includes a harvesting reagent input line 810, vent and loading bowl portions 830, and isolation valve 840. As described more fully throughout the present specification, valves 820 and 822 are used to perform dilation pumping of reaction products present in sample chambers 510. As illustrated in FIG. 9A, valve 820 is closed and valve 822 is open. Valves

820 and 822 are typically "push-up" valves described elsewhere in the present specification.

Samples are loaded into sample chambers 510 and assays are loaded into assay chambers 512 as described in relation to FIG. 6. Interface valves 530 are closed, preventing mixing of the samples and assays. Vents and loading bowls are provided in some embodiments to allow for reductions in effects related to depletion fronts. The inventors have observed that in loading samples into microfluidic devices (e.g., through the vertical sample input lines illustrated in FIG. 9A), binding of a portion of the sample present at the leading edge of the flow path to the material of the microfluidic device will produce a depletion front in which one or more components of the sample are depleted as a result of this binding process. The provision of the vents and loading bowls 830 enables the user to push the depletion front through the various sample chambers of the microfluidic device and store the depleted sample material in the loading bowls 830. Eventually, as the depleted sample material is flushed through the device into the loading bowls, the sample contained in the microfluidic device will be substantially undepleted.

Isolation valve 840 is open during the sample and assay loading process to enable the depletion front to flow into the loading bowls 830. Valve 822 is open, allowing the samples to flow through the sample input lines to the various sample chambers. Since valve 820 is closed, samples are not allowed to pass into the harvesting reagent input line 810. It should be noted that containment valves 540 are illustrated in the closed state in FIG. 9A. Containment valves are open during sample and assay loading and then are closed as illustrated after sample and assay loading is complete. The containment valves isolate the various pairs of reaction and assay chambers from other pairs containing the various pairwise combinations.

In FIG. 9A, only a single column of the microfluidic device is illustrated for purposes of clarity. It is understood that additional columns are provided by the microfluidic devices as illustrated, for example, in FIG. 6. Moreover, much of the column is not illustrated for the purposes of clarity. The two sets of sample/assay chambers illustrated are those at the top and bottom of FIG. 4A, respectively. The set adjacent valve 820 is the topmost set and the set adjacent valve 822 is the bottommost set. Thus, these diagrams are merely representative and not intended to limit the scope of the present invention.

FIG. 9B illustrates mixing of the samples and assays and a subsequent reaction (e.g., amplification) process. In order to mix the samples and reagents, interface valves 530 are placed in the open position as shown. Closure of containment valves 540 seals the reaction products in the sample and assay chambers along with the connecting fluid lines. As illustrated in FIG. 9B, isolation valve 840 is closed, preventing fluid flow between the sample input lines and the loading bowls 830. Actuation of valve 840 to place it in the open or closed position is performed using a pressure accumulator (not shown) in some embodiments and using other actuation techniques in other embodiments, for example, mechanical, electrostatic, electromechanical, thermodynamic, piezoelectric, or the like. Such additional techniques may also be applicable to other valves described herein. One of ordinary skill in the art would recognize many variations, modifications, and alternatives.

Although FIG. 9B illustrates mixing and reaction using a single image, one of skill in the art will appreciate that multiple thermal cycles may be used to amplify DNA using the PCR process. Thus, this simple figure is intended to show mixing and subsequent reactions that can occur in the microfluidic device.

FIG. 9C illustrates a portion of the microfluidic device in a first stage of a reaction product harvesting process. A harvesting reagent flows from a harvesting port as illustrated in FIG. 5A through harvesting reagent input line 810 toward the sample chambers. As shown in FIG. 9A, valve 820 is open, allowing the harvesting reagent to flow into the topmost sample chamber. Closure of the interface valves 530 prevents the harvesting reagent from flowing into the assay chambers, which also contain reaction products. The extent to which the harvesting reagent initially fills the sample input lines and sample input chambers is limited by the closure of valve 822. As illustrated, the harvesting reagent has only partially filled a portion of the first sample chamber. The illustration of a side of the sample chamber being filled with harvesting reagent is merely provided by way of example, since the flow of the harvesting reagent into the sample chamber is actually through vias extending from the plane of the figure. Closure of isolation valve 840 prevents harvesting reagent from flowing into the loading bowls, although other embodiments may enable such a flow if desired.

Fluid pressure resulting from the flow of the harvesting reagent into the array portion of the microfluidic device results in expansion of the sample input lines and sample chambers above the valve 822. The pump cycle is initiated by this pressurization of the sample chambers. As described below, closing of valve 820 and opening of valve 822 will enable the pressurized harvesting reagent and reaction products to be recovered from the microfluidic device as it flows through the microfluidic device.

FIG. 9D illustrates a portion of the microfluidic device in a second stage of the reaction product harvesting process. Although a second stage is illustrated, this is not intended to imply that the second stage immediately follows the first stage. As described below, the second stage is typically separated from the first stage by one or more intermediate stages of dilation pumping.

Dilation pumping (also know as volumetric capacitive pumping) is a method of operating a properly configured integrated fluidic circuit (microfluidic device) to obtain precise, low rate, low volume pumping through all configured elements of the microfluidic device. Dilation pumping is unique to microfluidic circuits that utilize channels that have one or more channel walls formed from an elastomeric material. As an example, the flow of the harvesting reagent through the sample input lines and sample chambers is considered volumetric capacitive pumping. Pumping proceeds by the closure of valves 822 and the opening of valves 820. As discussed above, harvesting reagent ports (not illustrated) are pressurized to introduce the harvesting reagent into the topmost sample input lines and sample chambers, which can be considered as a channel. The pressurization of microfluidic channels with at least one channel wall formed from an elastomeric material results in expansion of the elastomeric wall(s) outward from the channel with a resulting increase in channel volume that is proportional to the fluidic pressure (or gaseous pressure in alternate embodiments) within the channel, the elastic properties of the elastomeric channel wall material such as Young's modulus, and the length and cross sectional area of the channel. The sample input lines and sample chambers are allowed to pressurize and then valves 820 is closed as illustrated in FIG. 9D. Following closure of valves 820, valves 822 are opened. The pumped volume through the sample input lines and the sample chambers is equal to the expanded volume of the channel when under pressure minus the native volume of the channel when pressure is released and the expanded elastomeric channel wall(s) is allow to relax. Dilation pumping is continued through repetitive cycles of closing 822, opening 820, pressurizing the sample input lines and sample chambers, closing 820, and opening 822. In this manner, continuous or discontinuous low volume pumping may be accomplished at precisely controlled flow rates.

Thus embodiments provide a method of dilation pumping that includes closing a first valve disposed between the sample chamber and the sample input port (i.e., valve 822), opening a second valve disposed between the harvesting port and the sample chamber (i.e., valve 820), closing the second valve, opening the first valve, and repeating these steps a predetermined number of times. Between the steps of opening the second valve and closing the second valve, the harvesting reagent flows into the sample input lines and sample chambers, pressurizing the channel as described above. After the dilation pumping process is complete, harvesting reagent substantially fills the sample input lines and sample chambers (e.g., recovery rates>95%), thereby pooling the reaction products associated with a given sample in the sample input port from which the given sample was initially dispensed.

Dilation pumping provides benefits not typically available using conventional techniques. For example, dilation pumping enables for a slow removal of the reaction products from the microfluidic device. In an exemplary embodiment, the reaction products are recovered at a fluid flow rate of less than 100 µl per hour. In this example, for 48 reaction products distributed among the reaction chambers in each column, with a volume of each reaction product of about 1.5 µl, removal of the reaction products in a period of about 30 minutes, will result in a fluid flow rate of 72 µl/hour. (i.e., 48*1.5/0.5 hour). In other embodiments, the removal rate of the reaction products is performed at a rate of less than 90 µl/hr, 80 µl/hr, 70 µl/hr, 60 µl/hr, 50 µl/hr, 40 µl/hr, 30 µl/hr, 20 µl/hr, 10 µl/hr, 9 µl/hr, less than 8 µl/hr, less than 7 µl/hr, less than 6 µl/hr, less than 5 µl/hr, less than 4 µl/hr, less than 3 µl/hr, less than 2 µl/hr, less than 1 µl/hr, or less than 0.5 µl/hr.

Dilation pumping results in clearing of substantially a high percentage and potentially all the reaction products present in the microfluidic device. Some embodiments remove more than 75% of the reaction products present in the reaction chambers (e.g., sample chambers) of the microfluidic device. As an example, some embodiments remove more than 80%, 85%, 90%, 92%, 95%, 96%, 97%, 98%, or 99% of the reaction products present in the reaction chambers.

In some embodiments, a harvesting valve is provided on the microfluidic device to obstruct the flow of harvesting reagent through the device. Application of a pressure source to a harvesting input port results in flow of harvesting fluid (e.g., a harvesting liquid) through harvest reagent input lines up to the harvesting valve. The permeability of the materials utilized to fabricate the microfluidic device enables such a harvesting fluid to fill the harvest reagent input lines, typically expelling air initially present in such lines. The presence of the harvesting valve will obstruct the flow of the harvest reagent at the location of the harvesting valve. Actuation (i.e., opening) of the harvesting valve will result in the harvesting fluid flowing through the harvest reagent input lines downstream of the harvesting valve. In other embodiments, a harvesting valve is replaced with one or more other suitable valves as appropriate to the particular application. For example, in the embodiment illustrated in FIGS. 9A-9D, valve 820 serves to prevent flow of harvesting reagent until the dilation pumping process is initiated.

Fabrication methods using elastomeric materials and methods for design of devices and their components have been described in detail in the scientific and patent literature. See, e.g., Unger et al. (2000) Science 288:113-116; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic systems including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 2002/0164816; 2002/0127736; and 2002/0109114; PCT Publication Nos. WO 2005/084191; WO 05/030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23, Hong et al, 2004, "A nanoliter-scale nucleic acid processor with parallel architecture" Nature Biotechnology 22:435-39.

According to certain embodiments describer herein, the detection and/or quantification of one or more target nucleic acids from one or more samples may generally be carried out on a microfluidic device by obtaining a sample, optionally pre-amplifying the sample, and distributing the optionally pre-amplified sample, or aliquots thereof, into reaction chambers of a microfluidic device containing the appropriate buffers, primers, optional probe(s), and enzyme(s), subjecting these mixtures to amplification, and querying the aliquots for the presence of amplified target nucleic acids. The sample aliquots may have a volume of less than 1 picoliter or, in various embodiments, in the range of about 1 picoliter to about 500 nanoliters, in a range of about 2 picoliters to about 50 picoliters, in a range of about 5 picoliters to about 25 picoliters, in the range of about 100 picoliters to about 20 nanoliters, in the range of about 1 nanoliter to about 20 nanoliters, and in the range of about 5 nanoliters to about 15 nanoliters. In many embodiments, sample aliquots account for the majority of the volume of the amplification mixtures. Thus, amplification mixtures can have a volume of less than 1 picoliter or, in various embodiments about 2, about 5 about 7, about 10, about 15, about 20, about 25, about 50, about 100, about 250, about 500, and about 750 picoliters; or about 1, about 2, about 5, about 7, about 15, about 20, about 25, about 50, about 250, and about 500 nanoliters. The amplification mixtures can also have a volume within any range bounded by any of these values (e.g., about 2 picoliters to about 50 picoliters).

In certain embodiments, multiplex detection is carried out in individual amplification mixture, e.g., in individual reaction chambers of a microfluidic device, which can be used to further increase the number of samples and/or targets that can be analyzed in a single assay or to carry out comparative methods, such as comparative genomic hybridization (CGH). In various embodiments, up to 2, 3, 4, 5, 6, 7, 8, 9, 10, 50, 100, 500, 1000, 5000, 10000 or more amplification reactions are carried out in each individual reaction chamber.

In specific embodiments, the assay usually has a dynamic range of at least 3 orders of magnitude, more often at least 4, at least 5, at least 6, at least 7, or at least 8 orders of magnitude.

Quantitative Real-Time PCR and Other Detection and Quantification Methods

Any method of detection and/or quantification of nucleic acids can be used in the invention to detect amplification products. In one embodiment, PCR (polymerase chain reaction) is used to amplify and/or quantify target nucleic acids. In other embodiments, other amplification systems or detection systems are used, including, e.g., systems described in U.S. Pat. No. 7,118,910 (which is incorporated herein by reference in its entirety for its description of amplification/detection systems) and Invader assays; PE BioSystems). In particular embodiments, real-time quantification methods are used. For example, "quantitative real-time PCR" methods can be used to determine the quantity of a target nucleic acid present in a sample by measuring the amount of amplification product formed during the amplification process itself Fluorogenic nuclease assays are one specific example of a real-time quantification method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TaqMan® method." See U.S. Pat. No. 5,723,591; Heid et al., 1996, Real-time quantitative PCR Genome Res. 6:986-94, each incorporated herein by reference in their entireties for their descriptions of fluorogenic nuclease assays. It will be appreciated that while "TaqMan® probes" are the most widely used for qPCR, the invention is not limited to use of these probes; any suitable probe can be used.

Other detection/quantification methods that can be employed in the present invention include FRET and template extension reactions, molecular beacon detection, Scorpion detection, Invader detection, and padlock probe detection.

FRET and template extension reactions utilize a primer labeled with one member of a donor/acceptor pair and a nucleotide labeled with the other member of the donor/acceptor pair. Prior to incorporation of the labeled nucleotide into the primer during a template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the "stem-loop" format and the "duplex" format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time, the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., *Advances in Nucleic Acid and Protein Analysis* 3826:117-125, 2000) and U.S. Pat. No. 6,706,471.

Padlock probes (PLPs) are long (e.g., about 100 bases) linear oligonucleotides. The sequences at the 3' and 5' ends of the probe are complementary to adjacent sequences in the target nucleic acid. In the central, noncomplementary region of the PLP there is a "tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by the action of an exonuclease. Hybridization and ligation of a PLP requires that both end segments recognize the target sequence. In this manner, PLPs provide extremely specific target recognition.

The tag regions of circularized PLPs can then be amplified and resulting amplicons detected. For example, Taq-Man® real-time PCR can be carried out to detect and quantify the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8.

In particular embodiments, fluorophores that can be used as detectable labels for probes include, but are not limited to, rhodamine, cyanine 3 (Cy 3), cyanine 5 (Cy 5), fluorescein, Vic™, Liz™., Tamra™, 5-Fam™, 6-Fam™, and Texas Red (Molecular Probes). (Vic™, Liz™, Tamra™, 5-Fam™, 6-Fam™ are all available from Applied Biosystems, Foster City, Calif.).

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928, 907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in "real-time." In certain embodiments, one can use the amount of amplification product and number of amplification cycles to calculate how much of the target nucleic acid sequence was in the sample prior to amplification.

According to some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid.

According to certain embodiments, one can employ an internal standard to quantify the amplification product indicated by the fluorescent signal. See, e.g., U.S. Pat. No. 5,736,333.

In various embodiments, employing preamplification, the number of preamplification cycles is sufficient to add one or more nucleotide tags to the target nucleotide sequences, so that the relative copy numbers of the tagged target nucleotide sequences is substantially representative of the relative copy numbers of the target nucleic acids in the sample. For example, preamplification can be carried out for 2-20 cycles to introduce the sample-specific or set-specific nucleotide tags. In other embodiments, detection is carried out at the end of exponential amplification, i.e., during the "plateau" phase, or endpoint PCR is carried out. In this instance, preamplification will normalize amplicon copy number across targets and across samples. In various embodiments, preamplification and/or amplification can be carried out for about: 2, 4, 10, 15, 20, 25, 30, 35, or 40 cycles or for a number of cycles falling within any range bounded by any of these values.

Labeling Strategies

Any suitable labeling strategy can be employed in the methods of the invention. Where the assay mixture is aliquoted, and each aliquot is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR Green, Pico Green (Molecular Probes, Inc., Eugene, Oreg.), Eva Green (Biotinum), ethidium bromide, and the like (see Zhu et al., 1994, *Anal. Chem.* 66:1941-48). Suitable universal qPCR probes also include sequence-specific probes that bind to a nucleotide sequence present in all amplification products. Binding sites for such probes can be conveniently introduced into the tagged target nucleic acids during amplification.

Alternatively, one or more target-specific qPCR probes (i.e., specific for a target nucleotide sequence to be detected) is employed in the amplification mixtures to detect amplification products. Target-specific probes could be useful, e.g., when only a few target nucleic acids are to be detected in a large number of samples. For example, if only three targets were to be detected, a target-specific probe with a different fluorescent label for each target could be employed. By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers prior to carrying out the amplification steps described herein.

In certain embodiments, the concentration of undesired components can be reduced by simple dilution. For example, preamplified samples can be diluted about 2-, 5-, 10-, 50-, 100-, 500-, 1000-fold prior to amplification to improve the specificity of the subsequent amplification step.

In some embodiments, undesired components can be removed by a variety of enzymatic means. Alternatively, or in addition to the above-described methods, undesired components can be removed by purification. For example, a purification tag can be incorporated into any of the above-described primers (e.g., into the barcode nucleotide sequence) to facilitate purification of the tagged target nucleotides.

In particular embodiments, clean-up includes selective immobilization of the desired nucleic acids. For example, desired nucleic acids can be preferentially immobilized on a solid support. In an illustrative embodiment, an affinity moiety, such as biotin (e.g., photo-biotin), is attached to desired nucleic acid, and the resulting biotin-labeled nucleic acids immobilized on a solid support comprising an affinity moiety-binder such as streptavidin. Immobilized nucleic acids can be queried with probes, and non-hybridized and/or non-ligated probes removed by washing (See, e.g., Published P.C.T. Application WO 03/006677 and U.S. Ser. No. 09/931,285.) Alternatively, immobilized nucleic acids can be washed to remove other components and then released from the solid support for further analysis. This approach can be used, for example, in recovering target amplicons from amplification mixtures after the addition of primer binding sites for DNA sequencing. In particular embodiments, an affinity moiety, such as biotin, can be attached to an amplification primer such that amplification produces an affinity moiety-labeled (e.g., biotin-labeled) amplicon. Thus, for example, where three primers are employed to add barcode and nucleotide tag elements to a target nucleotide sequence, as described above, at least one of the barcode or reverse primers can include an affinity moiety. Where four primers (two inner primers and two outer primers) are employed to add desired element to a target nucleotide sequence, at least one of the outer primers can include an affinity moiety.

Data Output and Analysis

In certain embodiments, when the methods of the invention are carried out on a matrix-type microfluidic device, the data can be output as a heat matrix (also termed "heat map"). In the heat matrix, each square, representing a reaction chamber on the DA matrix, has been assigned a color value which can be shown in gray scale, but is more typically shown in color. In gray scale, black squares indicate that no amplification product was detected, whereas white squares indicate the highest level of amplification produce, with shades of gray indicating levels of amplification product in between. In a further aspect, a software program may be used to compile the data generated in the heat matrix into a more reader-friendly format.

Applications

The methods of the invention are applicable to any technique aimed at detecting the presence or amount of one or more target nucleic acids in a nucleic acid sample. Thus, for example, these methods are applicable to identifying the presence of particular polymorphisms (such as SNPs), alleles, or haplotypes, or chromosomal abnormalities, such as amplifications, deletions, or aneuploidy. The methods may be employed in genotyping, which can be carried out in a number of contexts, including diagnosis of genetic diseases or disorders, pharmacogenomics (personalized medicine), quality control in agriculture (e.g., for seeds or livestock), the study and management of populations of plants or animals (e.g., in aquaculture or fisheries management or in the determination of population diversity), or paternity or forensic identifications. The methods of the invention can be applied in the identification of sequences indicative of particular conditions or organisms in biological or environmental samples. For example, the methods can be used in assays to identify pathogens, such as viruses, bacteria, and fungi). The methods can also be used in studies aimed at characterizing environments or microenvironments, e.g., characterizing the microbial species in the human gut.

These methods can also be employed in determinations DNA or RNA copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages.

In addition, the methods can be employed to prepare nucleic acid samples for further analysis, such as, e.g., DNA sequencing.

Finally, nucleic acid samples can be tagged as a first step, prior subsequent analysis, to reduce the risk that mislabeling or cross-contamination of samples will compromise the results. For example, any physician's office, laboratory, or hospital could tag samples immediately after collection, and the tags could be confirmed at the time of analysis. Similarly, samples containing nucleic acids collected at a crime scene could be tagged as soon as practicable, to ensure that the samples could not be mislabeled or tampered with. Detection of the tag upon each transfer of the sample from one party to another could be used to establish chain of custody of the sample.

Kits

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

Multi-Primer Amplification Method for Barcoding of Target Nucleic Acids in Preparation for DNA Sequencing

Figure 10:
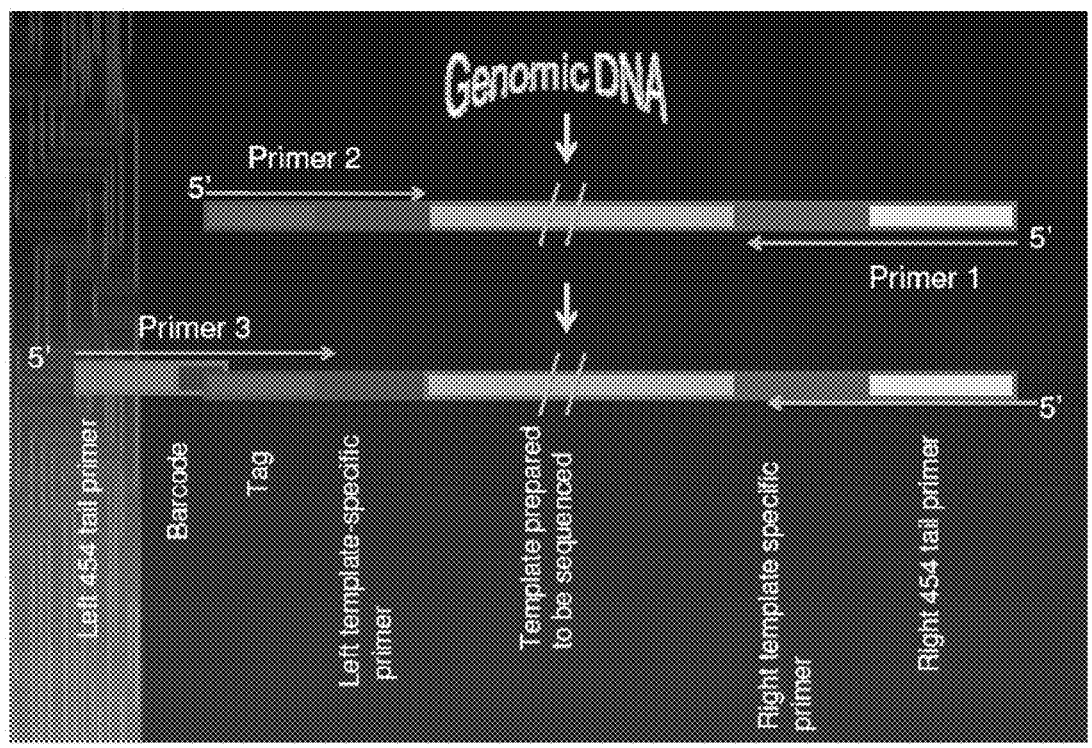
FIG. 10 illustrates an embodiment of a 3-primer amplification method for barcoding target nucleic acids prior to sequencing.
Figure 11:
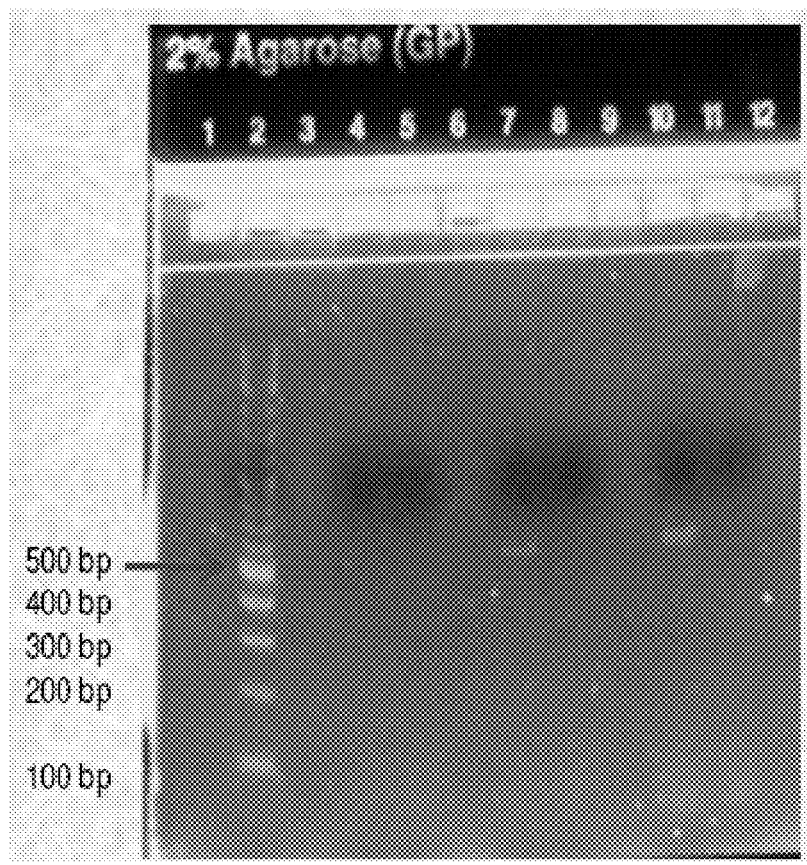
FIG. 11 shows a photograph of the gel described in Example 1. The lanes are as follows: (2) molecular markers, (4) sample amplified with 454 tails; (5) sample (NTC) amplified with 454 tails; (7) sample amplified with A5 primer pair; (8) sample (NTC) amplified with A5 primer pair; (10) sample amplified with 3 primers; and (11) sample (NTC) amplified with 3 primers.

Genomic DNA samples (BioChain, USA) at 100 and 0 ng/ml (negative control ["NTC"]) were amplified for 25 cycles 7900HT Fast Real-Time PCR System (Applied Biosystems, USA) with the following primer pairs at 200 nM per primer: 1) 454 tails; 2) A5 specific primers; and 3) the three primers shown in FIG. 10. PCR was performed in 15 µl reaction volumes containing 7.5 µl of FastStart TaqMan® Probe Master (Roche Diagnostics, USA), 0.75 µl of DA sample loading reagent (Fluidigm Corp, USA) and 6.75 µl of sample. Thermal cycling condition included an initial hot start at 50° C. for 2 minutes and at 94° C. for 10 minutes, followed by 25 cycles at 94° C. for 15 s, 70° C. for 5 s, 60° C. for 30 s and 72° C. for 90 s. The resulting amplification products were run on an electrophoresis gel (Invitrogen, USA) using 8 µl of the reaction mixture per lane following the manufacturer instruction. See FIG. 11, which shows that the 3-primer method produced an amplicon of the correct size. The amplicons generated from PCR amplification were purified using Ampure Beads® and then re-amplified on a PCR plate with 454 tail primers, followed by Sanger sequencing with either 454 tail primers, which showed that the 3-primer method generated an amplicon having the correct sequence.

Example 2

Multi-Primer Amplification Method for Quantifying Target Nucleic Acids in Preparation for DNA Sequencing

Primers for preparing genomic DNA for sequencing using various DNA conventional DNA sequencing methods are shown below.

```
ShotGun Forward:
                                        (SEQ ID NO: 1)
5'-CCATCTCATCCCTGCGTGTC-3'

ShotGun Reverse:
                                        (SEQ ID NO: 2)
5'-CCTATCCCCTGTGTGCCTTG-3'

ShotGun UPR Forward:
                                        (SEQ ID NO: 3)
5'-GGCGGCGACCATCTCATCCCTGCGTGTC-3'

MID Forward:
                                        (SEQ ID NO: 4)
5'-GCCTCCCTCGCGCCATCAG-3'

MID Reverse:
                                        (SEQ ID NO: 5)
5'-GCCTTGCCAGCCCGCTCAG-3'

MID UPR Forward:
                                        (SEQ ID NO: 6)
5'-GGCGGCGAGCCTCCCTCGCGCCATCAG-3'

Solexa Forward:
                                        (SEQ ID NO: 7)
5'-ACACTCTTTCCCTACACGA-3'

Solexa Reverse:
                                        (SEQ ID NO: 8)
5'-CAAGCAGAAGACGGCATA-3'

Solexa UPR Forward:
                                        (SEQ ID NO: 9)
5'-GGCGGCGAACACTCTTTCCCTACACGA-3'

Solid Forward:
                                        (SEQ ID NO: 10)
5'-CCACTACGCCTCCGCTTTCCTCTCTATG-3'

Solid Reverse:
                                        (SEQ ID NO: 11)
5'-CTGCCCCGGGTTCCTCATTCT-3'

Solid UPR Forward:
                                        (SEQ ID NO: 12)
5'-GGCGGCGACCACTACGCCTCCGCTTTCCTCTCTATG-3'

454 Titanium Forward:
                                        (SEQ ID NO: 13)
5'-CCATCTCATCCCTGCGTG-3'

454 Titanium Reverse:
                                        (SEQ ID NO: 14)
5'-CCTATCCCCTGTGTGCCTTG-3'

454 Titanium UPR Forward:
                                        (SEQ ID NO: 15)
5'-GGCGGCGACCATCTCATCCCTGCGTG-3'

Solexa smRNA Forward:
                                        (SEQ ID NO: 16)
5'-TAATGATACGGCGACCACC-3'

Solexa smRNA Reverse:
                                        (SEQ ID NO: 17)
5'-ACAAGCAGAAGACGGCATAC-3'

Solexa smRNA UPL Forward:
                                        (SEQ ID NO: 18)
5'-GGCGGCGATAATGATACGGCGACCAC-3'
```

The properties of these primers is shown in Table 1 below.

TABLE 1

| | Primer | Length (nt) | CG % | Tm (° C.) | Primer-Dimer |
|---|---|---|---|---|---|
| 454-standard (ShotGun) | ShotGun Forward: | 20 | 60 | 68.4 | No self/cross-dimer, 1.5° C. diff in Tm |
| | ShotGun Reverse: | 20 | 60 | 66.9 | |
| | ShotGun UPR Forward: | 28 | 67.8 | 84.8 | |

TABLE 1-continued

| | Primer | Length (nt) | CG % | Tm (° C.) | Primer-Dimer |
|---|---|---|---|---|---|
| 454-MID | MID Forward: | 19 | 73.6 | 74.9 | 4-bases of self-dimer(F.UPL) & cross-dimer(F./UPL, R/UPL) |
| | MID Reverse: | 19 | 73.6 | 74.9 | High GC |
| | MID UPR Forward: | 27 | 77.7 | 88.5 | |
| Solexa | Solexa Forward: | 19 | 47.3 | 57.8 | No dimer, 2.1° C. diff in Tm |
| | Solexa Reverse: | 18 | 50 | 60.6 | Low GC |
| | Solexa UPR Forward: | 27 | 59.2 | 78.4 | |
| Solid | Solid Forward: | 28 | 57.1 | 74.7 | Strong self-dimer & cross-dimer |
| | Solid Reverse: | 21 | 61.9 | 72.5 | variety of GC & Tm |
| | Solid UPR Forward: | 36 | 63.8 | 85.6 | |

The reaction mixture used for amplification of genomic DNA to incorporate primer sequences is given below in Table 2.

TABLE 2

| | Add V μl of TE into dry probe tube | |
|---|---|---|
| 100 uM stock solution | V = "Total nmol" value of the dry probe * 10 | |
| 10X Fluidigm Assay | | |
| | 100 μMol | |
| Forward: | 4 | 2000 nM |
| UPR Forward: | 4 | 2000 nM |
| Reverse: | 8 | 4000 nM |
| TE: | 184 | |
| Total: | 200 | |

Example 3

Additional Illustrative Primers for Barcoding of Target Nucleic Acids in Preparation for 454 DNA Sequencing Tables 3 and 4 below show additional illustrative primers for barcoding of target nucleic acids in preparation for 454 DNA sequencing. "454F" refers to a 454 forward primer binding site; "454R" refers to 454 reverse primer binding site. "BC" refers to a nucleotide barcode. "TAG" refers to a nucleotide tag. "P53" refers to a target-specific primer sequence.

TABLE 3

| Sequence Name | Sequence | SEQ ID |
|---|---|---|
| 454F-BC1-TAG8 | GCCTCCCTCGCGCCATCAGGCATGCACACTGACGACA TGGTTCTACA | (SEQ ID NO: 19) |
| 454F-BC2-TAG8 | GCCTCCCTCGCGCCATCAGCGTACGACACTGACGACA TGGTTCTACA | (SEQ ID NO: 20) |
| 454F-BC3-TAG8 | GCCTCCCTCGCGCCATCAGGTCAGCACACTGACGACA TGGTTCTACA | (SEQ ID NO: 21) |
| 454F-BC4-TAG8 | GCCTCCCTCGCGCCATCAGAGCTGCACACTGACGACA TGGTTCTACA | (SEQ ID NO: 22) |
| 454F-BC5-TAG8 | GCCTCCCTCGCGCCATCAGTGCATCACACTGACGACA TGGTTCTACA | (SEQ ID NO: 23) |
| 454F-BC6-TAG8 | GCCTCCCTCGCGCCATCAGCTGATGACACTGACGACA TGGTTCTACA | (SEQ ID NO: 24) |
| 454F-BC7-TAG8 | GCCTCCCTCGCGCCATCAGGTAGTCACACTGACGACA TGGTTCTACA | (SEQ ID NO: 25) |
| 454F-BC8-TAG8 | GCCTCCCTCGCGCCATCAGGTCGATACACTGACGACA TGGTTCTACA | (SEQ ID NO: 26) |
| 454F-BC9-TAG8 | GCCTCCCTCGCGCCATCAGGATACGACACTGACGACA TGGTTCTACA | (SEQ ID NO: 27) |
| 454F-BC10-TAG8 | GCCTCCCTCGCGCCATCAGTGATGCACACTGACGACA TGGTTCTACA | (SEQ ID NO: 28) |
| 454F-BC11-TAG8 | GCCTCCCTCGCGCCATCAGAGCTGAACACTGACGACA TGGTTCTACA | (SEQ ID NO: 29) |

TABLE 3 -continued

| Sequence Name | Sequence | SEQ ID |
|---|---|---|
| 454F-BC12-TAG8 | GCCTCCCTCGCGCCATCAGACTGTAACACTGACGACATGGTTCTACA | (SEQ ID NO: 30) |
| 454F-BC13-TAG8 | GCCTCCCTCGCGCCATCAGTGCATGACACTGACGACATGGTTCTACA | (SEQ ID NO: 31) |
| 454F-BC14-TAG8 | GCCTCCCTCGCGCCATCAGAGTCTAACACTGACGACATGGTTCTACA | (SEQ ID NO: 32) |
| 454F-BC15-TAG8 | GCCTCCCTCGCGCCATCAGTGTCTGACACTGACGACATGGTTCTACA | (SEQ ID NO: 33) |
| 454F-BC16-TAG8 | GCCTCCCTCGCGCCATCAGGCTAGCACACTGACGACATGGTTCTACA | (SEQ ID NO: 34) |
| 454F-BC17-TAG8 | GCCTCCCTCGCGCCATCAGGATAGCACACTGACGACATGGTTCTACA | (SEQ ID NO: 35) |
| 454F-BC18-TAG8 | GCCTCCCTCGCGCCATCAGGCTACTACACTGACGACATGGTTCTACA | (SEQ ID NO: 36) |
| 454F-BC19-TAG8 | GCCTCCCTCGCGCCATCAGCTATGCACACTGACGACATGGTTCTACA | (SEQ ID NO: 37) |
| 454F-BC20-TAG8 | GCCTCCCTCGCGCCATCAGGCTATGACACTGACGACATGGTTCTACA | (SEQ ID NO: 38) |
| 454F-BC21-TAG8 | GCCTCCCTCGCGCCATCAGCGTGCAACACTGACGACATGGTTCTACA | (SEQ ID NO: 39) |
| 454F-BC22-TAG8 | GCCTCCCTCGCGCCATCAGATAGCTACACTGACGACATGGTTCTACA | (SEQ ID NO: 40) |
| 454F-BC23-TAG8 | GCCTCCCTCGCGCCATCAGTGTAGCACACTGACGACATGGTTCTACA | (SEQ ID NO: 41) |
| 454F-BC24-TAG8 | GCCTCCCTCGCGCCATCAGGTGCTAACACTGACGACATGGTTCTACA | (SEQ ID NO: 42) |
| 454F-BC25-TAG8 | GCCTCCCTCGCGCCATCAGGTCATGACACTGACGACATGGTTCTACA | (SEQ ID NO: 43) |
| 454F-BC26-TAG8 | GCCTCCCTCGCGCCATCAGATCGTGACACTGACGACATGGTTCTACA | (SEQ ID NO: 44) |
| 454F-BC27-TAG8 | GCCTCCCTCGCGCCATCAGTGTACACACTGACGACATGGTTCTACA | (SEQ ID NO: 45) |
| 454F-BC28-TAG8 | GCCTCCCTCGCGCCATCAGAGTGTAACACTGACGACATGGTTCTACA | (SEQ ID NO: 46) |
| 454F-BC29-TAG8 | GCCTCCCTCGCGCCATCAGTGACAGACACTGACGACATGGTTCTACA | (SEQ ID NO: 47) |
| 454F-BC30-TAG8 | GCCTCCCTCGCGCCATCAGGATCACACACTGACGACATGGTTCTACA | (SEQ ID NO: 48) |
| 454F-BC31-TAG8 | GCCTCCCTCGCGCCATCAGCTAGAGACACTGACGACATGGTTCTACA | (SEQ ID NO: 49) |
| 454F-BC32-TAG8 | GCCTCCCTCGCGCCATCAGCTAGTCACACTGACGACATGGTTCTACA | (SEQ ID NO: 50) |
| 454F-BC33-TAG8 | GCCTCCCTCGCGCCATCAGAGCTAGACACTGACGACATGGTTCTACA | (SEQ ID NO: 51) |
| 454F-BC34-TAG8 | GCCTCCCTCGCGCCATCAGTGACTGACACTGACGACATGGTTCTACA | (SEQ ID NO: 52) |
| 454F-BC35-TAG8 | GCCTCCCTCGCGCCATCAGTGATAGACACTGACGACATGGTTCTACA | (SEQ ID NO: 53) |
| 454F-BC36-TAG8 | GCCTCCCTCGCGCCATCAGCGTATCACACTGACGACATGGTTCTACA | (SEQ ID NO: 54) |
| 454F-BC37-TAG8 | GCCTCCCTCGCGCCATCAGGTCTGAACACTGACGACATGGTTCTACA | (SEQ ID NO: 55) |

TABLE 3-continued

| Sequence Name | Sequence | SEQ ID |
|---|---|---|
| 454F-BC38-TAG8 | GCCTCCCTCGCGCCATCAGCATGACACACTGACGACATGGTTCTACA | (SEQ ID NO: 56) |
| 454F-BC39-TAG8 | GCCTCCCTCGCGCCATCAGCGATGAACACTGACGACATGGTTCTACA | (SEQ ID NO: 57) |
| 454F-BC40-TAG8 | GCCTCCCTCGCGCCATCAGGCTGATACACTGACGACATGGTTCTACA | (SEQ ID NO: 58) |
| 454F-BC41-TAG8 | GCCTCCCTCGCGCCATCAGCAGTACACACTGACGACATGGTTCTACA | (SEQ ID NO: 59) |
| 454F-BC42-TAG8 | GCCTCCCTCGCGCCATCAGGCGACTACACTGACGACATGGTTCTACA | (SEQ ID NO: 60) |
| 454F-BC43-TAG8 | GCCTCCCTCGCGCCATCAGGTACGAACACTGACGACATGGTTCTACA | (SEQ ID NO: 61) |
| 454F-BC44-TAG8 | GCCTCCCTCGCGCCATCAGACGCTAACACTGACGACATGGTTCTACA | (SEQ ID NO: 62) |
| 454F-BC45-TAG8 | GCCTCCCTCGCGCCATCAGAGCATCACACTGACGACATGGTTCTACA | (SEQ ID NO: 63) |
| 454F-BC46-TAG8 | GCCTCCCTCGCGCCATCAGGATGCTACACTGACGACATGGTTCTACA | (SEQ ID NO: 64) |
| 454F-BC47-TAG8 | GCCTCCCTCGCGCCATCAGGTCTGCACACTGACGACATGGTTCTACA | (SEQ ID NO: 65) |
| 454F-BC48-TAG8 | GCCTCCCTCGCGCCATCAGATGCGAACACTGACGACATGGTTCTACA | (SEQ ID NO: 66) |

TABLE 4

| Sequence Name | Sequence | SEQ ID |
|---|---|---|
| TAGS-P53-1+ | ACACTGACGACATGGTTCTACAACTGTCCAGCTTTGTGCC | (SEQ ID NO: 67) |
| TAGS-P53-2+ | ACACTGACGACATGGTTCTACAGATCATCATAGGAGTTGCATTGTTG | (SEQ ID NO: 68) |
| TAGS-P53-3+ | ACACTGACGACATGGTTCTACACGGACCTTTGTCCTTCCT | (SEQ ID NO: 69) |
| TAGS-P53-4+ | ACACTGACGACATGGTTCTACAATGCAAACCTCAATCCCTCC | (SEQ ID NO: 70) |
| TAGS-P53-5+ | ACACTGACGACATGGTTCTACAAGTTTCTTCCCATGCACCTG | (SEQ ID NO: 71) |
| TAGS-P53-6+ | ACACTGACGACATGGTTCTACAGTGAATCCCCGTCTCTACTAAAA | (SEQ ID NO: 72) |
| TAGS-P53-7+ | ACACTGACGACATGGTTCTACATGTTTCCCATTTGCGGTTATGA | (SEQ ID NO: 73) |
| TAGS-P53-8+ | ACACTGACGACATGGTTCTACAAGTTGTGGGACTGCTTTATACATT | (SEQ ID NO: 74) |
| 454R-P53-1- | GCCTTGCCAGCCCGCTCAGTCCTCTGCCTAGGCGTT | (SEQ ID NO: 75) |
| 454R-P53-2- | GCCTTGCCAGCCCGCTCAGGAAATGTAAATGTGGAGCCAAACA | (SEQ ID NO: 76) |
| 454R-P53-3- | GCCTTGCCAGCCCGCTCAGACTCATTCTTGAAAATACCTCCGG | (SEQ ID NO: 77) |
| 454R-P53-4- | GCCTTGCCAGCCCGCTCAGAAATGCCACCTCGATTTAGGAAA | (SEQ ID NO: 78) |
| 454R-P53-5- | GCCTTGCCAGCCCGCTCAGTCACCCTCCCGAATAGCT | (SEQ ID NO: 79) |

TABLE 4-continued

| Sequence Name | Sequence | SEQ ID |
|---|---|---|
| 454R-P53-6- | GCCTTGCCAGCCCGCTCAGAGTGTAAAATGGTACAACCGCT | (SEQ ID NO: 80) |
| 454R-P53-7- | GCCTTGCCAGCCCGCTCAGCCTCTTAAGATACTGTAAACTCTGTAAAGC | (SEQ ID NO: 81) |
| 454R-P53-8- | GCCTTGCCAGCCCGCTCAGATTGTGCCATTGTACTCTAGCC | (SEQ ID NO: 82) |
| TAGS-P53-9+ | ACACTGACGACATGGTTCTACACTTCCTTTCTCTACTGAATGCTTTTAATTT | (SEQ ID NO: 83) |
| TAGS-P53-10+ | ACACTGACGACATGGTTCTACATCTTACACAAACTCTTCAGAAAACAGA | (SEQ ID NO: 84) |
| TAGS-P53-11+ | ACACTGACGACATGGTTCTACAGTACCAAAACCAAACAAGGACAT | (SEQ ID NO: 85) |
| TAGS-P53-12+ | ACACTGACGACATGGTTCTACAGGTGAAACGCCATCTCTACTAA | (SEQ ID NO: 86) |
| TAGS-P53-13+ | ACACTGACGACATGGTTCTACATCATGATTGTAGCTGATTCAACATTCA | (SEQ ID NO: 87) |
| TAGS-P53-14+ | ACACTGACGACATGGTTCTACAACTAGCATGCTGAAACCCC | (SEQ ID NO: 88) |
| TAGS-P53-15+ | ACACTGACGACATGGTTCTACATCAGGAGATCGAGACCATCC | (SEQ ID NO: 89) |
| TAGS-P53-16+ | ACACTGACGACATGGTTCTACATCATGCCTGTAATCCCAGC | (SEQ ID NO: 90) |
| 454R-P53-9- | GCCTTGCCAGCCCGCTCAGACCTCAAATGATCCCCTGC | (SEQ ID NO: 91) |
| 454R-P53-10- | GCCTTGCCAGCCCGCTCAGATTACAGGCGTGAGCCAC | (SEQ ID NO: 92) |
| 454R-P53-11- | GCCTTGCCAGCCCGCTCAGTTTTGAGATGAAGTCTTGCTCTGT | (SEQ ID NO: 93) |
| 454R-P53-12- | GCCTTGCCAGCCCGCTCAGTAAAGACCAGTCTGACTATGTTGC | (SEQ ID NO: 94) |
| 454R-P53-13- | GCCTTGCCAGCCCGCTCAGACCATGCCCGGCTAATTTT | (SEQ ID NO: 95) |
| 454R-P53-14- | GCCTTGCCAGCCCGCTCAGAGTTCACGCCATTCTCCTG | (SEQ ID NO: 96) |
| 454R-P53-15- | GCCTTGCCAGCCCGCTCAGCACTACGCCCGGCTAATTTT | (SEQ ID NO: 97) |
| 454R-P53-16- | GCCTTGCCAGCCCGCTCAGTGGCCCCATTAGGACATGTAT | (SEQ ID NO: 98) |
| TAGS-P53-17+ | ACACTGACGACATGGTTCTACATTGTCCCATTGCACTCCAG | (SEQ ID NO: 99) |
| TAGS-P53-18+ | ACACTGACGACATGGTTCTACATGGGCAACAAGAGTGAAACT | (SEQ ID NO: 100) |
| TAGS-P53-19+ | ACACTGACGACATGGTTCTACAAAATAAATATAGCAGGGTTGCAGGT | (SEQ ID NO: 101) |
| TAGS-P53-20+ | ACACTGACGACATGGTTCTACATGCATTTCTCTTGGCTCCC | (SEQ ID NO: 102) |
| TAGS-P53-21+ | ACACTGACGACATGGTTCTACAACTTTCCTCAACTCTACATTTCCC | (SEQ ID NO: 103) |
| TAGS-P53-22+ | ACACTGACGACATGGTTCTACATCAGTGCAAACAACAGAAAAGTG | (SEQ ID NO: 104) |
| TAGS-P53-23+ | ACACTGACGACATGGTTCTACACATGTTTCTTAGCAAATCTGATGACA | (SEQ ID NO: 105) |

TABLE 4 -continued

| Sequence Name | Sequence | SEQ ID |
|---|---|---|
| TAGS-P53-24+ | ACACTGACGACATGGTTCTACATCTGTGGTCCCAGCTACT | (SEQ ID NO: 106) |
| 454R-P53-17- | GCCTTGCCAGCCCGCTCAGTTTCACCATGTTAGGTTGGTCTC | (SEQ ID NO: 107) |
| 454R-P53-18- | GCCTTGCCAGCCCGCTCAGTGTAGGTTAAATCCAAATACTATACCGTC | (SEQ ID NO: 108) |
| 454R-P53-19- | GCCTTGCCAGCCCGCTCAGTCTCAAATCTTCAGTAGCAACTAAAATCT | (SEQ ID NO: 109) |
| 454R-P53-20- | GCCTTGCCAGCCCGCTCAGTCCCGACCTCAGGTGATC | (SEQ ID NO: 110) |
| 454R-P53-21- | GCCTTGCCAGCCCGCTCAGTGGTCTTGAACTCCCAACTTC | (SEQ ID NO: 111) |
| 454R-P53-22- | GCCTTGCCAGCCCGCTCAGCCTCCGACTCCCAAAGTG | (SEQ ID NO: 112) |
| 454R-P53-23- | GCCTTGCCAGCCCGCTCAGACTACAGCCTCGGACTCC | (SEQ ID NO: 113) |
| 454R-P53-24- | GCCTTGCCAGCCCGCTCAGATCTTGCACGAAGTTATGCAACTA | (SEQ ID NO: 114) |
| TAGS-P53-25+ | ACACTGACGACATGGTTCTACAACCACTGCACTCCAGC | (SEQ ID NO: 115) |
| TAGS-P53-26+ | ACACTGACGACATGGTTCTACAACAAGGAAAAGTATCAGACAATGTAAGT | (SEQ ID NO: 116) |
| TAGS-P53-27+ | ACACTGACGACATGGTTCTACAACGGTAGCTCACACCTGTAAT | (SEQ ID NO: 117) |
| TAGS-P53-28+ | ACACTGACGACATGGTTCTACATGGAAGTCCCTCTCTGATTGT | (SEQ ID NO: 118) |
| TAGS-P53-29+ | ACACTGACGACATGGTTCTACAACTGACTTTCTGCTCTTGTCTTTC | (SEQ ID NO: 119) |
| TAGS-P53-30+ | ACACTGACGACATGGTTCTACAATTCTGGGACAGCCAAGTC | (SEQ ID NO: 120) |
| TAGS-P53-31+ | ACACTGACGACATGGTTCTACAAGGAGTTCAAGACCAGCCT | (SEQ ID NO: 121) |
| TAGS-P53-32+ | ACACTGACGACATGGTTCTACATCTGTCTCCTTCCTCTTCCTAC | (SEQ ID NO: 122) |
| 454R-P53-25- | GCCTTGCCAGCCCGCTCAGCCTCTTCCCCAAAAGCTCT | (SEQ ID NO: 123) |
| 454R-P53-26- | GCCTTGCCAGCCCGCTCAGTCTCGAACTCCTTACTTCAGGT | (SEQ ID NO: 124) |
| 454R-P53-27- | GCCTTGCCAGCCCGCTCAGCCCAACACCATGCCAGTG | (SEQ ID NO: 125) |
| 454R-P53-28- | GCCTTGCCAGCCCGCTCAGTCCCAGCCCTCCAG | (SEQ ID NO: 126) |
| 454R-P53-29- | GCCTTGCCAGCCCGCTCAGATTGAAGTCTCATGGAAGCCAG | (SEQ ID NO: 127) |
| 454R-P53-30- | GCCTTGCCAGCCCGCTCAGTCAAGTGATCTTCCCACCTCA | (SEQ ID NO: 128) |
| 454R-P53-31- | GCCTTGCCAGCCCGCTCAGACAACCTCCGTCATGTGC | (SEQ ID NO: 129) |
| 454R-P53-32- | GCCTTGCCAGCCCGCTCAGACCCATTTACTTTGCACATCTCA | (SEQ ID NO: 130) |
| TAGS-P53-33+ | ACACTGACGACATGGTTCTACATTAAGGGTGGTTGTCAGTGG | (SEQ ID NO: 131) |
| TAGS-P53-34+ | ACACTGACGACATGGTTCTACATTGCAGTGAGCTGAGATCAC | (SEQ ID NO: 132) |
| TAGS-P53-35+ | ACACTGACGACATGGTTCTACAATCTCCTTACTGCTCCCACT | (SEQ ID NO: 133) |

TABLE 4 -continued

| Sequence Name | Sequence | SEQ ID |
|---|---|---|
| TAGS-P53-36+ | ACACTGACGACATGGTTCTACATTTTATCACCTTTCCTTGCCTCTT | (SEQ ID NO: 134) |
| TAGS-P53-37+ | ACACTGACGACATGGTTCTACAACTCGTCGTAAGTTGAAAATATTGTAAGT | (SEQ ID NO: 135) |
| TAGS-P53-38+ | ACACTGACGACATGGTTCTACATCCCAAAGTGCTGGGATTAC | (SEQ ID NO: 136) |
| TAGS-P53-39+ | ACACTGACGACATGGTTCTACATCCATCCTCCCAGCTCAG | (SEQ ID NO: 137) |
| TAGS-P53-40+ | ACACTGACGACATGGTTCTACAATCTCAGCTCACTGCAGC | (SEQ ID NO: 138) |
| 454R-P53-33- | GCCTTGCCAGCCCGCTCAGAGCCAACCTAGGAGATAACACA | (SEQ ID NO: 139) |
| 454R-P53-34- | GCCTTGCCAGCCCGCTCAGAGGCTCCATCTACTCCCAA | (SEQ ID NO: 140) |
| 454R-P53-35- | GCCTTGCCAGCCCGCTCAGTTGATAAGAGGTCCCAAGACTTAGTA | (SEQ ID NO: 141) |
| 454R-P53-36- | GCCTTGCCAGCCCGCTCAGTGGGTGACAGAGTGAGACT | (SEQ ID NO: 142) |
| 454R-P53-37- | GCCTTGCCAGCCCGCTCAGACATCACTGTAATCCAGCCTG | (SEQ ID NO: 143) |
| 454R-P53-38- | GCCTTGCCAGCCCGCTCAGAGATCATGCCACTGCACTC | (SEQ ID NO: 144) |
| 454R-P53-39- | GCCTTGCCAGCCCGCTCAGGGCATGTGCCTGTAGTCC | (SEQ ID NO: 145) |
| 454R-P53-40- | GCCTTGCCAGCCCGCTCAGTGGTCTTGAACTCCTGACCT | (SEQ ID NO: 146) |
| TAGS-P53-41+ | ACACTGACGACATGGTTCTACAAAACAGCATGGTTGCATGAAAG | (SEQ ID NO: 147) |
| TAGS-P53-42+ | ACACTGACGACATGGTTCTACAAGTCGCATGCACATGTAGTC | (SEQ ID NO: 148) |
| TAGS-P53-43+ | ACACTGACGACATGGTTCTACAAAAAGTCAGCTGTATAGGTACTTGAAG | (SEQ ID NO: 149) |
| TAGS-P53-44+ | ACACTGACGACATGGTTCTACACCTCAGTGTATCCACAGAACA | (SEQ ID NO: 150) |
| TAGS-P53-45+ | ACACTGACGACATGGTTCTACAATGCATGCCTGTAATCCCAG | (SEQ ID NO: 151) |
| TAGS-P53-46+ | ACACTGACGACATGGTTCTACAAACTCATGTTCAAGACAGAAGGG | (SEQ ID NO: 152) |
| TAGS-P53-47+ | ACACTGACGACATGGTTCTACAATTTTCTCTAACTTCAAGGCCCATAT | (SEQ ID NO: 153) |
| TAGS-P53-48+ | ACACTGACGACATGGTTCTACATGGATCCACCAAGACTTGTTTTAT | (SEQ ID NO: 154) |
| 454R-P53-41- | GCCTTGCCAGCCCGCTCAGGATTACAGGTGTGAGCCACT | (SEQ ID NO: 155) |
| 454R-P53-42- | GCCTTGCCAGCCCGCTCAGACAGTACCTGAGTTAAAAGATGGTTC | (SEQ ID NO: 156) |
| 454R-P53-43- | GCCTTGCCAGCCCGCTCAGTGAGACCCTCCAGCTCTG | (SEQ ID NO: 157) |
| 454R-P53-44- | GCCTTGCCAGCCCGCTCAGATCTTCCCTTACCCCATTTTACTTTATT | (SEQ ID NO: 158) |
| 454R-P53-45- | GCCTTGCCAGCCCGCTCAGTTCAAAGACCCAAAACCCAAAATG | (SEQ ID NO: 159) |
| 454R-P53-46- | GCCTTGCCAGCCCGCTCAGGTCAAGTTCTAGACCCCATGTAATA | (SEQ ID NO: 160) |

TABLE 4 -continued

| Sequence Name | Sequence | SEQ ID |
|---|---|---|
| 454R-P53-47- | GCCTTGCCAGCCCGCTCAGTGTGGTCCCAGCTACTCC | (SEQ ID NO: 161) |
| 454R-P53-48- | GCCTTGCCAGCCCGCTCAGAGCAAAGTTTTATTGTAA AATAAGAGATCGAT | (SEQ ID NO: 162) |

Example 4

4-Primer Barcoding of Target Nucleic Acids in Preparation for 454 DNA Sequencing Using a Microfluidic Device that Permits Recovery of Amplication Products Target-specific primers were designed for 48 genomic regions associated with prostate cancer. In addition to the target-specific regions, the primers were designed to contain additional tag sequences at the 5' end. Forward primers contained the sequence ACACTGACGACATGGTTC-TACA (SEQ ID NO:163). Reverse primers contained the sequence TACGGTAGCAGAGACTTGGTCT (SEQ ID NO:164). The sequences of the primers containing both tag sequences and the target-specific regions are listed in Table 5.

TABLE 5

| Assay # | Assay Name | Tagged Forward primer sequence | Tagged Reverse primer sequence | Amplicon position | Amplicon size (no tags) |
|---|---|---|---|---|---|
| 1 | MSMB-1 | ACACTGACGACAT GGTTCTACAGTGG TTGCCCTCTCCAG TA (SEQ ID NO: 547) | TACGGTAGCAGA GACTTGGTCTGCA CACGCATATTAAA ATAGGAA (SEQ ID NO: 165) | chr10:51219512 + 51219668 | 157 |
| 2 | MSMB-2 | ACACTGACGACAT GGTTCTACATCAT TCTCCACCCTGAC CTT (SEQ ID NO: 548) | TACGGTAGCAGA GACTTGGTCTTTC ATCTGCAGACAG GTCCA (SEQ ID NO: 166) | chr10:51225703 + 51225910 | 208 |
| 3 | MSMB-3 | ACACTGACGACAT GGTTCTACAAGGC CTTGTTCTCATTG CAT (SEQ ID NO: 549) | TACGGTAGCAGA GACTTGGTCTCCA GCACTGGCTTGAG ACTT (SEQ ID NO: 167) | chr10:51226702 + 51226884 | 183 |
| 4 | MSMB-4 | ACACTGACGACAT GGTTCTACAGGGT CCTTTCTCTTCTA ACAGG (SEQ ID NO: 550) | TACGGTAGCAGA GACTTGGTCTAGG CCAGAGGAGAAT GAGG (SEQ ID NO: 168) | chr10:51232232 + 51232460 | 229 |
| 5 | HNF1B-1 | ACACTGACGACAT GGTTCTACACAGA GGGTGATGGTGTG GA (SEQ ID NO: 551) | TACGGTAGCAGA GACTTGGTCTATG ACCCTGCCAAATG ACAC (SEQ ID NO: 169) | chr17:33121423 + 33121560 | 138 |
| 6 | HNF1B-5 | ACACTGACGACAT GGTTCTACATGCT TCCCATTCTTCTT CTCC (SEQ ID NO: 552) | TACGGTAGCAGA GACTTGGTCTTGG AAACTGCTCTTTG TGGTC (SEQ ID NO: 170) | chr17:33138980 + 33139231 | 252 |
| 7 | HNF1B-6 | ACACTGACGACAT GGTTCTACATGCC TCTTATCTTATCA GCTCCA (SEQ ID NO: 553) | TACGGTAGCAGA GACTTGGTCTTGG TGGCACTAATGTT CCCTA (SEQ ID NO: 171) | chr17:33144574 + 33144827 | 254 |
| 8 | HNF1B-7 | ACACTGACGACAT GGTTCTACATAAG ATCCGTGGCAAG AACC (SEQ ID NO: 554) | TACGGTAGCAGA GACTTGGTCTGAG GTCCGTGTCTACA ACTGG (SEQ ID NO: 172) | chr17:33165634 + 33165867 | 234 |

TABLE 5-continued

| Assay # | Assay Name | Tagged Forward primer sequence | Tagged Reverse primer sequence | Amplicon position | Amplicon size (no tags) |
|---|---|---|---|---|---|
| 9 | HNF1B-8 | ACACTGACGACATGGTTCTACAGTCCATGGCCAGCTTTTG (SEQ ID NO: 555) | TACGGTAGCAGAGACTTGGTCTCCCCTCACTCACCATCTCC (SEQ ID NO: 173) | chr17:33165796 + 33165970 | 175 |
| 10 | HNF1B-9 | ACACTGACGACATGGTTCTACAAGGGTTCCTGGGTCTGTGTA (SEQ ID NO: 556) | TACGGTAGCAGAGACTTGGTCTAGTCCGATGATGCCTGCT (SEQ ID NO: 174) | chr17:33167605 + 33167819 | 215 |
| 11 | HNF1B-10 | ACACTGACGACATGGTTCTACACTTCTTGTTGGTGGGCTCAG (SEQ ID NO: 557) | TACGGTAGCAGAGACTTGGTCTTGAGTGAAGGCTACAGACCCTA (SEQ ID NO: 175) | chr17:33167782 + 33167975 | 194 |
| 12 | HNF1B-11 | ACACTGACGACATGGTTCTACATGAGAGGGCAAAGGTCACTT (SEQ ID NO: 558) | TACGGTAGCAGAGACTTGGTCTAGAGGGAGGTGGTCGATGT (SEQ ID NO: 176) | chr17:33173490 + 33173681 | 192 |
| 13 | HNF1B-12 | ACACTGACGACATGGTTCTACAGTTGAGATGCTGGGAGAGGT (SEQ ID NO: 559) | TACGGTAGCAGAGACTTGGTCTTCTCCCACTAGTACCCTAACCATC (SEQ ID NO: 177) | chr17:33173623 + 33173782 | 160 |
| 14 | MYC-1 | ACACTGACGACATGGTTCTACAGACCCGCTTCTCTGAAAGG (SEQ ID NO: 560) | TACGGTAGCAGAGACTTGGTCTGCATTCGACTCATCTCAGCA (SEQ ID NO: 178) | chr8:128817980 + 128818121 | 142 |
| 15 | MYC-2 | ACACTGACGACATGGTTCTACACAGGTTTCCGCACCAAGA (SEQ ID NO: 561) | TACGGTAGCAGAGACTTGGTCTCAGCAGCTCGAATTTCTTCC (SEQ ID NO: 179) | chr8:128819612 + 128819858 | 247 |
| 16 | MYC-6 | ACACTGACGACATGGTTCTACAAACCTTGCTAAAGGAGTGATTTCT (SEQ ID NO: 562) | TACGGTAGCAGAGACTTGGTCTCCTCTTGGCAGCAGGATAGT (SEQ ID NO: 180) | chr8:128821784 + 128822038 | 255 |
| 17 | MYC-7 | ACACTGACGACATGGTTCTACAACGTCTCCACACATCAGCAC (SEQ ID NO: 563) | TACGGTAGCAGAGACTTGGTCTAACTCCGGGATCTGGTCAC (SEQ ID NO: 181) | chr8:128821968 + 128822217 | 250 |
| 18 | MYC-8 | ACACTGACGACATGGTTCTACACCAGAGGAGGAACGAGCTAA (SEQ ID NO: 564) | TACGGTAGCAGAGACTTGGTCTTTCTGTTAGAAGGAATCGTTTTCC (SEQ ID NO: 182) | chr8:128822158 + 128822420 | 263 |
| 19 | JAZF1-2 | ACACTGACGACATGGTTCTACATTCCATGTGGTTATGCCAAG (SEQ ID NO: 565) | TACGGTAGCAGAGACTTGGTCTCTCCTGACAGTCCTTGCACTT (SEQ ID NO: 183) | chr7:27846803 + 27847046 | 244 |
| 20 | JAZF1-4 | ACACTGACGACATGGTTCTACACAATAAGCAGCAGATATAAGGTTGTT (SEQ ID NO: 566) | TACGGTAGCAGAGACTTGGTCTCTTTGTGTTAGGTAGCCTCATATATTC (SEQ ID NO: 184) | chr7:27998002 + 27998196 | 195 |

TABLE 5-continued

| Assay # | Assay Name | Tagged Forward primer sequence | Tagged Reverse primer sequence | Amplicon position | Amplicon size (no tags) |
|---|---|---|---|---|---|
| 21 | NCOA4-1 | ACACTGACGACATGGTTCTACATTCAAAGGTGGTTTTTGGTTG (SEQ ID NO: 567) | TACGGTAGCAGAGACTTGGTCTGCCCTGTGTCAAGAGTCCAG (SEQ ID NO: 185) | chr10:51249073 + 51249337 | 265 |
| 22 | NCOA4-2 | ACACTGACGACATGGTTCTACATTGGGAAACATCATTCTTTGG (SEQ ID NO: 568) | TACGGTAGCAGAGACTTGGTCTACCAGAAGCCATGCTCAAAC (SEQ ID NO: 186) | chr10:51250503 + 51250748 | 246 |
| 23 | NCOA4-3 | ACACTGACGACATGGTTCTACATGGTGTCATTGTGGCTAGTTG (SEQ ID NO: 569) | TACGGTAGCAGAGACTTGGTCTTGATCTTATCCTAGCAACACAGAAG (SEQ ID NO: 187) | chr10:51250847 + 51251096 | 250 |
| 24 | NCOA4-4 | ACACTGACGACATGGTTCTACATGAAGTTGATGAAACAGATATTCCTT (SEQ ID NO: 570) | TACGGTAGCAGAGACTTGGTCTAGAAGTGCCCAGTGAAGCAT (SEQ ID NO: 188) | chr10:51251218 + 51251418 | 201 |
| 25 | NCOA4-5 | ACACTGACGACATGGTTCTACATTGGCAGCATAGCATAAATAACA (SEQ ID NO: 571) | TACGGTAGCAGAGACTTGGTCTCCCAAAGGAAGTATAAGCCAAG (SEQ ID NO: 189) | chr10:51252141 + 51252337 | 197 |
| 26 | NCOA4-6 | ACACTGACGACATGGTTCTACACTGCATTTGACATTCCTTGTTT (SEQ ID NO: 572) | TACGGTAGCAGAGACTTGGTCTTCCACCTACTGCTGTGTCTACTG (SEQ ID NO: 190) | chr10:51252768 + 51252994 | 227 |
| 27 | NCOA4-7 | ACACTGACGACATGGTTCTACAGCAGACAGAATCTCCAAAGCA (SEQ ID NO: 573) | TACGGTAGCAGAGACTTGGTCTTCTGATAGGTCCATCTCATCTTGA (SEQ ID NO: 191) | chr10:51254556 + 51254815 | 260 |
| 28 | NCOA4-8 | ACACTGACGACATGGTTCTACAGGTTGGAGATCAAGAGCTTCC (SEQ ID NO: 574) | TACGGTAGCAGAGACTTGGTCTTGGTCATTCAGGCACTTCAG (SEQ ID NO: 192) | chr10:51254768 + 51255022 | 255 |
| 29 | NCOA4-9 | ACACTGACGACATGGTTCTACAGAAACCAGCCCAAAGGTGT (SEQ ID NO: 575) | TACGGTAGCAGAGACTTGGTCTCCTTCTTTCTTCAGAAGCCACT (SEQ ID NO: 193) | chr10:51254962 + 51255214 | 253 |
| 30 | NCOA4-10 | ACACTGACGACATGGTTCTACAGAATTGTGAGAAGGAGGCTCTG (SEQ ID NO: 576) | TACGGTAGCAGAGACTTGGTCTTGGGACTTCCTTCTTTGTATGG (SEQ ID NO: 194) | chr10:51255167 + 51255432 | 266 |
| 31 | NCOA4-11 | ACACTGACGACATGGTTCTACACCTTGTCGGAGTGGCTTATC (SEQ ID NO: 577) | TACGGTAGCAGAGACTTGGTCTCCAGTGCTATTTGATGTTTATGC (SEQ ID NO: 195) | chr10:51255385 + 51255633 | 249 |
| 32 | NCOA4-13 | ACACTGACGACATGGTTCTACAGGAGCTTTAAGGCAGGGAAA (SEQ ID NO: 578) | TACGGTAGCAGAGACTTGGTCTTTGGCAAGCTGCAGTCAC (SEQ ID NO: 196) | chr10:51259156 + 51259310 | 155 |

TABLE 5-continued

| Assay # | Assay Name | Tagged Forward primer sequence | Tagged Reverse primer sequence | Amplicon position | Amplicon size (no tags) |
|---|---|---|---|---|---|
| 33 | NUDT11-1 | ACACTGACGACAT GGTTCTACAAGCG AGGCAGACAAAT AGAAG (SEQ ID NO: 579) | TACGGTAGCAGA GACTTGGTCTGTA CTGACTGTCACGG AGCTG (SEQ ID NO: 197) | chrX:51255496 + 51255748 | 253 |
| 34 | SLC22A 3-4 | ACACTGACGACAT GGTTCTACATCTG CATTCTGGCATGT CTC (SEQ ID NO: 580) | TACGGTAGCAGA GACTTGGTCTTCC CCGTATTAATGCA TGGTAT (SEQ ID NO: 198) | chr6:160738955 + 160739163 | 209 |
| 35 | SLC22A 3-5 | ACACTGACGACAT GGTTCTACAAAGG TGAGCTCTTTTCC TGTCTT (SEQ ID NO: 581) | TACGGTAGCAGA GACTTGGTCTTTG TTGGCTATCTGGC CCTA (SEQ ID NO: 199) | chr6:160748030 + 160748274 | 245 |
| 36 | SLC22A 3-6 | ACACTGACGACAT GGTTCTACATGCT TCTGTGACCTCTT GTGT (SEQ ID NO: 582) | TACGGTAGCAGA GACTTGGTCTGTC TGTTTGGAGTCTA ATTTCTGC (SEQ ID NO: 200) | chr6:160749740 + 160750007 | 268 |
| 37 | SLC22A 3-7 | ACACTGACGACAT GGTTCTACACATA ACTCACAACAGC CTCCTTC (SEQ ID NO: 583) | TACGGTAGCAGA GACTTGGTCTAAT CAATTCACCAGCT TTAGCAA (SEQ ID NO: 201) | chr6:160751720 + 160751920 | 201 |
| 38 | SLC22A 3-10 | ACACTGACGACAT GGTTCTACAGTGG TGGAACTGCCAG GA (SEQ ID NO: 584) | TACGGTAGCAGA GACTTGGTCTGGC TCCCTATACTTGA TTGTGG (SEQ ID NO: 202) | chr6:160778107 + 160778308 | 202 |
| 39 | SLC22A 3-11 | ACACTGACGACAT GGTTCTACACCTC CCTTTCAAACTTT CTGTG (SEQ ID NO: 585) | TACGGTAGCAGA GACTTGGTCTCGC TGGTCTACAGAGT TACTTAGGA (SEQ ID NO: 203) | chr6:160783754 + 160783942 | 189 |
| 40 | SLC22A 3-12 | ACACTGACGACAT GGTTCTACATGAT TATCTTGAAGTCA CTTGTTGAA (SEQ ID NO: 586) | TACGGTAGCAGA GACTTGGTCTTGA AGGCTCTTAAGAA TAGCAAATG (SEQ ID NO: 204) | chr6:160784591 + 160784798 | 208 |
| 41 | SLC22A 3-13 | ACACTGACGACAT GGTTCTACAGTGT CTTCCTGGAGCGG TAA (SEQ ID NO: 587) | TACGGTAGCAGA GACTTGGTCTTTC CCTGTGGATATTC AATTTTCT (SEQ ID NO: 205) | chr6:160788700 + 160788934 | 235 |
| 42 | SLC22A 3-14 | ACACTGACGACAT GGTTCTACATCTT TCCTAAAGACTTT CTCCTTTG (SEQ ID NO: 588) | TACGGTAGCAGA GACTTGGTCTATC TCTGCAAGGCACA GCTT (SEQ ID NO: 206) | chr6:160791984 + 160792152 | 169 |
| 43 | KLK3-1 | ACACTGACGACAT GGTTCTACAAGTC CTGGGGAATGAA GGTT (SEQ ID NO: 589) | TACGGTAGCAGA GACTTGGTCTGGA AAGAGCCTCAGCT TGAC (SEQ ID NO: 207) | chr19:56049936 + 56050140 | 205 |
| 44 | KLK3-2 | ACACTGACGACAT GGTTCTACAGTTC CTCCTGTCAACCC TGA (SEQ ID NO: 590) | TACGGTAGCAGA GACTTGGTCTCCT CTGGGACACAGA CACCT (SEQ ID NO: 208) | chr19:56051260 + 56051515 | 256 |

TABLE 5-continued

| Assay # | Assay Name | Tagged Forward primer sequence | Tagged Reverse primer sequence | Amplicon position | Amplicon size (no tags) |
|---|---|---|---|---|---|
| 45 | KLK3-3 | ACACTGACGACATGGTTCTACATCCTTATCATCCTCGCTCCT (SEQ ID NO: 591) | TACGGTAGCAGAGACTTGGTCTTTCACAGCATCCGTGAGC (SEQ ID NO: 209) | chr19:56053051 + 56053300 | 250 |
| 46 | KLK3-4 | ACACTGACGACATGGTTCTACAACTCCAGCCACGACCTCAT (SEQ ID NO: 592) | TACGGTAGCAGAGACTTGGTCTCCCTCAGACCCAGGCATC (SEQ ID NO: 210) | chr19:56053237 + 56053436 | 200 |
| 47 | KLK3-5 | ACACTGACGACATGGTTCTACAGGTCCAGCCCACAACAGT (SEQ ID NO: 593) | TACGGTAGCAGAGACTTGGTCTCCCAGCCCAGAATTAAGGT (SEQ ID NO: 211) | chr19:56053490 + 56053729 | 240 |
| 48 | KLK3-8 | ACACTGACGACATGGTTCTACATCTTCCAAAGCTGGGAACTG (SEQ ID NO: 594) | TACGGTAGCAGAGACTTGGTCTGGGCACATGGTTCACTGC (SEQ ID NO: 212) | chr19:56054924 + 56055115 | 192 |

Preparation of Reaction Mixtures

Primers were synthesized by IDT at 10 nmol scale, and provided resuspended in water at a concentration of 100 μM. The forward and reverse primer for each region in Table 5 were combined in separate wells in a 96-well PCR plate (USA scientific) to a final concentration of 1 μM of each primer in PCR-quality water (Teknova) containing 0.05% Tween-20.

48 human genomic DNA samples from the HapMap sample collection were resuspended at 50 ng/μl in low-EDTA TE buffer (Teknova), and prepared for PCR as follows.

A pre-sample mixture was prepared as follows:

TABLE 6

| Pre-sample mixture | Volume per sample (μl) | Volume for 64 samples (μl) |
|---|---|---|
| Faststart High Fidelity reaction Buffer with MgCl$_2$ | 0.5 | 32 |
| DMSO | 0.1 | 6.4 |
| PCR-Grade Nucleotide Mixture | 0.1 | 6.4 |
| Faststart High-Fidelity Enzyme Blend (Roche 04 738 292 001) | 0.05 | 3.2 |
| 20x Access Array Loading Reagent (PN: 100-0883) | 0.25 | 16 |

TABLE 6-continued

| Pre-sample mixture | Volume per sample (μl) | Volume for 64 samples (μl) |
|---|---|---|
| 20x Evagreen (Biotium-31000) | 0.25 | 16 |
| 20x ROX dye (Invitrogen 12223-012) | 0.25 | 16 |
| PCR-Grade water | 0.5 | 32 |
| Total | 2 | 128 |

For each sample, a sample mixture containing forward and reverse barcode primers, genomic DNA, and pre-sample mix was prepared in an individual well in a 96-well PCR plate.

TABLE 7

| Sample Mixture | Volume (μl) |
|---|---|
| Pre-sample Mixture | 2 |
| 2 μM forward barcode primer | 0.5 |
| 2 μm reverse barcode primer | 0.5 |
| Genomic DNA (50 ng/μl) | 1 |
| PCR-grade water | 1 |

Each sample was mixed with one pair of barcode primers selected from Table 8.

TABLE 8

| | Reverse barcode primer (454-BC#-CS1) | Reverse barcode primer SEQ ID NO. | Forward barcode primer (454A-BC#-CS2) | Forward barcode primer SEQ ID NO. |
|---|---|---|---|---|
| 1 | GCCTTGCCAGCCCGCTCAGGCATGCTACGGTAGCAGAGACTTGGTCT | (SEQ ID NO: 165) | GCCTCCCTCGCGCCATCAGGCATGCACACTGACGACATGGTTCTACA | (SEQ ID NO: 166) |

TABLE 8-continued

| | Reverse barcode primer (454-BC#-CS1) | Reverse barcode primer SEQ ID NO. | Forward barcode primer (454A-BC#-CS2) | Forward barcode primer SEQ ID NO. |
|---|---|---|---|---|
| 2 | GCCTTGCCAGCCCGCTCAGCGTACGTACGGTAGCAGAGACTTGGTCT | (SEQ ID NO: 167) | GCCTCCCTCGCGCCATCAGCGTACGACACTGACGACATGGTTCTACA | (SEQ ID NO: 168) |
| 3 | GCCTTGCCAGCCCGCTCAGGTCAGCTACGGTAGCAGAGACTTGGTCT | (SEQ ID NO: 169) | GCCTCCCTCGCGCCATCAGGTCAGCACACTGACGACATGGTTCTACA | (SEQ ID NO: 170) |
| 4 | GCCTTGCCAGCCCGCTCAGAGCTGCTACGGTAGCAGAGACTTGGTCT | (SEQ ID NO: 171) | GCCTCCCTCGCGCCATCAGAGCTGCACACTGACGACATGGTTCTACA | (SEQ ID NO: 172) |
| 5 | GCCTTGCCAGCCCGCTCAGTGCATCTACGGTAGCAGAGACTTGGTCT | (SEQ ID NO: 173) | GCCTCCCTCGCGCCATCAGTGCATCACACTGACGACATGGTTCTACA | (SEQ ID NO: 174) |
| 6 | GCCTTGCCAGCCCGCTCAGCTGATGTACGGTAGCAGAGACTTGGTCT | (SEQ ID NO: 175) | GCCTCCCTCGCGCCATCAGCTGATGACACTGACGACATGGTTCTACA | (SEQ ID NO: 176) |
| 7 | GCCTTGCCAGCCCGCTCAGGTAGTCTACGGTAGCAGAGACTTGGTCT | (SEQ ID NO: 177) | GCCTCCCTCGCGCCATCAGGTAGTCACACTGACGACATGGTTCTACA | (SEQ ID NO: 178) |
| 8 | GCCTTGCCAGCCCGCTCAGGTCGATTACGGTAGCAGAGACTTGGTCT | (SEQ ID NO: 179) | GCCTCCCTCGCGCCATCAGGTCGATACACTGACGACATGGTTCTACA | (SEQ ID NO: 180) |
| 9 | GCCTTGCCAGCCCGCTCAGGATACGTACGGTAGCAGAGACTTGGTCT | (SEQ ID NO: 181) | GCCTCCCTCGCGCCATCAGGATACGACACTGACGACATGGTTCTACA | (SEQ ID NO: 182) |
| 10 | GCCTTGCCAGCCCGCTCAGTGATGCTACGGTAGCAGAGACTTGGTCT | (SEQ ID NO: 183) | GCCTCCCTCGCGCCATCAGTGATGCACACTGACGACATGGTTCTACA | (SEQ ID NO: 184) |
| 11 | GCCTTGCCAGCCCGCTCAGAGCTGATACGGTAGCAGAGACTTGGTCT | (SEQ ID NO: 185) | GCCTCCCTCGCGCCATCAGAGCTGAACACTGACGACATGGTTCTACA | (SEQ ID NO: 186) |
| 12 | GCCTTGCCAGCCCGCTCAGACTGTATACGGTAGCAGAGACTTGGTCT | (SEQ ID NO: 187) | GCCTCCCTCGCGCCATCAGACTGTAACACTGACGACATGGTTCTACA | (SEQ ID NO: 188) |
| 13 | GCCTTGCCAGCCCGCTCAGTGCATGTACGGTAGCAGAGACTTGGTCT | (SEQ ID NO: 189) | GCCTCCCTCGCGCCATCAGTGCATGACACTGACGACATGGTTCTACA | (SEQ ID NO: 190) |
| 14 | GCCTTGCCAGCCCGCTCAGAGTCTATACGGTAGCAGAGACTTGGTCT | (SEQ ID NO: 191) | GCCTCCCTCGCGCCATCAGAGTCTAACACTGACGACATGGTTCTACA | (SEQ ID NO: 192) |
| 15 | GCCTTGCCAGCCCGCTCAGTGTCTGTACGGTAGCAGAGACTTGGTCT | (SEQ ID NO: 193) | GCCTCCCTCGCGCCATCAGTGTCTGACACTGACGACATGGTTCTACA | (SEQ ID NO: 194) |
| 16 | GCCTTGCCAGCCCGCTCAGGCTAGCTACGGTAGCAGAGACTTGGTCT | (SEQ ID NO: 195) | GCCTCCCTCGCGCCATCAGGCTAGCACACTGACGACATGGTTCTACA | (SEQ ID NO: 196) |

TABLE 8-continued

| | Reverse barcode primer (454-BC#-CS1) | Reverse barcode primer SEQ ID NO. | Forward barcode primer (454A-BC#-CS2) | Forward barcode primer SEQ ID NO. |
|---|---|---|---|---|
| 17 | GCCTTGCCAGCCCGCTCAGGATAGCTACGGTAGCAGAGACTTGGTCT | (SEQ ID NO: 197) | GCCTCCCTCGCGCCATCAGGATAGCACACTGACGACATGGTTCTACA | (SEQ ID NO: 198) |
| 18 | GCCTTGCCAGCCCGCTCAGGCTACTTACGGTAGCAGAGACTTGGTCT | (SEQ ID NO: 199) | GCCTCCCTCGCGCCATCAGGCTACTACACTGACGACATGGTTCTACA | (SEQ ID NO: 200) |
| 19 | GCCTTGCCAGCCCGCTCAGCTATGCTACGGTAGCAGAGACTTGGTCT | (SEQ ID NO: 201) | GCCTCCCTCGCGCCATCAGCTATGCACACTGACGACATGGTTCTACA | (SEQ ID NO: 202) |
| 20 | GCCTTGCCAGCCCGCTCAGGCTATGTACGGTAGCAGAGACTTGGTCT | (SEQ ID NO: 203) | GCCTCCCTCGCGCCATCAGGCTATGACACTGACGACATGGTTCTACA | (SEQ ID NO: 204) |
| 21 | GCCTTGCCAGCCCGCTCAGCGTGCATACGGTAGCAGAGACTTGGTCT | (SEQ ID NO: 205) | GCCTCCCTCGCGCCATCAGCGTGCAACACTGACGACATGGTTCTACA | (SEQ ID NO: 206) |
| 22 | GCCTTGCCAGCCCGCTCAGATAGCTTACGGTAGCAGAGACTTGGTCT | (SEQ ID NO: 207) | GCCTCCCTCGCGCCATCAGATAGCTACACTGACGACATGGTTCTACA | (SEQ ID NO: 208) |
| 23 | GCCTTGCCAGCCCGCTCAGTGTAGCTACGGTAGCAGAGACTTGGTCT | (SEQ ID NO: 209) | GCCTCCCTCGCGCCATCAGTGTAGCACACTGACGACATGGTTCTACA | (SEQ ID NO: 210) |
| 24 | GCCTTGCCAGCCCGCTCAGGTGCTATACGGTAGCAGAGACTTGGTCT | (SEQ ID NO: 211) | GCCTCCCTCGCGCCATCAGGTGCTAACACTGACGACATGGTTCTACA | (SEQ ID NO: 212) |
| 25 | GCCTTGCCAGCCCGCTCAGGTCATGTACGGTAGCAGAGACTTGGTCT | (SEQ ID NO: 213) | GCCTCCCTCGCGCCATCAGGTCATGACACTGACGACATGGTTCTACA | (SEQ ID NO: 214) |
| 26 | GCCTTGCCAGCCCGCTCAGATCGTGTACGGTAGCAGAGACTTGGTCT | (SEQ ID NO: 215) | GCCTCCCTCGCGCCATCAGATCGTGACACTGACGACATGGTTCTACA | (SEQ ID NO: 216) |
| 27 | GCCTTGCCAGCCCGCTCAGTGTACGTACGGTAGCAGAGACTTGGTCT | (SEQ ID NO: 217) | GCCTCCCTCGCGCCATCAGTGTACGACACTGACGACATGGTTCTACA | (SEQ ID NO: 218) |
| 28 | GCCTTGCCAGCCCGCTCAGAGTGTATACGGTAGCAGAGACTTGGTCT | (SEQ ID NO: 219) | GCCTCCCTCGCGCCATCAGAGTGTAACACTGACGACATGGTTCTACA | (SEQ ID NO: 220) |
| 29 | GCCTTGCCAGCCCGCTCAGTGACAGTACGGTAGCAGAGACTTGGTCT | (SEQ ID NO: 221) | GCCTCCCTCGCGCCATCAGTGACAGACACTGACGACATGGTTCTACA | (SEQ ID NO: 222) |
| 30 | GCCTTGCCAGCCCGCTCAGGATCACTACGGTAGCAGAGACTTGGTCT | (SEQ ID NO: 223) | GCCTCCCTCGCGCCATCAGGATCACACACTGACGACATGGTTCTACA | (SEQ ID NO: 224) |
| 31 | GCCTTGCCAGCCCGCTCAGCTAGAGTACGGTAGCAGAGACTTGGTCT | (SEQ ID NO: 225) | GCCTCCCTCGCGCCATCAGCTAGAGACACTGACGACATGGTTCTACA | (SEQ ID NO: 226) |

TABLE 8-continued

| | Reverse barcode primer (454-BC#-CS1) | Reverse barcode primer SEQ ID NO. | Forward barcode primer (454A-BC#-CS2) | Forward barcode primer SEQ ID NO. |
|---|---|---|---|---|
| 32 | GCCTTGCCAGCCCGCTCAGCTAGTCTACGGTAGCAGAGACTTGGTCT | (SEQ ID NO: 227) | GCCTCCCTCGCGCCATCAGCTAGTCACACTGACGACATGGTTCTACA | (SEQ ID NO: 228) |
| 33 | GCCTTGCCAGCCCGCTCAGAGCTAGTACGGTAGCAGAGACTTGGTCT | (SEQ ID NO: 229) | GCCTCCCTCGCGCCATCAGAGCTAGACACTGACGACATGGTTCTACA | (SEQ ID NO: 230) |
| 34 | GCCTTGCCAGCCCGCTCAGTGACTGTACGGTAGCAGAGACTTGGTCT | (SEQ ID NO: 231) | GCCTCCCTCGCGCCATCAGTGACTGACACTGACGACATGGTTCTACA | (SEQ ID NO: 232) |
| 35 | GCCTTGCCAGCCCGCTCAGTGATAGTACGGTAGCAGAGACTTGGTCT | (SEQ ID NO: 233) | GCCTCCCTCGCGCCATCAGTGATAGACACTGACGACATGGTTCTACA | (SEQ ID NO: 234) |
| 36 | GCCTTGCCAGCCCGCTCAGCGTATCTACGGTAGCAGAGACTTGGTCT | (SEQ ID NO: 235) | GCCTCCCTCGCGCCATCAGCGTATCACACTGACGACATGGTTCTACA | (SEQ ID NO: 236) |
| 37 | GCCTTGCCAGCCCGCTCAGGTCTGATACGGTAGCAGAGACTTGGTCT | (SEQ ID NO: 237) | GCCTCCCTCGCGCCATCAGGTCTGAACACTGACGACATGGTTCTACA | (SEQ ID NO: 238) |
| 38 | GCCTTGCCAGCCCGCTCAGCATGACTACGGTAGCAGAGACTTGGTCT | (SEQ ID NO: 239) | GCCTCCCTCGCGCCATCAGCATGACACACTGACGACATGGTTCTACA | (SEQ ID NO: 240) |
| 39 | GCCTTGCCAGCCCGCTCAGCGATGATACGGTAGCAGAGACTTGGTCT | (SEQ ID NO: 241) | GCCTCCCTCGCGCCATCAGCGATGAACACTGACGACATGGTTCTACA | (SEQ ID NO: 242) |
| 40 | GCCTTGCCAGCCCGCTCAGGCTGATTACGGTAGCAGAGACTTGGTCT | (SEQ ID NO: 243) | GCCTCCCTCGCGCCATCAGGCTGATACACTGACGACATGGTTCTACA | (SEQ ID NO: 244) |
| 41 | GCCTTGCCAGCCCGCTCAGCAGTACTACGGTAGCAGAGACTTGGTCT | (SEQ ID NO: 245) | GCCTCCCTCGCGCCATCAGCAGTACACACTGACGACATGGTTCTACA | (SEQ ID NO: 246) |
| 42 | GCCTTGCCAGCCCGCTCAGGCGACTTACGGTAGCAGAGACTTGGTCT | (SEQ ID NO: 247) | GCCTCCCTCGCGCCATCAGGCGACTACACTGACGACATGGTTCTACA | (SEQ ID NO: 248) |
| 43 | GCCTTGCCAGCCCGCTCAGGTACGATACGGTAGCAGAGACTTGGTCT | (SEQ ID NO: 249) | GCCTCCCTCGCGCCATCAGGTACGAACACTGACGACATGGTTCTACA | (SEQ ID NO: 250) |
| 44 | GCCTTGCCAGCCCGCTCAGACGCTATACGGTAGCAGAGACTTGGTCT | (SEQ ID NO: 251) | GCCTCCCTCGCGCCATCAGACGCTAACACTGACGACATGGTTCTACA | (SEQ ID NO: 252) |
| 45 | GCCTTGCCAGCCCGCTCAGAGCATCTACGGTAGCAGAGACTTGGTCT | (SEQ ID NO: 253) | GCCTCCCTCGCGCCATCAGAGCATCACACTGACGACATGGTTCTACA | (SEQ ID NO: 254) |
| 46 | GCCTTGCCAGCCCGCTCAGGATGCTTACGGTAGCAGAGACTTGGTCT | (SEQ ID NO: 255) | GCCTCCCTCGCGCCATCAGGATGCTACACTGACGACATGGTTCTACA | (SEQ ID NO: 256) |

TABLE 8-continued

| Reverse barcode primer (454-BC#-CS1) | Reverse barcode primer SEQ ID NO. | Forward barcode primer (454A-BC#-CS2) | Forward barcode primer SEQ ID NO. |
|---|---|---|---|
| 47 GCCTTGCCAGCCCGC TCAGGTCTGCTACGG TAGCAGAGACTTGGT CT | (SEQ ID NO: 257) | GCCTCCCTCGCGCCATCAGGTCT GCACACTGACGACATGGTTCTAC A | (SEQ ID NO: 258) |
| 48 GCCTTGCCAGCCCGC TCAGATGCGATACGG TAGCAGAGACTTGGT CT | (SEQ ID NO: 259) | GCCTCCCTCGCGCCATCAGATGC GAACACTGACGACATGGTTCTAC A | (SEQ ID NO: 260) |

Running the Access Array IFC

The containment and interface accumulator reservoirs were filled with 300 µl of Control Line Fluid (Fluidigm PN 89000020) and the H1-H4 reagent wells were loaded with 500 µl of 0.05% Tween-20 in PCR-grade water prior to Access Array IFC loading. 5 µl of each sample mixture was loaded into the sample ports, and 5 µl of each primer mixture was loaded into the primer inlets on the Access Array IFC.

The Access Array IFC was thermal cycled and imaged using a BioMark™ Real-Time PCR system manufactured by Fluidigm Corporation. The Access Array IFC thermal cycling protocol contains a thermal mix step [50° C. for 2 min, 70° C. for 20 min], a hotstart step [95° C. for 10 min], a 35 cycle touch down PCR strategy [2 cycles of 95° C. for 15 sec and 63° C. for 1 min, 2 cycles of 95° C. for 15 sec and 62° C. for 1 min, 2 cycles of 95° C. for 15 sec and 61° C. for 1 min, 2 cycles of 95° C. for 15 sec and 60° C. for 1 min, 2 cycles of 95° C. for 15 sec and 58° C. for 1 min, 25 cycles of 95° C. for 15 sec and 72° C. for 1 min], and an elongation step [72° C. for 3 min]. The real-time data was analyzed with Fluidigm Real-Time PCR Analysis software to obtain $C_T$ values for each reaction chamber.

After amplification, the PCR products were harvested from the Access Array IFC using the Post-PCR IFC Loader AX. Before harvesting, each sample port was filled with 2 µl of 0.05% Tween-20. Residual solution was removed from the H1-H4 reagent wells, and they were refilled with 600 µl of 1× Access Array Harvesting Reagent (0.05% tween-20). After harvesting, each sample port became a PCR product outlet that contained 10 µl (±10%) of 48 pooled PCR products. The pooled PCR products were removed from the Access Array IFC and stored in a microtiter plate at 4° C.

Figure 12:
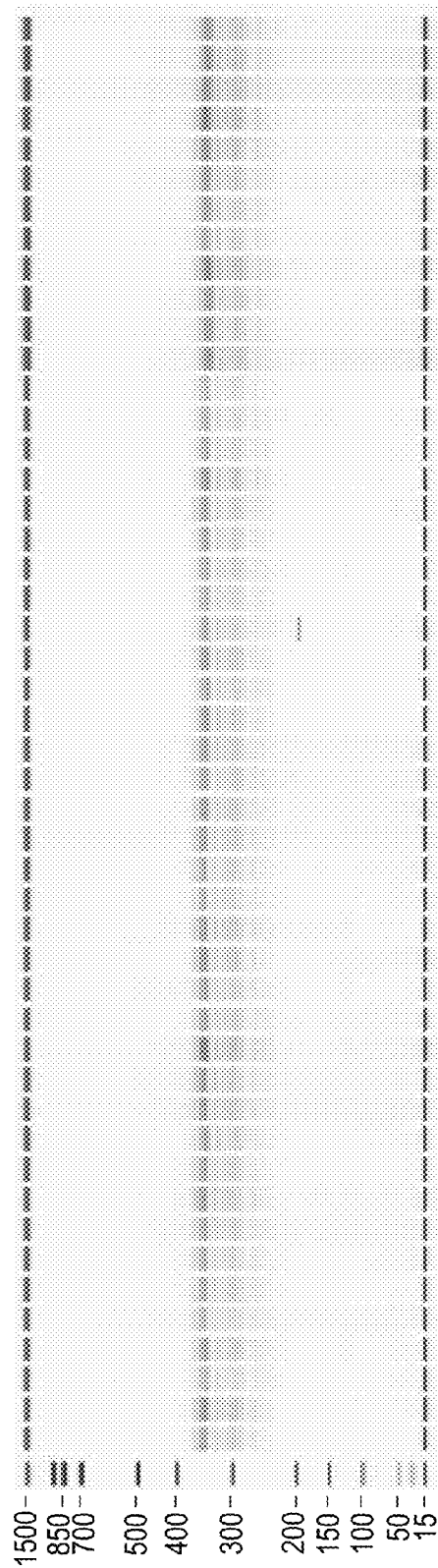
FIG. 12 shows gel-view electropherograms obtained from 4 Agilent 1K Biolanalyzer chips for each of the individual samples run on the Access Array IFC (Integrated Fluidic Circuit) in Example 4. Each column in the figure shows the size distribution of DNA products in each sample. All samples produce similar distributions of products
Figure 13A:
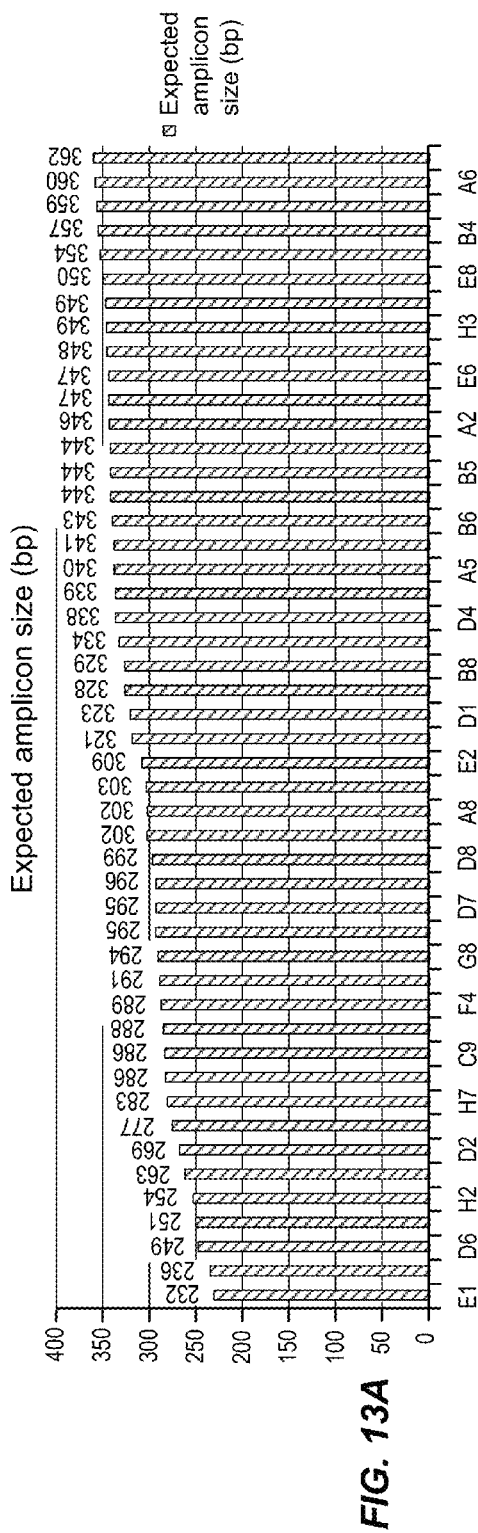
FIG. 13A-13B shows results from Example 4. A) Predicted sizes of all PCR products for this set of target specific primers. B) Electropherogram of one of the sample pools obtained from the Access Array IFC. Distribution of product size within a single product pool. All products fall within the predicted size range shown in (B).
Figure 13B:
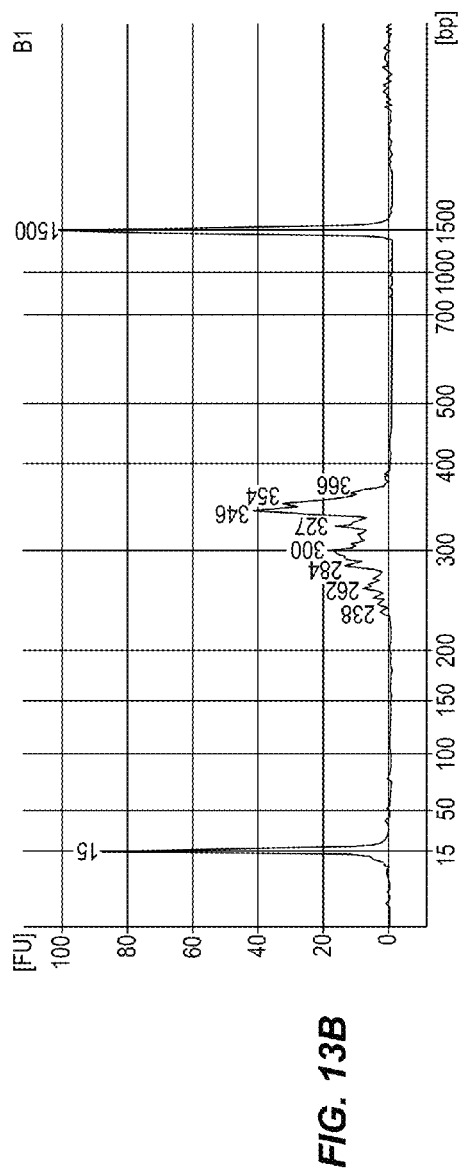

1 µl of each PCR product pool for each sample was taken and loaded onto an Agilent 1K Bioanalyzer chip. FIG. 12 shows the electropherograms from each of the 48 individual product pools. FIG. 13 shows the distribution of product size within a single product pool. All products fall within the predicted size range, and there is no evidence of any small-sized PCR by-products.

PCR Products for each sample were pooled based on concentrations calculated from the Agilent Bioanalyzer traces. The product pool was purified using AMPure beads (Agencourt) according to the manufacturer's instructions.

The purified product pool was subjected to emulsion PCR followed by pyrosequencing on a 454 FLX sequencer (Roche Analytical Sciences) according to manufacturer's instructions. The sequence file output by the sequencer was then analyzed for the presence of barcoded PCR products.

Figure 14A:
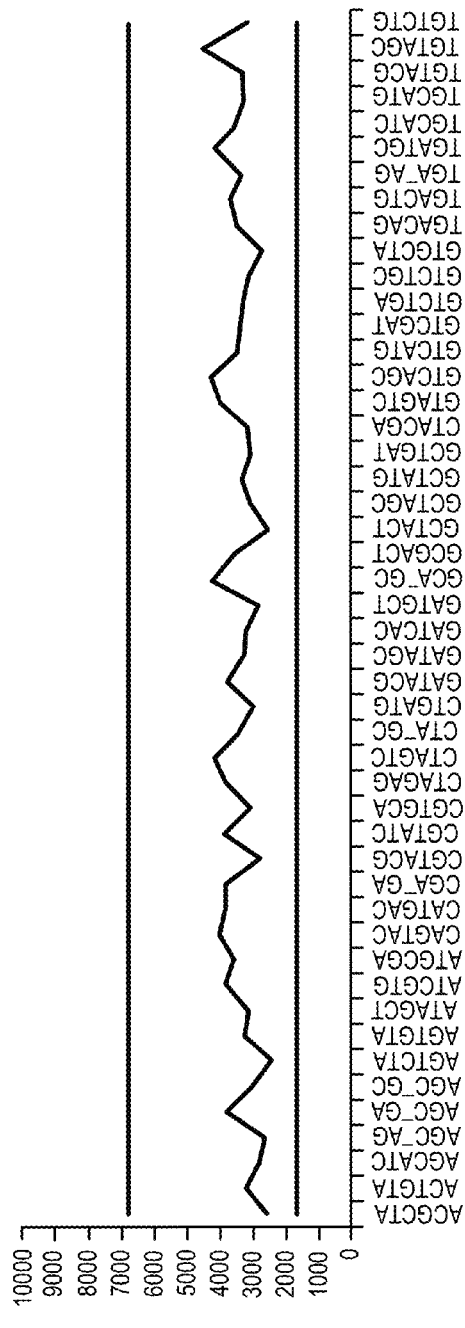
FIG. 14A-14C shows results from Example 4. A) Number of sequences counted per barcode on the 454 sequence run. Upper horizontal line represents 2× average number of counts per barcode. Lower horizontal line represents 50% of average number of counts per barcode. B) Number of sequences counted per amplicon. Each point on the plot represents the number of times the sequence for an individual chamber on the Access Array IFC were measured on the sequencer. Triangular points represent PCR reactions with greater than 2× the average representation. Dark grey points represent PCR reactions with less than 0.5× the average representation. C) Frequency distribution of amplicon representation. The dark grey line represents the number of amplicons present at a given representation. The light grey line represents the number of reads that would be measured at a given coverage (e.g. 98% at 20× coverage). Percentage of amplicons within 2-fold of average: 95.8%; percentage of amplicons within 5-fold of average: 99.7%.

The number of sequences obtained for each barcode were counted, and plotted (FIG. 14(A)). On average ~3400 sequences were counted for each barcode. All samples were represented at >50% of average and <2-fold of average.

Figure 14B:
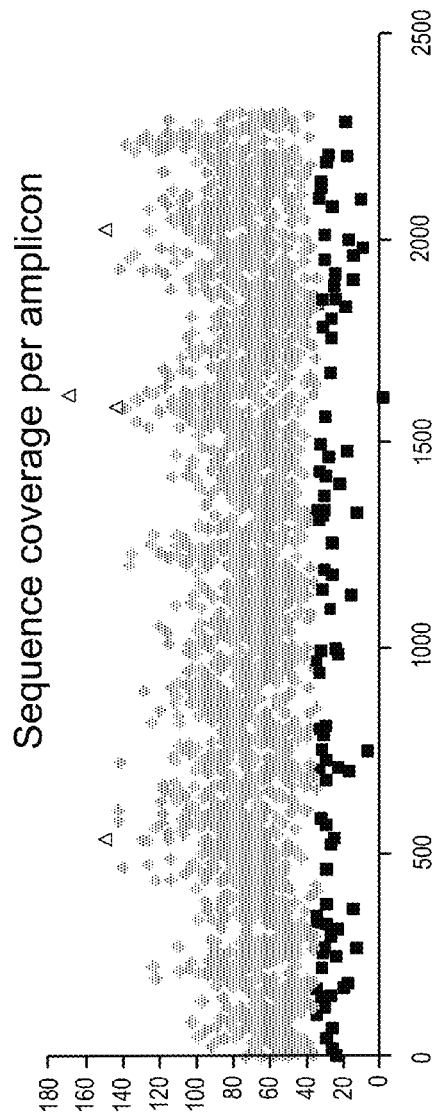
Figure 14C:
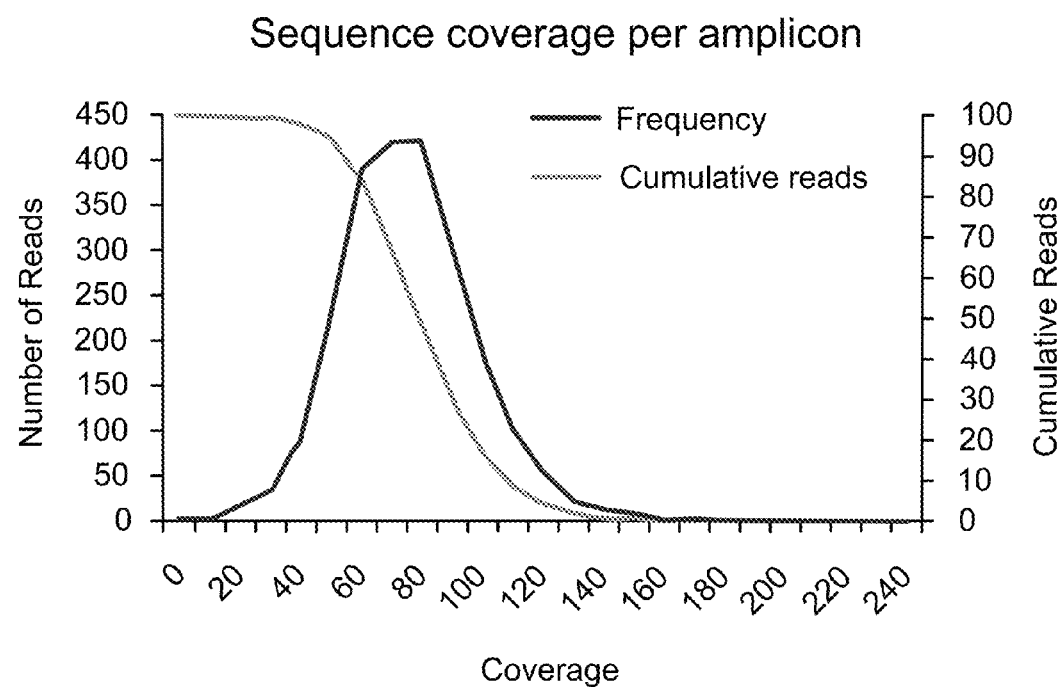

The number of sequences counted for each individual PCR product in each sample were then analyzed (FIG. 14(B)). Only one of 2304 PCR products was not observed on the sequencer. The vast majority of sequences were present at >50% of average and <2 fold of average. 2303/2304 products were counted >5 times. FIG. 14(C) shows the distribution of PCR products from all 2304 PCR reactions in the Access Array IFC. >95% of sequences were measured between 50% and 2 fold of the average coverage. >99% of sequences were measured between 50% and 2 fold of the average coverage.

Example 5

Figure 15A:
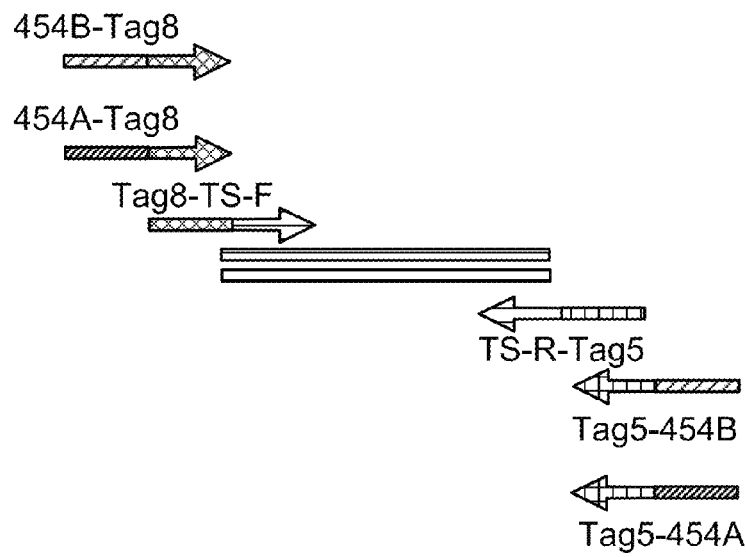
FIG. 15A-15B shows an example of a multi-primer reaction set-up using 4 outer primers with different combinations of primer binding site and nucleotide tags. (Example 5.) A) Two forward barcode primers (454B-BC-Tag8, 454A-BC-Tag8 and two reverse barcode primers (454A-BC-Tag5, 454B-BC-Tag8) are combined with one inner primer pair (Tag8-TSF and Tag5-TSR). B) The two major PCR products formed from this PCR reaction. PCR products containing 454-A Tag8 and 454A-Tag5 at each end or 454B-Tag8 and 454B-Tag5 at each end do not produce significant PCR products due to PCR suppression

Multi-Primer Amplification Using Four Outer Primers with Different Combinations of Primer Binding Site and Nucleotide Tags Sets of primer pairs were designed to amplify specific regions from the EGFR and MET genes. These were then combined in an Access Array IFC with human genomic DNA and four outer primers (FIG. 15).

Preparation of Reaction Mixtures

Primers were synthesized by Eurofins MWG Operon at 10 nmol scale and provided resuspended in water at a concentration of 100 µM. The forward and reverse primer for each region in Table 9 were combined in separate wells in a 96-well PCR plate (USA scientific) to a final concentration of 1 µM of each primer in PCR-quality water (Teknova) containing 0.05% Tween-20.

TABLE 9

| Assay | Forward Primer | Forward Primer SEQ ID NO. | Reverse Primer | Reverse Primer SEQ ID NO. |
|---|---|---|---|---|
| EGFR_Exon3 | ACACTGACGACAT GGTTCTACATTCTT AGACCATCCAGGA GGTG | (SEQ ID NO: 261) | TACGGTAGCAGAGACTTGG TCTCCAGCCTCTCACCCTG TAAA | (SEQ ID NO: 262) |

TABLE 9-continued

| Assay | Forward Primer | Forward Primer SEQ ID NO. | Reverse Primer | Reverse Primer SEQ ID NO. |
|---|---|---|---|---|
| EGFR_Exon4 | ACACTGACGACATGGTTCTACAAGCTGGAAAGAGTGCTCACC | (SEQ ID NO: 263) | TACGGTAGCAGAGACTTGGTCTTAGGAGCTGGAGGCAGAGAT | (SEQ ID NO: 264) |
| EGFR_Exon5 | ACACTGACGACATGGTTCTACAGCGTCATCAGTTTCTCATCATT | (SEQ ID NO: 265) | TACGGTAGCAGAGACTTGGTCTACATGGGTCTGAGGCTGTTC | (SEQ ID NO: 266) |
| EGFR_Exon6 | ACACTGACGACATGGTTCTACACCCTGGGAAATGATCCTACC | (SEQ ID NO: 267) | TACGGTAGCAGAGACTTGGTCTTCTTACCAGGCAGTCGCTCT | (SEQ ID NO: 268) |
| EGFR_Exon7 | ACACTGACGACATGGTTCTACACCAGCGTGTCCTCTCTCCT | (SEQ ID NO: 269) | TACGGTAGCAGAGACTTGGTCTGACAAGGATGCCTGACCAGT | (SEQ ID NO: 270) |
| EGFR_Exon8 | ACACTGACGACATGGTTCTACACAAAGGAGGATGGAGCCTTTC | (SEQ ID NO: 271) | TACGGTAGCAGAGACTTGGTCTGATGTGTTCCTTTGGAGGTGG | (SEQ ID NO: 272) |
| EGFR_Exon9 | ACACTGACGACATGGTTCTACATCCAACAAATGTGAACGGAAT | (SEQ ID NO: 273) | TACGGTAGCAGAGACTTGGTCTCAAGCAACTGAACCTGTGACTC | (SEQ ID NO: 274) |
| EGFR_Exon10 | ACACTGACGACATGGTTCTACAGATCAATAATCACCCTGTTGTTTG | (SEQ ID NO: 275) | TACGGTAGCAGAGACTTGGTCTTTCCAAGGGAACAGGAAATATG | (SEQ ID NO: 276) |
| EGFR_Exon11 | ACACTGACGACATGGTTCTACATCCTACGTGGTGTGTGTCTGA | (SEQ ID NO: 277) | TACGGTAGCAGAGACTTGGTCTGCTTTGGCTGTGGTCAACTT | (SEQ ID NO: 278) |
| EGFR_Exon12 | ACACTGACGACATGGTTCTACACCACATGATTTTCTTCTCTCCA | (SEQ ID NO: 279) | TACGGTAGCAGAGACTTGGTCTCGGTGACTTACTGCAGCTGTT | (SEQ ID NO: 280) |
| EGFR_Exon13 | ACACTGACGACATGGTTCTACAGCTCTGTCACTGACTGCTGTG | (SEQ ID NO: 281) | TACGGTAGCAGAGACTTGGTCTGCTATAACAACAACCTGGAGCCT | (SEQ ID NO: 282) |
| EGFR_Exon14 | ACACTGACGACATGGTTCTACAGCTGACGGGTTTCCTCTTC | (SEQ ID NO: 283) | TACGGTAGCAGAGACTTGGTCTGACGTGGATAGCAGCAAGG | (SEQ ID NO: 284) |
| EGFR_Exon15 | ACACTGACGACATGGTTCTACAGCATGAACATTTTTCTCCACCT | (SEQ ID NO: 285) | TACGGTAGCAGAGACTTGGTCTTTCTGTTCTCCTTCACTTTCCAC | (SEQ ID NO: 286) |
| EGFR_Exon16 | ACACTGACGACATGGTTCTACATTTCTCTTTCACTTCCTACAGATGC | (SEQ ID NO: 287) | TACGGTAGCAGAGACTTGGTCTCCACAGCAGTGTGGTCATTC | (SEQ ID NO: 288) |
| EGFR_Exon17 | ACACTGACGACATGGTTCTACATGGAATCTGTCAGCAACCTC | (SEQ ID NO: 289) | TACGGTAGCAGAGACTTGGTCTCCCAGGACTGGCACTCA | (SEQ ID NO: 290) |
| EGFR_Exon18 | ACACTGACGACATGGTTCTACAGCTGAGGTGACCCTTGTCTC | (SEQ ID NO: 291) | TACGGTAGCAGAGACTTGGTCTCCCACCAGACCATGAGAGG | (SEQ ID NO: 292) |

TABLE 9-continued

| Assay | Forward Primer | Forward Primer SEQ ID NO. | Reverse Primer | Reverse Primer SEQ ID NO. |
|---|---|---|---|---|
| EGFR_Exon19 | ACACTGACGACAT GGTTCTACATCAC AATTGCCAGTTAA CGTCT | (SEQ ID NO: 293) | TACGGTAGCAGAGACTTGG TCTCCACACAGCAAAGCAG AAAC | (SEQ ID NO: 294) |
| EGFR_Exon20 | ACACTGACGACAT GGTTCTACACCAC ACTGACGTGCCTC TC | (SEQ ID NO: 295) | TACGGTAGCAGAGACTTGG TCTCCGTATCTCCCTTCCCT GAT | (SEQ ID NO: 296) |
| EGFR_Exon21 | ACACTGACGACAT GGTTCTACACCTC ACAGCAGGGTCTT CTC | (SEQ ID NO: 297) | TACGGTAGCAGAGACTTGG TCTCTGACCTAAAGCCACC TCCTT | (SEQ ID NO: 298) |
| EGFR_Exon22 | ACACTGACGACAT GGTTCTACACACT GCCTCATCTCTCAC CA | (SEQ ID NO: 299) | TACGGTAGCAGAGACTTGG TCTCCAGCTTGGCCTCAGT ACA | (SEQ ID NO: 300) |
| EGFR_Exon23 | ACACTGACGACAT GGTTCTACACATG ATCCCACTGCCTTC TT | (SEQ ID NO: 301) | TACGGTAGCAGAGACTTGG TCTAGTGTGGACAGACCCA CCA | (SEQ ID NO: 302) |
| EGFR_Exon24 | ACACTGACGACAT GGTTCTACATTCCA GTGTTCTAATTGCA CTGTT | (SEQ ID NO: 303) | TACGGTAGCAGAGACTTGG TCTGAGGGACTCTTCCCAA TGGA | (SEQ ID NO: 304) |
| EGFR_Exon25 | ACACTGACGACAT GGTTCTACACTAA TAGCCTCAAAATC TCTGCAC | (SEQ ID NO: 305) | TACGGTAGCAGAGACTTGG TCTTTTGTTCAAATGAGTA GACACAGC | (SEQ ID NO: 306) |
| EGFR_Exon26 | ACACTGACGACAT GGTTCTACACATTC CATGGGCAACTTC TC | (SEQ ID NO: 307) | TACGGTAGCAGAGACTTGG TCTTTCTGGCTTATAAGGT GTTCATACA | (SEQ ID NO: 308) |
| EGFR_Exon27 | ACACTGACGACAT GGTTCTACACCTTC CCTCATTTCCTCCT G | (SEQ ID NO: 309) | TACGGTAGCAGAGACTTGG TCTTCCAGACAAGCCACTC ACC | (SEQ ID NO: 310) |
| EGFR_Exon28-1 | ACACTGACGACAT GGTTCTACAcctctgat ttctttccactttca | (SEQ ID NO: 311) | TACGGTAGCAGAGACTTGG TCTCTAATTTGGTGGCTGC CTTT | (SEQ ID NO: 312) |
| EGFR_Exon28-2 | ACACTGACGACAT GGTTCTACATGTC AACAGCACATTCG ACAG | (SEQ ID NO: 313) | TACGGTAGCAGAGACTTGG TCTGGTCCTGGGTATCGAA AGAGT | (SEQ ID NO: 314) |
| EGFR_Exon2 | ACACTGACGACAT GGTTCTACATTTCT TCCAGTTTGCCAA GG | (SEQ ID NO: 315) | TACGGTAGCAGAGACTTGG TCTAGGAAAATCAAAGTCA CCAACC | (SEQ ID NO: 316) |
| MET_Exon1-1 | ACACTGACGACAT GGTTCTACACTCTC GCCTTGAACCTGTT T | (SEQ ID NO: 317) | TACGGTAGCAGAGACTTGG TCTCAGCACAGGCCCAGTC TT | (SEQ ID NO: 318) |
| MET_Exon1-2 | ACACTGACGACAT GGTTCTACATTCCT TGGTGCCACTAAC TACA | (SEQ ID NO: 319) | TACGGTAGCAGAGACTTGG TCTGGGAGAATATGCAGTG AACCTC | (SEQ ID NO: 320) |
| MET_Exon2 | ACACTGACGACAT GGTTCTACATGGA TTCACATTAACTCT ATGACCA | (SEQ ID NO: 321) | TACGGTAGCAGAGACTTGG TCTTTGCACAATACCAGAT AGAACAGAC | (SEQ ID NO: 322) |

TABLE 9-continued

| Assay | Forward Primer | Forward Primer SEQ ID NO. | Reverse Primer | Reverse Primer SEQ ID NO. |
|---|---|---|---|---|
| MET_Exon3 | ACACTGACGACATGGTTCTACATGAGCTTGTTGGAATAAGGATG | (SEQ ID NO: 323) | TACGGTAGCAGAGACTTGGTCTCGTCTATGGAAATTCCCTGTG | (SEQ ID NO: 324) |
| MET_Exon4 | ACACTGACGACATGGTTCTACAGAAGCTCTTTCCACCCCTTC | (SEQ ID NO: 325) | TACGGTAGCAGAGACTTGGTCTTGCCAGCTGTTAGAGATTCCT | (SEQ ID NO: 326) |
| MET_Exon5 | ACACTGACGACATGGTTCTACATGTCCTTGTAGGTTTTCCCAAA | (SEQ ID NO: 327) | TACGGTAGCAGAGACTTGGTCTCCCCAGCAAAGCATTTTAAG | (SEQ ID NO: 328) |
| MET_Exon6 | ACACTGACGACATGGTTCTACAGAAAATTCCTTGGATTTGTCATG | (SEQ ID NO: 329) | TACGGTAGCAGAGACTTGGTCTCATGATAGGATAGAATCTTCCTTACCA | (SEQ ID NO: 330) |
| MET_Exon7 | ACACTGACGACATGGTTCTACAGTTTTGTTTTTATCTCCCCTCCA | (SEQ ID NO: 331) | TACGGTAGCAGAGACTTGGTCTTTCAAATTGACAGATGCAACAA | (SEQ ID NO: 332) |
| MET_Exon8 | ACACTGACGACATGGTTCTACAGGAACCATTGAGTTATATCCTTTTG | (SEQ ID NO: 333) | TACGGTAGCAGAGACTTGGTCTTTGTTTTCTTATACCCATCAGAAGC | (SEQ ID NO: 334) |
| MET_Exon9 | ACACTGACGACATGGTTCTACATTGGTGGAAAGAACCTCTCAA | (SEQ ID NO: 335) | TACGGTAGCAGAGACTTGGTCTCAGGTACCATGAAAGCCACA | (SEQ ID NO: 336) |
| MET_Exon10 | ACACTGACGACATGGTTCTACATGTTGCCAAGCTGTATTCTGTT | (SEQ ID NO: 337) | TACGGTAGCAGAGACTTGGTCTTTTGAGCTGATGATTTAAGACAGTG | (SEQ ID NO: 338) |
| MET_Exon12 | ACACTGACGACATGGTTCTACAGGACCCAAAGTGCTACAACC | (SEQ ID NO: 339) | TACGGTAGCAGAGACTTGGTCTCAAGAATCGACGACAATCTTAAAC | (SEQ ID NO: 340) |
| MET_Exon13 | ACACTGACGACATGGTTCTACAGCCCATGATAGCCGTCTTTA | (SEQ ID NO: 341) | TACGGTAGCAGAGACTTGGTCTCAACAATGTCACAACCCACTG | (SEQ ID NO: 342) |
| MET_Exon14 | ACACTGACGACATGGTTCTACACCTTCATCTTACAGATCAGTTTCCT | (SEQ ID NO: 343) | TACGGTAGCAGAGACTTGGTCTGCTTACTGGAAAATCGTATTTAACAAA | (SEQ ID NO: 344) |
| MET_Exon15 | ACACTGACGACATGGTTCTACAACGCAGTGCTAACCAAGTTCT | (SEQ ID NO: 345) | TACGGTAGCAGAGACTTGGTCTTCCACAAGGGGAAAGTGTAAA | (SEQ ID NO: 346) |
| MET_Exon16 | ACACTGACGACATGGTTCTACATGTCTCCACCACTGGATTTCT | (SEQ ID NO: 347) | TACGGTAGCAGAGACTTGGTCTGGCTTACAGCTAGTTTGCCAGT | (SEQ ID NO: 348) |
| MET_Exon17 | ACACTGACGACATGGTTCTACATGCTTTTCTAACTCTCTTTGACTGC | (SEQ ID NO: 349) | TACGGTAGCAGAGACTTGGTCTTCCTCCTTGTCACTTAATTTGGA | (SEQ ID NO: 350) |
| MET_Exon18 | ACACTGACGACATGGTTCTACATTCTATTTCAGCCACGGGTAA | (SEQ ID NO: 351) | TACGGTAGCAGAGACTTGGTCTAGAGGAGAAACTCAGAGATAACCAA | (SEQ ID NO: 352) |

TABLE 9-continued

| Assay | Forward Primer | Forward Primer SEQ ID NO. | Reverse Primer | Reverse Primer SEQ ID NO. |
|---|---|---|---|---|
| MET_Exon19 | ACACTGACGACAT GGTTCTACACTCA CCTCATCTGTCCTG TTTCT | (SEQ ID NO: 353) | TACGGTAGCAGAGACTTGG TCTGGCATTTCTGTAAAAG TAAAGAACG | (SEQ ID NO: 354) |
| MET_Exon20 | ACACTGACGACAT GGTTCTACACCTG CCTTCAAAGGGTC TCT | (SEQ ID NO: 355) | TACGGTAGCAGAGACTTGG TCTGTGTGGACTGTTGCTT TGACA | (SEQ ID NO: 356) |

A single human Genomic DNA sample (Coriell NA10830) was resuspended at 50 ng/µl in low-EDTA TE buffer (Teknova) and prepared for PCR as follows.

A pre-sample mixture was prepared as follows:

TABLE 10

| Pre-sample mixture | Volume per sample (µl) | Volume for 64 samples (µl) |
|---|---|---|
| Faststart High Fidelity reaction Buffer with MgCl$_2$ | 0.5 | 32 |
| DMSO | 0.1 | 6.4 |
| PCR-Grade Nucleotide Mixture | 0.1 | 6.4 |
| Faststart High-Fidelity Enzyme Blend (Roche 04 738 292 001) | 0.05 | 3.2 |
| 20x Access Array Loading Reagent (PN: 100-0883) | 0.25 | 16 |
| PCR-Grade water | 0.5 | 32 |
| Total | 2.5 | 160 |

For each sample replicate, a sample mixture containing forward and reverse barcode primers, genomic DNA and pre-sample mix was prepared in an individual well in a 96-well PCR plate.

TABLE 11

| Sample Mixture | Volume (µl) |
|---|---|
| Pre-sample Mixture | 2 |
| 4 µM forward barcode primer | 0.5 |
| 4 µm reverse barcode primer | 0.5 |
| Genomic DNA (50 ng/µl) | 1 |
| PCR-grade water | 1 |

Four replicate samples were prepared by mixing each sample with one pair of barcode primers selected from Table 12.

TABLE 12

| | Reverse barcode primer (454B-BC#-CS1) | Reverse barcode primer SEQ ID NO. | Forward barcode primer (454A-BC#-CS2) | Forward barcode primer SEQ ID NO. |
|---|---|---|---|---|
| 1 | GCCTTGCCAGCCC GCTCAGGCATGC TACGGTAGCAGA GACTTGGTCT | (SEQ ID NO: 357) | GCCTCCCTCGCGCC ATCAGGCATGCAC ACTGACGACATGGT TCTACA | (SEQ ID NO: 358) |
| 2 | GCCTTGCCAGCCC GCTCAGCGTACG TACGGTAGCAGA GACTTGGTCT | (SEQ ID NO: 359) | GCCTCCCTCGCGCC ATCAGCGTACGAC ACTGACGACATGGT TCTACA | (SEQ ID NO: 360) |
| 3 | GCCTTGCCAGCCC GCTCAGGTCAGC TACGGTAGCAGA GACTTGGTCT | (SEQ ID NO: 361) | GCCTCCCTCGCGCC ATCAGGTCAGCAC ACTGACGACATGGT TCTACA | (SEQ ID NO: 362) |
| 4 | GCCTTGCCAGCCC GCTCAGAGCTGC TACGGTAGCAGA GACTTGGTCT | (SEQ ID NO: 363) | GCCTCCCTCGCGCC ATCAGAGCTGCAC ACTGACGACATGGT TCTACA | (SEQ ID NO: 364) |
| 5 | GCCTTGCCAGCCC GCTCAGTGCATCT ACGGTAGCAGAG ACTTGGTCT | (SEQ ID NO: 365) | GCCTCCCTCGCGCC ATCAGTGCATCACA CTGACGACATGGTT CTACA | (SEQ ID NO: 366) |
| 6 | GCCTTGCCAGCCC GCTCAGCTGATGT ACGGTAGCAGAG ACTTGGTCT | (SEQ ID NO: 367) | GCCTCCCTCGCGCC ATCAGCTGATGACA CTGACGACATGGTT CTACA | (SEQ ID NO: 368) |

TABLE 12-continued

| Reverse barcode primer (454B-BC#-CS1) | Reverse barcode primer SEQ ID NO. | Forward barcode primer (454A-BC#-CS2) | Forward barcode primer SEQ ID NO. |
|---|---|---|---|
| 7 GCCTTGCCAGCCCGCTCAGGTAGTCTACGGTAGCAGAGACTTGGTCT | (SEQ ID NO: 369) | GCCTCCCTCGCGCCATCAGGTAGTCACACTGACGACATGGTTCTACA | (SEQ ID NO: 370) |
| 8 GCCTTGCCAGCCCGCTCAGGTCGATTACGGTAGCAGAGACTTGGTCT | (SEQ ID NO: 371) | GCCTCCCTCGCGCCATCAGGTCGATACACTGACGACATGGTTCTACA | (SEQ ID NO: 372) |
| 9 GCCTTGCCAGCCCGCTCAGGATACGTACGGTAGCAGAGACTTGGTCT | (SEQ ID NO: 373) | GCCTCCCTCGCGCCATCAGGATACGACACTGACGACATGGTCTACA | (SEQ ID NO: 374) |
| 10 GCCTTGCCAGCCCGCTCAGTGATGCTACGGTAGCAGAGACTTGGTCT | (SEQ ID NO: 375) | GCCTCCCTCGCGCCATCAGTGATGCACACTGACGACATGGTTCTACA | (SEQ ID NO: 376) |
| 11 GCCTTGCCAGCCCGCTCAGAGCTGATACGGTAGCAGAGACTTGGTCT | (SEQ ID NO: 377) | GCCTCCCTCGCGCCATCAGAGCTGAACACTGACGACATGGTCTACA | (SEQ ID NO: 378) |
| 12 GCCTTGCCAGCCCGCTCAGACTGTATACGGTAGCAGAGACTTGGTCT | (SEQ ID NO: 379) | GCCTCCCTCGCGCCATCAGACTGTAACACTGACGACATGGTTCTACA | (SEQ ID NO: 380) |
| 13 GCCTTGCCAGCCCGCTCAGTGCATGTACGGTAGCAGAGACTTGGTCT | (SEQ ID NO: 381) | GCCTCCCTCGCGCCATCAGTGCATGACACTGACGACATGGTTCTACA | (SEQ ID NO: 382) |
| 14 GCCTTGCCAGCCCGCTCAGAGTCTATACGGTAGCAGAGACTTGGTCT | (SEQ ID NO: 383) | GCCTCCCTCGCGCCATCAGAGTCTAACACTGACGACATGGTTCTACA | (SEQ ID NO: 384) |
| 15 GCCTTGCCAGCCCGCTCAGTGTCTGTACGGTAGCAGAGACTTGGTCT | (SEQ ID NO:385) | GCCTCCCTCGCGCCATCAGTGTCTGACACTGACGACATGGTTCTACA | (SEQ ID NO: 386) |
| 16 GCCTTGCCAGCCCGCTCAGGCTAGCTACGGTAGCAGAGACTTGGTCT | (SEQ ID NO: 387) | GCCTCCCTCGCGCCATCAGGCTAGCACACTGACGACATGGTCTACA | (SEQ ID NO: 388) |

Running the Access Array IFC

The containment and interface accumulator reservoirs were filled with 300 µl of Control Line Fluid (Fluidigm PN 89000020), and the H1-H4 reagent wells were loaded with 500 µl of 0.05% Tween-20 in PCR-grade water prior to Access Array IFC loading. 5 µl of each sample mixture was loaded into the sample ports, and 5 µl of each primer mixture was loaded into the primer inlets on the Access Array IFC.

The Access Array IFC was thermal cycled and imaged using an IFC Stand-Alone Thermal Cycler (Fluidigm Corporation). The thermal cycling protocol contains a thermal mix step [50° C. for 2 min, 70° C. for 20 min], a hotstart step [95° C. for 10 min], a 35 cycle PCR strategy [2 cycles of 95° C. for 15 sec and 60° C. for 4 min, 33 cycles of 95° C. for 15 sec, 60° C. for 15 sec, 72° C. for 1 min, and an elongation step [72° C. for 3 min].

After amplification, the PCR products were harvested from the Access Array IFC using the Post-PCR IFC Loader AX. Before harvesting, each sample port was filled with 2 µl of 0.05% Tween-20. Residual solution was removed from the H1-H4 reagent wells, and they were refilled with 600 µl of 1× Access Array Harvesting Reagent (0.05% tween-20). After harvesting each sample port became a PCR product outlet that contained 10 µl (±10%) of 48 pooled PCR products. The pooled PCR products were removed from the Access Array IFC and stored in a microtiter plate at 4° C.

PCR products for each sample were pooled based on concentrations calculated from the Agilent Bioanalyzer traces. The purified product pool was subjected to emulsion PCR followed by pyrosequencing on a 454 FLX sequencer (Roche Analytical Sciences) according to manufacturer's instructions. Emulsion PCR reactions were run with beads containing both A and B primer sequences attached, enabling sequence reads for both strands of the amplicon.

Figure 15B:
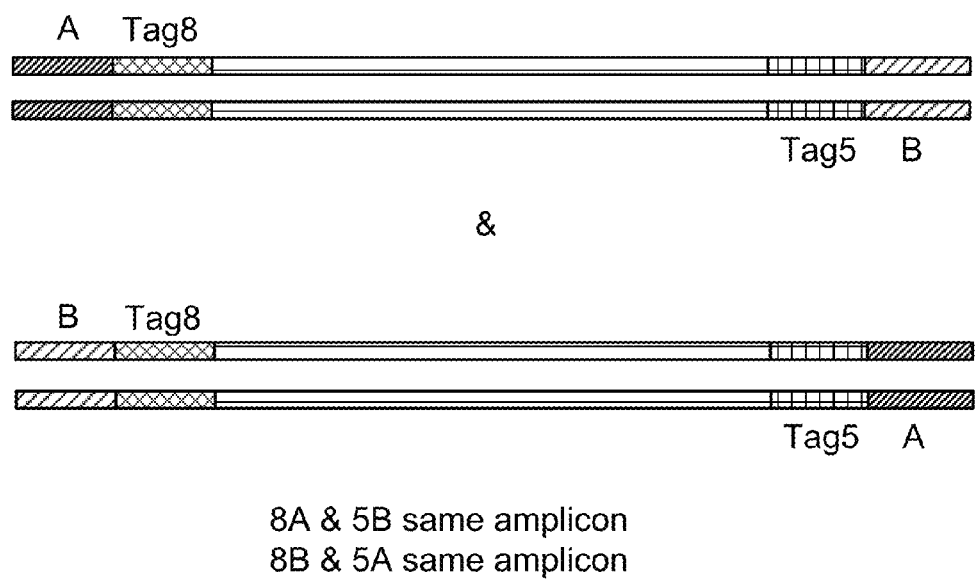
Figure 16A:
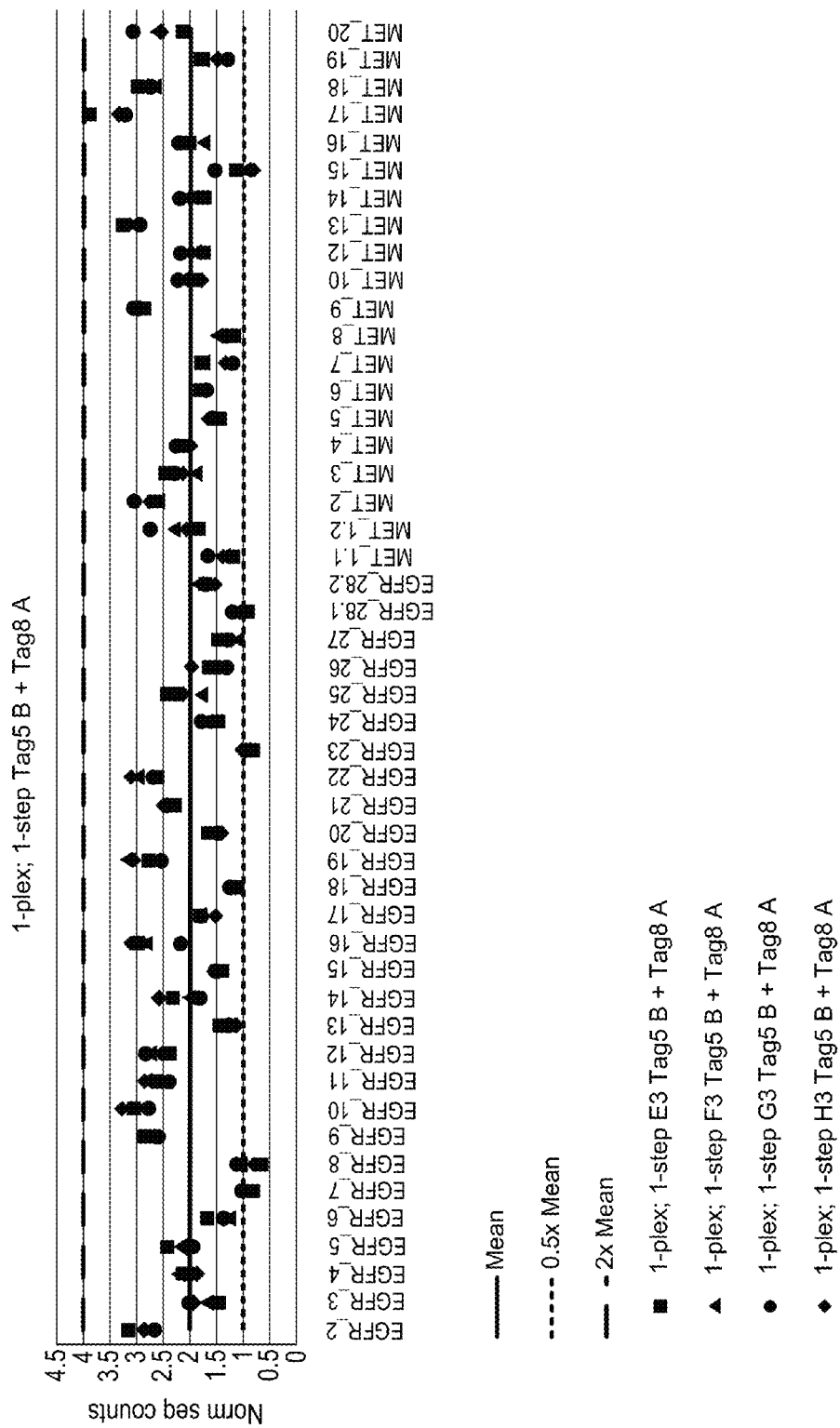
FIG. 16A-16B shows the representation of each of the primer sequences in each of the samples for each of the amplicons in FIG. 15B. The number of sequences counted per amplicon were normalized to the average number of counts per amplicon within a sample. The normalized counts for an individual amplicon were summed between the A and B emulsions (A) for Tag5 amplicons in Emulsion A plus Tag 8 amplicons in Emulsion B and (B) for Tag5 amplicons in Emulsion B plus Tag 8 amplicons in Emulsion A. The middle dark grey line represents the average representation of each amplicon. The upper light grey line represents 2× average coverage. The lower light grey line represents 50% of average representation.
Figure 16B:
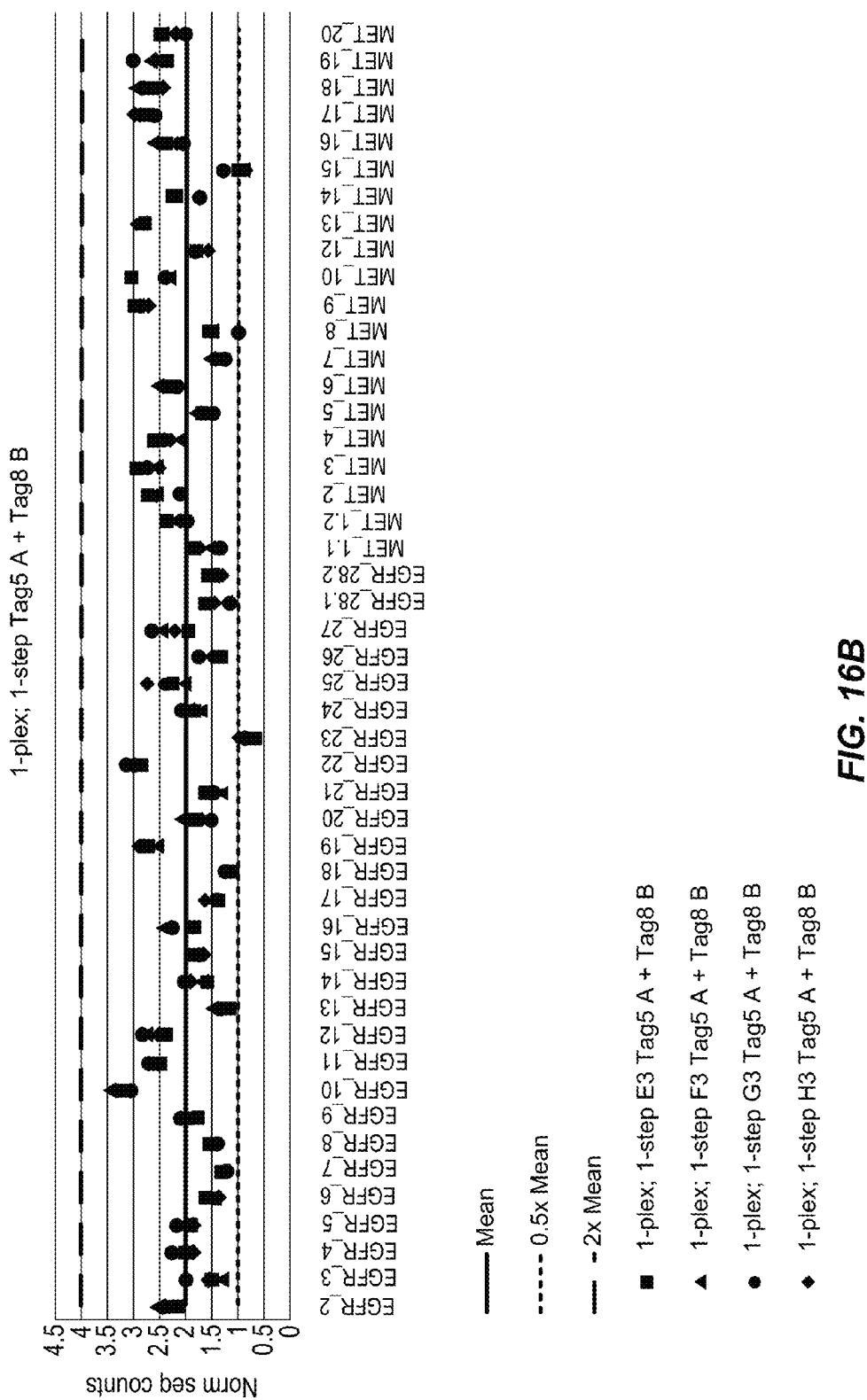

The number of sequences counted for each individual PCR product in each sample were analyzed to demonstrate representation of the PCR products shown in FIG. 15. Sequences could be counted for each of the amplicons shown in FIG. 15B, by summing tag 5 sequences from emulsion A with tag 8 sequences from emulsion B (FIG. 16A) or tag 5 sequences from emulsion B with tag 8 sequences from emulsion A. FIG. 16 shows that representation of all amplicons mostly lies between 2× and 0.5× of average coverage. Furthermore, representation of both amplicons for each primer pair is very similar, although the amplicon represented in FIG. 16B shows less variation within samples.

Example 6

4-Primer Barcoding of Target Nucleic Acids for Illumina DNA Sequencing Using a Microfluidic Device that Permits Recovery of Amplication Products Sequences designed for a 4-primer tagging scheme to be used on the Illumina Genome Analyzer II are shown in Tables 13 and 14. The tag sequence is the inner primer sequence.

TABLE 13

Inner primers

| Tag Sequence | Target-Specific Sequence (Forward) | Oligonucleotide Sequence |
|---|---|---|
| ACACTCTTTCCCTACA CGACGCTCTTCCGAT CT (SEQ ID NO: 389) | ACTGTCCAGCTTT GTGCC (SEQ ID NO: 390) | ACACTCTTTCCCTACA CGACGCTCTTCCGATC TACTGTCCAGCTTTGT GCC (SEQ ID NO: 391) |
| ACACTCTTTCCCTACA CGACGCTCTTCCGAT CT (SEQ ID NO: 392) | GATCATCATAGGA GTTGCATTGTTG (SEQ ID NO: 393) | ACACTCTTTCCCTACA CGACGCTCTTCCGATC TGATCATCATAGGAGT TGCATTGTTG (SEQ ID NO: 394) |

TABLE 13-continued

Inner primers

| Tag Sequence | Target-Specific Sequence (Reverse) | Oligonucleotide Sequence |
|---|---|---|
| CTCGGCATTCCTGCTG AACCGCTCTTCCGAT CT (SEQ ID NO: 395) | TCCTCTGCCTAGG CGTT (SEQ ID NO: 396) | CTCGGCATTCCTGCTG AACCGCTCTTCCGATC TTCCTCTGCCTAGGCG TT (SEQ ID NO: 397) |
| CTCGGCATTCCTGCTG AACCGCTCTTCCGAT CT (SEQ ID NO: 398) | GAAATGTAAATGT GGAGCCAAACA (SEQ ID NO: 399) | CTCGGCATTCCTGCTG AACCGCTCTTCCGATC TGAAATGTAAATGTGG AGCCAAACA (SEQ ID NO: 400) |

TABLE 14

| Barcode Primers | Direction | |
|---|---|---|
| ILMN_PE1sh_F | Forward | AATGATACGGCGACCACCGAGATCTAC ACTCTTTCCCTACACGA (SEQ ID NO: 401) |
| ILMN_PE2sh_R | Reverse | CAAGCAGAAGACGGCATACGAGATCGG TCTCGGCATTCCTGCTGAAC (SEQ ID NO: 402) |

The successful amplification of a PCR product using the 4-primer strategy designed for use on the Illumina GA II sequencer is shown in FIG. 17.

Example 7

Barcoding of Target Nucleic Acids for Titanium Chemistry on the 454 FLX Sequencer (Roche Analytical Sciences)

Table 15 shows forward barcode sequences for use with Titanium chemistry on the 454 FLX Sequencer (Roche Analytical Sciences). Table 16 shows reverse barcode sequences for use with Titanium chemistry on the 454 FLX Sequencer (Roche Analytical Sciences).

TABLE 15

| Well | Barcode | Forward Oligo Name | Forward Oligo sequence | SEQ ID NO. |
|---|---|---|---|---|
| A1 | TI-MID1 | TI-F-MID1-TAG8 | CGTATCGCCTCCCTCGCGCCATCA GACGAGTGCGTACACTGACGACA TGGTTCTACA | (SEQ ID NO: 403) |
| B1 | TI-MID2 | TI-F-MID2-TAG8 | CGTATCGCCTCCCTCGCGCCATCA GACGCTCGACAACACTGACGACA TGGTTCTACA | (SEQ ID NO: 404) |
| C1 | TI-MID3 | TI-F-MID3-TAG8 | CGTATCGCCTCCCTCGCGCCATCA GAGACGCACTCACACTGACGACA TGGTTCTACA | (SEQ ID NO: 405) |
| D1 | TI-MID67 | TI-F-MID67-TAG8 | CGTATCGCCTCCCTCGCGCCATCA GTCGATAGTGAACACTGACGACA TGGTTCTACA | (SEQ ID NO: 406) |
| E1 | TI-MID5 | TI-F-MID5-TAG8 | CGTATCGCCTCCCTCGCGCCATCA GATCAGACACGACACTGACGACA TGGTTCTACA | (SEQ ID NO: 407) |
| F1 | TI-MID6 | TI-F-MID6-TAG8 | CGTATCGCCTCCCTCGCGCCATCA GATATCGCGAGACACTGACGACA TGGTTCTACA | (SEQ ID NO: 408) |

TABLE 15-continued

| Well | Barcode | Forward Oligo Name | Forward Oligo sequence | SEQ ID NO. |
|---|---|---|---|---|
| G1 | TI-MID7 | TI-F-MID7-TAG8 | CGTATCGCCTCCCTCGCGCCATCAGCGTGTCTCTAACACTGACGACATGGTTCTACA | (SEQ ID NO: 409) |
| H1 | TI-MID8 | TI-F-MID8-TAG8 | CGTATCGCCTCCCTCGCGCCATCAGCTCGCGTGTCACACTGACGACATGGTTCTACA | (SEQ ID NO: 410) |
| A2 | TI-MID10 | TI-F-MID10-TAG8 | CGTATCGCCTCCCTCGCGCCATCAGTCTCTATGCGACACTGACGACATGGTTCTACA | (SEQ ID NO: 411) |
| B2 | TI-MID11 | TI-F-MID11-TAG8 | CGTATCGCCTCCCTCGCGCCATCAGTGATACGTCTACACTGACGACATGGTTCTACA | (SEQ ID NO: 412) |
| C2 | TI-MID13 | TI-F-MID13-TAG8 | CGTATCGCCTCCCTCGCGCCATCAGCATAGTAGTGACACTGACGACATGGTTCTACA | (SEQ ID NO: 413) |
| D2 | TI-MID14 | TI-F-MID14-TAG8 | CGTATCGCCTCCCTCGCGCCATCAGCGAGAGATACACACTGACGACATGGTTCTACA | (SEQ ID NO: 414) |
| E2 | TI-MID15 | TI-F-MID15-TAG8 | CGTATCGCCTCCCTCGCGCCATCAGATACGACGTAACACTGACGACATGGTTCTACA | (SEQ ID NO: 415) |
| F2 | TI-MID16 | TI-F-MID16-TAG8 | CGTATCGCCTCCCTCGCGCCATCAGTCACGTACTAACACTGACGACATGGTTCTACA | (SEQ ID NO: 416) |
| G2 | TI-MID17 | TI-F-MID17-TAG8 | CGTATCGCCTCCCTCGCGCCATCAGCGTCTAGTACACACTGACGACATGGTTCTACA | (SEQ ID NO: 417) |
| H2 | TI-MID18 | TI-F-MID18-TAG8 | CGTATCGCCTCCCTCGCGCCATCAGTCTACGTAGCACACTGACGACATGGTTCTACA | (SEQ ID NO: 418) |
| A3 | TI-MID19 | TI-F-MID19-TAG8 | CGTATCGCCTCCCTCGCGCCATCAGTGTACTACTCACACTGACGACATGGTTCTACA | (SEQ ID NO: 419) |
| B3 | TI-MID20 | TI-F-MID20-TAG8 | CGTATCGCCTCCCTCGCGCCATCAGACGACTACAGACACTGACGACATGGTTCTACA | (SEQ ID NO: 420) |
| C3 | TI-MID21 | TI-F-MID21-TAG8 | CGTATCGCCTCCCTCGCGCCATCAGCGTAGACTAGACACTGACGACATGGTTCTACA | (SEQ ID NO: 421) |
| D3 | TI-MID22 | TI-F-MID22-TAG8 | CGTATCGCCTCCCTCGCGCCATCAGTACGAGTATGACACTGACGACATGGTTCTACA | (SEQ ID NO: 422) |
| E3 | TI-MID23 | TI-F-MID23-TAG8 | CGTATCGCCTCCCTCGCGCCATCAGTACTCTCGTGACACTGACGACATGGTTCTACA | (SEQ ID NO: 423) |
| F3 | TI-MID24 | TI-F-MID24-TAG8 | CGTATCGCCTCCCTCGCGCCATCAGTAGAGACGAGACACTGACGACATGGTTCTACA | (SEQ ID NO: 424) |
| G3 | TI-MID25 | TI-F-MID25-TAG8 | CGTATCGCCTCCCTCGCGCCATCAGTCGTCGCTCGACACTGACGACATGGTTCTACA | (SEQ ID NO: 425) |
| H3 | TI-MID26 | TI-F-MID26-TAG8 | CGTATCGCCTCCCTCGCGCCATCAGACATACGCGTACACTGACGACATGGTTCTACA | (SEQ ID NO: 426) |

TABLE 15-continued

| Well | Barcode | Forward Oligo Name | Forward Oligo sequence | SEQ ID NO. |
|---|---|---|---|---|
| A4 | TI-MID27 | TI-F-MID27-TAG8 | CGTATCGCCTCCCTCGCGCCATCAGACGCGAGTATACACTGACGACATGGTTCTACA | (SEQ ID NO: 427) |
| B4 | TI-MID28 | TI-F-MID28-TAG8 | CGTATCGCCTCCCTCGCGCCATCAGACTACTATGTACACTGACGACATGGTTCTACA | (SEQ ID NO: 428) |
| C4 | TI-MID68 | TI-F-MID68-TAG8 | CGTATCGCCTCCCTCGCGCCATCAGTCGCTGCGTAACACTGACGACATGGTTCTACA | (SEQ ID NO: 429) |
| D4 | TI-MID30 | TI-F-MID30-TAG8 | CGTATCGCCTCCCTCGCGCCATCAGAGACTATACTACACTGACGACATGGTTCTACA | (SEQ ID NO: 430) |
| E4 | TI-MID31 | TI-F-MID31-TAG8 | CGTATCGCCTCCCTCGCGCCATCAGAGCGTCGTCTACACTGACGACATGGTTCTACA | (SEQ ID NO: 431) |
| F4 | TI-MID32 | TI-F-MID32-TAG8 | CGTATCGCCTCCCTCGCGCCATCAGAGTACGCTATACACTGACGACATGGTTCTACA | (SEQ ID NO: 432) |
| G4 | TI-MID33 | TI-F-MID33-TAG8 | CGTATCGCCTCCCTCGCGCCATCAGATAGAGTACTACACTGACGACATGGTTCTACA | (SEQ ID NO: 433) |
| H4 | TI-MID34 | TI-F-MID34-TAG8 | CGTATCGCCTCCCTCGCGCCATCAGCACGCTACGTACACTGACGACATGGTTCTACA | (SEQ ID NO: 434) |
| A5 | TI-MID35 | TI-F-MID35-TAG8 | CGTATCGCCTCCCTCGCGCCATCAGCAGTAGACGTACACTGACGACATGGTTCTACA | (SEQ ID NO: 435) |
| B5 | TI-MID36 | TI-F-MID36-TAG8 | CGTATCGCCTCCCTCGCGCCATCAGCGACGTGACTACACTGACGACATGGTTCTACA | (SEQ ID NO: 436) |
| C5 | TI-MID37 | TI-F-MID37-TAG8 | CGTATCGCCTCCCTCGCGCCATCAGTACACACTACACTGACGACATGGTTCTACA | (SEQ ID NO: 437) |
| D5 | TI-MID38 | TI-F-MID38-TAG8 | CGTATCGCCTCCCTCGCGCCATCAGTACACGTGATACACTGACGACATGGTTCTACA | (SEQ ID NO: 438) |
| E5 | TI-MID39 | TI-F-MID39-TAG8 | CGTATCGCCTCCCTCGCGCCATCAGTACAGATCGTACACTGACGACATGGTTCTACA | (SEQ ID NO: 439) |
| F5 | TI-MID40 | TI-F-MID40-TAG8 | CGTATCGCCTCCCTCGCGCCATCAGTACGCTGTCTACACTGACGACATGGTTCTACA | (SEQ ID NO: 440) |
| G5 | TI-MID69 | TI-F-MID69-TAG8 | CGTATCGCCTCCCTCGCGCCATCAGTCTGACGTCAACACTGACGACATGGTTCTACA | (SEQ ID NO: 441) |
| H5 | TI-MID42 | TI-F-MID42-TAG8 | CGTATCGCCTCCCTCGCGCCATCAGTCGATCACGTACACTGACGACATGGTTCTACA | (SEQ ID NO: 442) |
| A6 | TI-MID43 | TI-F-MID43-TAG8 | CGTATCGCCTCCCTCGCGCCATCAGTCGCACTAGTACACTGACGACATGGTTCTACA | (SEQ ID NO: 443) |
| B6 | TI-MID44 | TI-F-MID44-TAG8 | CGTATCGCCTCCCTCGCGCCATCAGTCTAGCGACTACACTGACGACATGGTTCTACA | (SEQ ID NO: 444) |
| C6 | TI-MID45 | TI-F-MID45-TAG8 | CGTATCGCCTCCCTCGCGCCATCAGTCTATACTATACACTGACGACATGGTTCTACA | (SEQ ID NO: 445) |

TABLE 15-continued

| Well | Barcode | Forward Oligo Name | Forward Oligo sequence | SEQ ID NO. |
|---|---|---|---|---|
| D6 | TI-MID46 | TI-F-MID46-TAG8 | CGTATCGCCTCCCTCGCGCCATCA GTGACGTATGTACACTGACGACAT GGTTCTACA | (SEQ ID NO: 446) |
| E6 | TI-MID47 | TI-F-MID47-TAG8 | CGTATCGCCTCCCTCGCGCCATCA GTGTGAGTAGTACACTGACGACA TGGTTCTACA | (SEQ ID NO: 447) |
| F6 | TI-MID48 | TI-F-MID48-TAG8 | CGTATCGCCTCCCTCGCGCCATCA GACAGTATATAACACTGACGACA TGGTTCTACA | (SEQ ID NO: 448) |
| G6 | TI-MID49 | TI-F-MID49-TAG8 | CGTATCGCCTCCCTCGCGCCATCA GACGCGATCGAACACTGACGACA TGGTTCTACA | (SEQ ID NO: 449) |
| H6 | TI-MID50 | TI-F-MID50-TAG8 | CGTATCGCCTCCCTCGCGCCATCA GACTAGCAGTAACACTGACGACA TGGTTCTACA | (SEQ ID NO: 450) |

TABLE 16

| Well | Barcode | Reverse Oligo Name | Reverse Oligo Sequence | SEQ ID NO. |
|---|---|---|---|---|
| A1 | TI-MID1 | TI-R-MID1-TAG5 | CTATGCGCCTTGCCAGCCCGCTCA GACGAGTGCGTTACGGTAGCAGA GACTTGGTCT | (SEQ ID NO: 451) |
| B1 | TI-MID2 | TI-R-MID2-TAG5 | CTATGCGCCTTGCCAGCCCGCTCA GACGCTCGACATACGGTAGCAGA GACTTGGTCT | (SEQ ID NO: 452) |
| C1 | TI-MID3 | TI-R-MID3-TAG5 | CTATGCGCCTTGCCAGCCCGCTCA GAGACGCACTCTACGGTAGCAGA GACTTGGTCT | (SEQ ID NO: 453) |
| D1 | TI-MID67 | TI-R-MID67-TAG5 | CTATGCGCCTTGCCAGCCCGCTCA GTCGATAGTGATACGGTAGCAGA GACTTGGTCT | (SEQ ID NO: 454) |
| E1 | TI-MID5 | TI-R-MID5-TAG5 | CTATGCGCCTTGCCAGCCCGCTCA GATCAGACACGTACGGTAGCAGA GACTTGGTCT | (SEQ ID NO: 455) |
| F1 | TI-MID6 | TI-R-MID6-TAG5 | CTATGCGCCTTGCCAGCCCGCTCA GATATCGCGAGTACGGTAGCAGA GACTTGGTCT | (SEQ ID NO: 456) |
| G1 | TI-MID7 | TI-R-MID7-TAG5 | CTATGCGCCTTGCCAGCCCGCTCA GCGTGTCTCTATACGGTAGCAGAG ACTTGGTCT | (SEQ ID NO: 457) |
| H1 | TI-MID8 | TI-R-MID8-TAG5 | CTATGCGCCTTGCCAGCCCGCTCA GCTCGCGTGTCTACGGTAGCAGA GACTTGGTCT | (SEQ ID NO: 458) |
| A2 | TI-MID10 | TI-R-MID10-TAG5 | CTATGCGCCTTGCCAGCCCGCTCA GTCTCTATGCGTACGGTAGCAGAG ACTTGGTCT | (SEQ ID NO: 459) |
| B2 | TI-MID11 | TI-R-MID11-TAG5 | CTATGCGCCTTGCCAGCCCGCTCA GTGATACGTCTTACGGTAGCAGA GACTTGGTCT | (SEQ ID NO: 460) |
| C2 | TI-MID13 | TI-R-MID13-TAG5 | CTATGCGCCTTGCCAGCCCGCTCA GCATAGTAGTGTACGGTAGCAGA GACTTGGTCT | (SEQ ID NO: 461) |
| D2 | TI-MID14 | TI-R-MID14-TAG5 | CTATGCGCCTTGCCAGCCCGCTCA GCGAGAGATACTACGGTAGCAGA GACTTGGTCT | (SEQ ID NO: 462) |

TABLE 16-continued

| Well | Barcode | Reverse Oligo Name | Reverse Oligo Sequence | SEQ ID NO. |
|---|---|---|---|---|
| E2 | TI-MID15 | TI-R-MID15-TAG5 | CTATGCGCCTTGCCAGCCCGCTCAGATACGACGTATACGGTAGCAGAGACTTGGTCT | (SEQ ID NO: 463) |
| F2 | TI-MID16 | TI-R-MID16-TAG5 | CTATGCGCCTTGCCAGCCCGCTCAGTCACGTACTATACGGTAGCAGAGACTTGGTCT | (SEQ ID NO: 464) |
| G2 | TI-MID17 | TI-R-MID17-TAG5 | CTATGCGCCTTGCCAGCCCGCTCAGCGTCTAGTACTACGGTAGCAGAGACTTGGTCT | (SEQ ID NO: 465) |
| H2 | TI-MID18 | TI-R-MID18-TAG5 | CTATGCGCCTTGCCAGCCCGCTCAGTCTACGTAGCTACGGTAGCAGAGACTTGGTCT | (SEQ ID NO: 466) |
| A3 | TI-MID19 | TI-R-MID19-TAG5 | CTATGCGCCTTGCCAGCCCGCTCAGTGTACTACTCTACGGTAGCAGAGACTTGGTCT | (SEQ ID NO: 467) |
| B3 | TI-MID20 | TI-R-MID20-TAG5 | CTATGCGCCTTGCCAGCCCGCTCAGACGACTACAGTACGGTAGCAGAGACTTGGTCT | (SEQ ID NO: 468) |
| C3 | TI-MID21 | TI-R-MID21-TAG5 | CTATGCGCCTTGCCAGCCCGCTCAGCGTAGACTAGTACGGTAGCAGAGACTTGGTCT | (SEQ ID NO: 469) |
| D3 | TI-MID22 | TI-R-MID22-TAG5 | CTATGCGCCTTGCCAGCCCGCTCAGTACGAGTATGTACGGTAGCAGAGACTTGGTCT | (SEQ ID NO: 470) |
| E3 | TI-MID23 | TI-R-MID23-TAG5 | CTATGCGCCTTGCCAGCCCGCTCAGTACTCTCGTGTACGGTAGCAGAGACTTGGTCT | (SEQ ID NO: 471) |
| F3 | TI-MID24 | TI-R-MID24-TAG5 | CTATGCGCCTTGCCAGCCCGCTCAGTAGAGACGAGTACGGTAGCAGAGACTTGGTCT | (SEQ ID NO: 472) |
| G3 | TI-MID25 | TI-R-MID25-TAG5 | CTATGCGCCTTGCCAGCCCGCTCAGTCGTCGCTCGTACGGTAGCAGAGACTTGGTCT | (SEQ ID NO: 473) |
| H3 | TI-MID26 | TI-R-MID26-TAG5 | CTATGCGCCTTGCCAGCCCGCTCAGACATACGCGTTACGGTAGCAGAGACTTGGTCT | (SEQ ID NO: 474) |
| A4 | TI-MID27 | TI-R-MID27-TAG5 | CTATGCGCCTTGCCAGCCCGCTCAGACGCGAGTATTACGGTAGCAGAGACTTGGTCT | (SEQ ID NO: 475) |
| B4 | TI-MID28 | TI-R-MID28-TAG5 | CTATGCGCCTTGCCAGCCCGCTCAGACTACTATGTTACGGTAGCAGAGACTTGGTCT | (SEQ ID NO: 476) |
| C4 | TI-MID68 | TI-R-MID68-TAG5 | CTATGCGCCTTGCCAGCCCGCTCAGTCGCTGCGTATACGGTAGCAGAGACTTGGTCT | (SEQ ID NO: 477) |
| D4 | TI-MID30 | TI-R-MID30-TAG5 | CTATGCGCCTTGCCAGCCCGCTCAGAGACTATACTTACGGTAGCAGAGACTTGGTCT | (SEQ ID NO: 478) |
| E4 | TI-MID31 | TI-R-MID31-TAG5 | CTATGCGCCTTGCCAGCCCGCTCAGAGCGTCGTCTTACGGTAGCAGAGACTTGGTCT | (SEQ ID NO: 479) |
| F4 | TI-MID32 | TI-R-MID32-TAG5 | CTATGCGCCTTGCCAGCCCGCTCAGAGTACGCTATTACGGTAGCAGAGACTTGGTCT | (SEQ ID NO: 480) |
| G4 | TI-MID33 | TI-R-MID33-TAG5 | CTATGCGCCTTGCCAGCCCGCTCAGATAGAGTACTTACGGTAGCAGAGACTTGGTCT | (SEQ ID NO: 481) |

TABLE 16-continued

| Well | Barcode | Reverse Oligo Name | Reverse Oligo Sequence | SEQ ID NO. |
|---|---|---|---|---|
| H4 | TI-MID34 | TI-R-MID34-TAG5 | CTATGCGCCTTGCCAGCCCGCTCAGCACGCTACGTTACGGTAGCAGAGACTTGGTCT | (SEQ ID NO: 482) |
| A5 | TI-MID35 | TI-R-MID35-TAG5 | CTATGCGCCTTGCCAGCCCGCTCAGCAGTAGACGTTACGGTAGCAGAGACTTGGTCT | (SEQ ID NO: 483) |
| B5 | TI-MID36 | TI-R-MID36-TAG5 | CTATGCGCCTTGCCAGCCCGCTCAGCGACGTGACTTACGGTAGCAGAGACTTGGTCT | (SEQ ID NO: 484) |
| C5 | TI-MID37 | TI-R-MID37-TAG5 | CTATGCGCCTTGCCAGCCCGCTCAGTACACACACTTACGGTAGCAGAGACTTGGTCT | (SEQ ID NO: 485) |
| D5 | TI-MID38 | TI-R-MID38-TAG5 | CTATGCGCCTTGCCAGCCCGCTCAGTACACGTGATTACGGTAGCAGAGACTTGGTCT | (SEQ ID NO: 486) |
| E5 | TI-MID39 | TI-R-MID39-TAG5 | CTATGCGCCTTGCCAGCCCGCTCAGTACAGATCGTTACGGTAGCAGAGACTTGGTCT | (SEQ ID NO: 487) |
| F5 | TI-MID40 | TI-R-MID40-TAG5 | CTATGCGCCTTGCCAGCCCGCTCAGTACGCTGTCTTACGGTAGCAGAGACTTGGTCT | (SEQ ID NO: 488) |
| G5 | TI-MID69 | TI-R-MID69-TAG5 | CTATGCGCCTTGCCAGCCCGCTCAGTCTGACGTCATACGGTAGCAGAGACTTGGTCT | (SEQ ID NO: 489) |
| H5 | TI-MID42 | TI-R-MID42-TAG5 | CTATGCGCCTTGCCAGCCCGCTCAGTCGATCACGTTACGGTAGCAGAGACTTGGTCT | (SEQ ID NO: 490) |
| A6 | TI-MID43 | TI-R-MID43-TAG5 | CTATGCGCCTTGCCAGCCCGCTCAGTCGCACTAGTTACGGTAGCAGAGACTTGGTCT | (SEQ ID NO: 491) |
| B6 | TI-MID44 | TI-R-MID44-TAG5 | CTATGCGCCTTGCCAGCCCGCTCAGTCTAGCGACTTACGGTAGCAGAGACTTGGTCT | (SEQ ID NO: 492) |
| C6 | TI-MID45 | TI-R-MID45-TAG5 | CTATGCGCCTTGCCAGCCCGCTCAGTCTATACTATTACGGTAGCAGAGACTTGGTCT | (SEQ ID NO: 493) |
| D6 | TI-MID46 | TI-R-MID46-TAG5 | CTATGCGCCTTGCCAGCCCGCTCAGTGACGTATGTTACGGTAGCAGAGACTTGGTCT | (SEQ ID NO: 494) |
| E6 | TI-MID47 | TI-R-MID47-TAG5 | CTATGCGCCTTGCCAGCCCGCTCAGTGTGAGTAGTTACGGTAGCAGAGACTTGGTCT | (SEQ ID NO: 495) |
| F6 | TI-MID48 | TI-R-MID48-TAG5 | CTATGCGCCTTGCCAGCCCGCTCAGACAGTATATATACGGTAGCAGAGACTTGGTCT | (SEQ ID NO: 496) |
| G6 | TI-MID49 | TI-R-MID49-TAG5 | CTATGCGCCTTGCCAGCCCGCTCAGACGCGATCGATACGGTAGCAGAGACTTGGTCT | (SEQ ID NO: 497) |
| H6 | TI-MID50 | TI-R-MID50-TAG5 | CTATGCGCCTTGCCAGCCCGCTCAGACTAGCAGTATACGGTAGCAGAGACTTGGTCT | (SEQ ID NO: 498) |

Example 8

Muliplex Barcoding of Target Nucleic Acids

Figure 18:
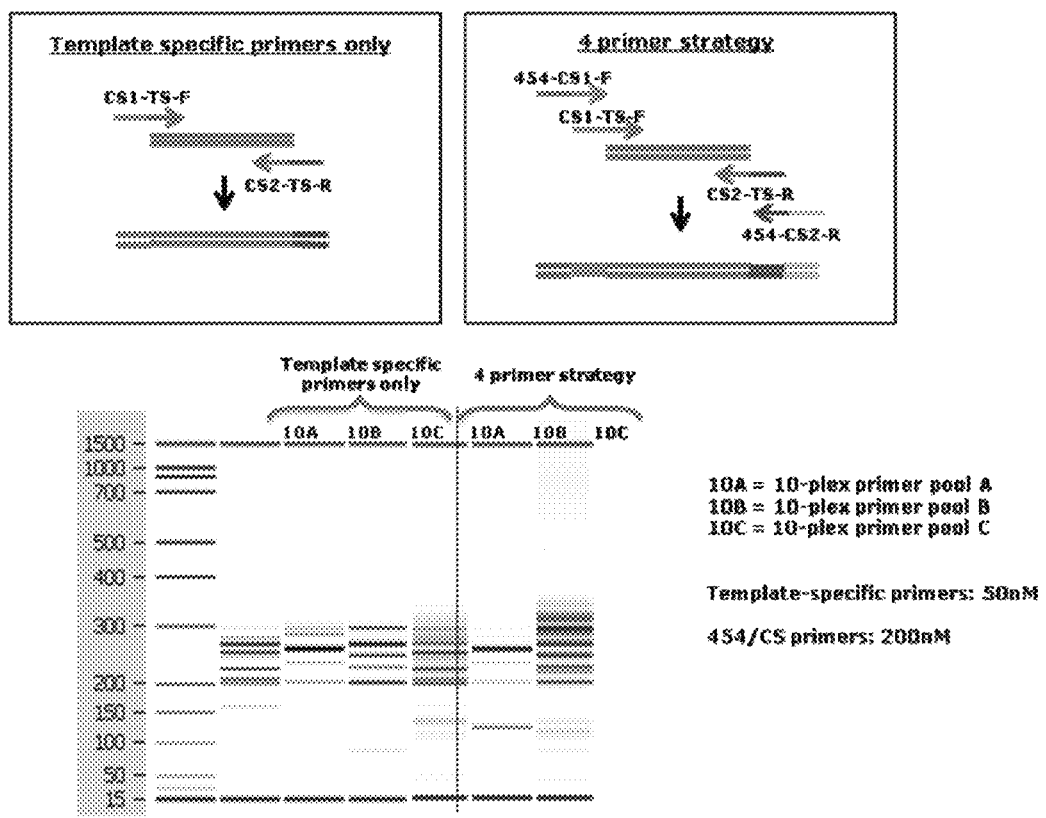
FIG. 18 shows results from Example 8: PCR reactions of three pools of 10 sets of PCR primers (A, B, C) when the PCR reactions were run for template-specific primers only and in 4-primer mode. The presence of higher molecular weight products in the 4-primer strategy demonstrates successful 4-primer assembly.
Figure 19:
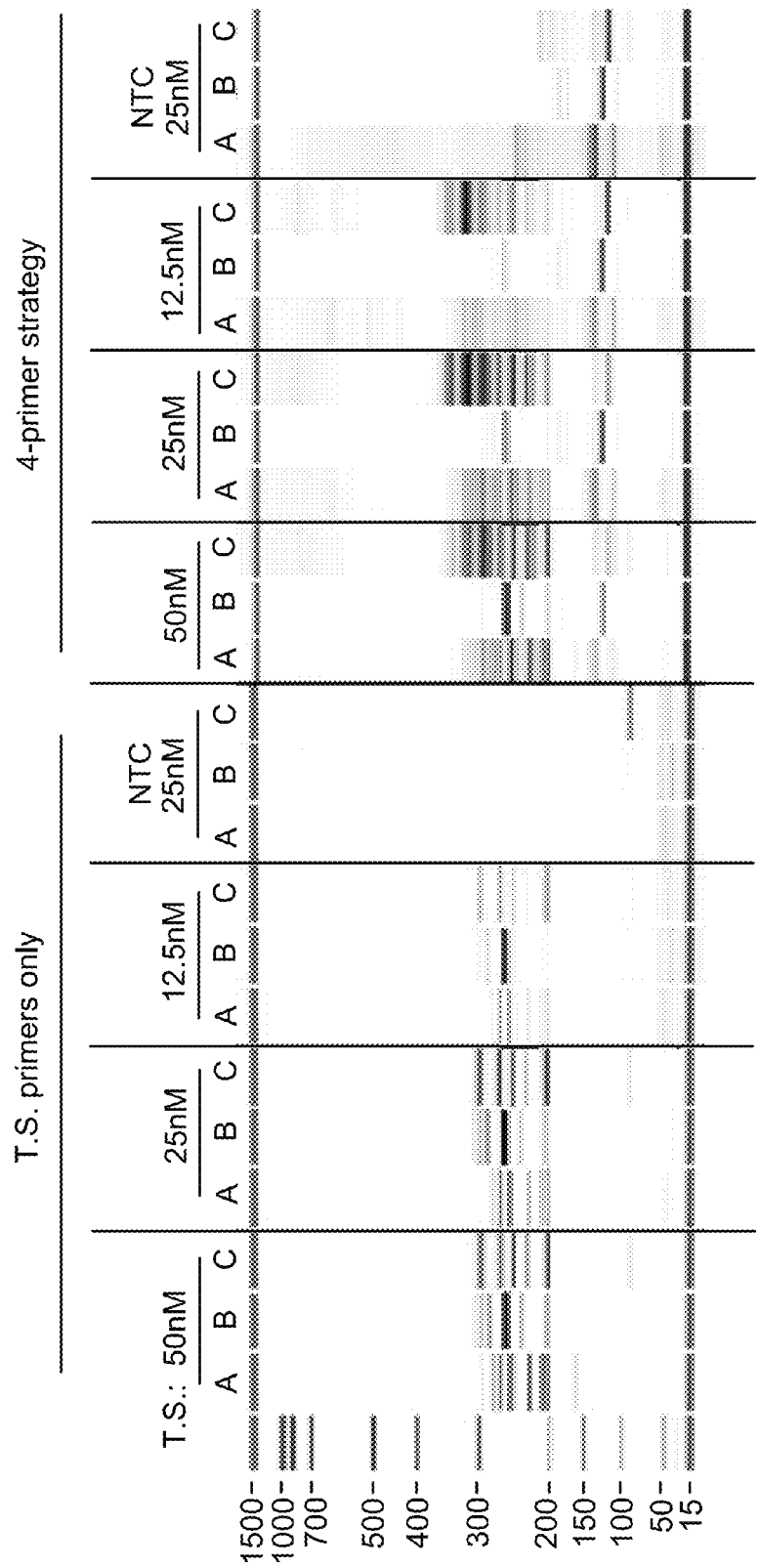
FIG. 19 shows results from Example 8: Changing the ratio of inner and outer primers impacts yield in multiplex 4-primer PCR using inner and outer primers.

Three pools of 10 primers were assembled from the primers listed in Table 9. PCR conditions were identical to those listed in Example 4, with the exception that primer concentrations were varied. FIG. 18 shows the results of PCR reactions of three pools of 10 sets of PCR primers (A, B, C) when the PCR reactions were run for template-specific primers only and in 4-primer mode. The presence of higher molecular weight products in the 4-primer strategy demonstrates successful 4-primer assembly.

What is claimed is:

1. A method for amplifying more than 100 target nucleic acids, the method comprising:
preparing more than 100 amplification mixtures using a microfluidic device, each amplification mixture having a fixed volume between 1 picoliter and 500 nanoliters;
wherein one amplification mixture is prepared for each target nucleic acid, each amplification mixture comprising:
  a forward primer comprising a target-specific sequence; and
  a reverse primer comprising a target-specific sequence;
subjecting each amplification mixture to amplification to produce a plurality of target nucleotide sequences;
using at least two additional primers to tag the target nucleotide sequences to produce a plurality of target amplicons, each comprising first and/or second nucleotide tags at the end(s) of the amplicon; and
performing automated sequencing on the plurality of target amplicons to yield sequencing data showing that at least 50 percent of the target amplicons are present at greater than 50 percent of the average number of copies of target amplicons and less than 2-fold the average number of copies of target amplicons.

2. The method of claim 1, wherein at least 70 percent of the target amplicons are present at greater than 50 percent of the average number of copies of target amplicons and less than 2-fold the average number of copies of target amplicons.

3. The method of claim 1, wherein the average length of the target amplicons is at least 25 bases.

4. The method of claim 1, wherein the average length of the target amplicons is at least 50 bases.

5. The method of claim 1, wherein the average length of the target amplicons is at least 100 bases.

6. The method of claim 1, wherein the average length of the target amplicons is at least 200 bases.

7. The method of claim 1, wherein the average length of the target amplicons is at least 1 kilobase.

8. The method of claim 1, wherein at least 90 percent of the target amplicons are present at greater than 50 percent of the average number of copies of target amplicons and less than 2-fold the average number of copies of target amplicons.

9. The method of claim 1, wherein the volume of the amplification mixtures is in the range of about 5 picoliters to about 25 nanoliters.

10. The method of claim 1, wherein the amplification mixtures are formed in separate compartments of a microfluidic device prior to amplification.

11. The method of claim 1, wherein the microfluidic device permits recovery of pools of reaction products, and the variability, with respect to volume and/or copy number, of each pool recovered from the device is less than 10 percent.

12. The method of claim 11, wherein the variability is less than 5%.

13. The method of claim 1, wherein each target amplicon is capable of being bound by DNA sequencing primers.

14. The method of claim 1, wherein the method is performed in determining the copy numbers of the target nucleic acids in each sample.

15. The method of claim 1, wherein the method is performed in determining the genotypes at loci corresponding to the target nucleic acids.

16. The method of claim 1, wherein the method is performed in determining the expression levels of the target nucleic acids.

* * * * *

SEQUENCE LISTING

<160> NUMBER OF SEQ ID NOS: 594

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatctcatc cctgcgtgtc                                                20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctatcccct gtgtgccttg                                                20

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcggcgacc atctcatccc tgcgtgtc                                       28

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcctccctcg cgccatcag                                                 19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccttgccag cccgctcag                                                 19

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggcggcgagc ctccctcgcg ccatcag                                        27

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acactctttc cctacacga                                                    19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caagcagaag acggcata                                                     18

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcggcgaac actctttccc tacacga                                           27

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccactacgcc tccgctttcc tctctatg                                          28

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgccccggg ttcctcattc t                                                 21

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcggcgacc actacgcctc cgctttcctc tctatg                                 36

```
<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccatctcatc cctgcgtg                                                     18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctatcccct gtgtgccttg                                                   20

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcggcgacc atctcatccc tgcgtg                                            26

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taatgatacg gcgaccacc                                                    19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acaagcagaa gacggcatac                                                   20

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcggcgata atgatacggc gaccac                                            26
```

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcctccctcg cgccatcagg catgcacact gacgacatgg ttctaca        47

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcctccctcg cgccatcagc gtacgacact gacgacatgg ttctaca        47

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcctccctcg cgccatcagg tcagcacact gacgacatgg ttctaca        47

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcctccctcg cgccatcaga gctgcacact gacgacatgg ttctaca        47

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcctccctcg cgccatcagt gcatcacact gacgacatgg ttctaca        47

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcctccctcg cgccatcagc tgatgacact gacgacatgg ttctaca        47

<210> SEQ ID NO 25

```
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcctccctcg cgccatcagg tagtcacact gacgacatgg ttctaca              47

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcctccctcg cgccatcagg tcgatacact gacgacatgg ttctaca              47

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcctccctcg cgccatcagg atacgacact gacgacatgg ttctaca              47

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcctccctcg cgccatcagt gatgcacact gacgacatgg ttctaca              47

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcctccctcg cgccatcaga gctgaacact gacgacatgg ttctaca              47

<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcctccctcg cgccatcaga ctgtaacact gacgacatgg ttctaca              47

<210> SEQ ID NO 31
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcctccctcg cgccatcagt gcatgacact gacgacatgg ttctaca                47

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcctccctcg cgccatcaga gtctaacact gacgacatgg ttctaca                47

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcctccctcg cgccatcagt gtctgacact gacgacatgg ttctaca                47

<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcctccctcg cgccatcagg ctagcacact gacgacatgg ttctaca                47

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcctccctcg cgccatcagg atagcacact gacgacatgg ttctaca                47

<210> SEQ ID NO 36
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcctccctcg cgccatcagg ctactacact gacgacatgg ttctaca                47

<210> SEQ ID NO 37
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
gcctccctcg cgccatcagc tatgcacact gacgacatgg ttctaca            47

<210> SEQ ID NO 38
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcctccctcg cgccatcagg ctatgacact gacgacatgg ttctaca            47

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcctccctcg cgccatcagc gtgcaacact gacgacatgg ttctaca            47

<210> SEQ ID NO 40
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcctccctcg cgccatcaga tagctacact gacgacatgg ttctaca            47

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcctccctcg cgccatcagt gtagcacact gacgacatgg ttctaca            47

<210> SEQ ID NO 42
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcctccctcg cgccatcagg tgctaacact gacgacatgg ttctaca            47

<210> SEQ ID NO 43
<211> LENGTH: 47
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
gcctccctcg cgccatcagg tcatgacact gacgacatgg ttctaca        47

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcctccctcg cgccatcaga tcgtgacact gacgacatgg ttctaca        47

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gcctccctcg cgccatcagt gtacgacact gacgacatgg ttctaca        47

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcctccctcg cgccatcaga gtgtaacact gacgacatgg ttctaca        47

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcctccctcg cgccatcagt gacagacact gacgacatgg ttctaca        47

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcctccctcg cgccatcagg atcacacact gacgacatgg ttctaca        47

<210> SEQ ID NO 49
<211> LENGTH: 47
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 49
gcctccctcg cgccatcagc tagagacact gacgacatgg ttctaca       47

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcctccctcg cgccatcagc tagtcacact gacgacatgg ttctaca       47

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcctccctcg cgccatcaga gctagacact gacgacatgg ttctaca       47

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gcctccctcg cgccatcagt gactgacact gacgacatgg ttctaca       47

<210> SEQ ID NO 53
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcctccctcg cgccatcagt gatagacact gacgacatgg ttctaca       47

<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcctccctcg cgccatcagc gtatcacact gacgacatgg ttctaca       47

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gcctccctcg cgccatcagg tctgaacact gacgacatgg ttctaca         47

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcctccctcg cgccatcagc atgacacact gacgacatgg ttctaca         47

<210> SEQ ID NO 57
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcctccctcg cgccatcagc gatgaacact gacgacatgg ttctaca         47

<210> SEQ ID NO 58
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcctccctcg cgccatcagg ctgatacact gacgacatgg ttctaca         47

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcctccctcg cgccatcagc agtacacact gacgacatgg ttctaca         47

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcctccctcg cgccatcagg cgactacact gacgacatgg ttctaca         47

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcctccctcg cgccatcagg tacgaacact gacgacatgg ttctaca        47

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcctccctcg cgccatcaga cgctaacact gacgacatgg ttctaca        47

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcctccctcg cgccatcaga gcatcacact gacgacatgg ttctaca        47

<210> SEQ ID NO 64
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcctccctcg cgccatcagg atgctacact gacgacatgg ttctaca        47

<210> SEQ ID NO 65
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcctccctcg cgccatcagg tctgcacact gacgacatgg ttctaca        47

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcctccctcg cgccatcaga tgcgaacact gacgacatgg ttctaca        47

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acactgacga catggttcta caactgtcca gctttgtgcc     40

<210> SEQ ID NO 68
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acactgacga catggttcta cagatcatca taggagttgc attgttg     47

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acactgacga catggttcta cacggacctt tgtccttcct     40

<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acactgacga catggttcta caatgcaaac ctcaatccct cc     42

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acactgacga catggttcta caagtttctt cccatgcacc tg     42

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acactgacga catggttcta cagtgaatcc ccgtctctac taaaa     45

<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acactgacga catggttcta catgtttccc atttgcggtt atga         44

<210> SEQ ID NO 74
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acactgacga catggttcta caagttgtgg gactgcttta tacatt       46

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gccttgccag cccgctcagt cctctgccta ggcgtt                  36

<210> SEQ ID NO 76
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gccttgccag cccgctcagg aaatgtaaat gtggagccaa aca          43

<210> SEQ ID NO 77
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gccttgccag cccgctcaga ctcattcttg aaaatacctc cgg          43

<210> SEQ ID NO 78
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gccttgccag cccgctcaga aatgccacct cgatttagga aa           42

<210> SEQ ID NO 79
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gccttgccag cccgctcagt caccctcccg aatagct                                    37

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gccttgccag cccgctcaga gtgtaaaatg gtacaaccgc t                              41

<210> SEQ ID NO 81
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gccttgccag cccgctcagc ctcttaagat actgtaaact ctgtaaagc                      49

<210> SEQ ID NO 82
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gccttgccag cccgctcaga ttgtgccatt gtactctagc c                              41

<210> SEQ ID NO 83
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
acactgacga catggttcta cacttccttt ctctactgaa tgcttttaat tt                  52

<210> SEQ ID NO 84
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acactgacga catggttcta catcttacac aaactcttca gaaaacaga                      49

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acactgacga catggttcta cagtaccaaa accaaacaag gacat                          45

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
acactgacga catggttcta caggtgaaac gccatctcta ctaa                     44

<210> SEQ ID NO 87
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acactgacga catggttcta catcatgatt gtagctgatt caacattca                49

<210> SEQ ID NO 88
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acactgacga catggttcta caactagcat gctgaaaccc c                        41

<210> SEQ ID NO 89
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acactgacga catggttcta catcaggaga tcgagaccat cc                       42

<210> SEQ ID NO 90
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acactgacga catggttcta catcatgcct gtaatcccag c                        41

<210> SEQ ID NO 91
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gccttgccag cccgctcaga cctcaaatga tccctgc                             38

<210> SEQ ID NO 92
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gccttgccag cccgctcaga ttacaggcgt gagccac                            37

<210> SEQ ID NO 93
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gccttgccag cccgctcagt tttgagatga agtcttgctc tgt                    43

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gccttgccag cccgctcagt aaagaccagt ctgactatgt tgc                    43

<210> SEQ ID NO 95
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gccttgccag cccgctcaga ccatgcccgg ctaatttt                          38

<210> SEQ ID NO 96
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gccttgccag cccgctcaga gttcacgcca ttctcctg                          38

<210> SEQ ID NO 97
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gccttgccag cccgctcagc actacgcccg gctaattttt                        39

```
<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gccttgccag cccgctcagt ggccccatta ggacatgtat                           40

<210> SEQ ID NO 99
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acactgacga catggttcta cattgtccca ttgcactcca g                         41

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acactgacga catggttcta catgggcaac aagagtgaaa ct                        42

<210> SEQ ID NO 101
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acactgacga catggttcta caaaataaat atagcagggt tgcaggt                   47

<210> SEQ ID NO 102
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acactgacga catggttcta catgcatttc tcttggctcc c                         41

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
acactgacga catggttcta caactttcct caactctaca tttccc                    46

<210> SEQ ID NO 104
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
acactgacga catggttcta catcagtgca aacaacagaa aagtg            45

<210> SEQ ID NO 105
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acactgacga catggttcta cacatgtttc ttagcaaatc tgatgaca         48

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
acactgacga catggttcta catctgtggt cccagctact              40

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gccttgccag cccgctcagt ttcaccatgt taggttggtc tc            42

<210> SEQ ID NO 108
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gccttgccag cccgctcagt gtaggttaaa tccaaatact ataccgtc        48

<210> SEQ ID NO 109
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gccttgccag cccgctcagt ctcaaatctt cagtagcaac taaaatct        48

<210> SEQ ID NO 110
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gccttgccag cccgctcagt cccgacctca ggtgatc                              37

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gccttgccag cccgctcagt ggtcttgaac tcccaacttc                           40

<210> SEQ ID NO 112
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gccttgccag cccgctcagc ctccgactcc caaagtg                              37

<210> SEQ ID NO 113
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gccttgccag cccgctcaga ctacagcctc ggactcc                              37

<210> SEQ ID NO 114
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gccttgccag cccgctcaga tcttgcacga agttatgcaa cta                       43

<210> SEQ ID NO 115
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acactgacga catggttcta caaccactgc actccagc                             38

<210> SEQ ID NO 116
<211> LENGTH: 50
<212> TYPE: DNA
```

<213> ORGANISM: Artificial Sequence
<220> FEATURE:
<223> OTHER INFORMATION: Description of Artificial Sequence: Synthetic
     primer

<400> SEQUENCE: 116
acactgacga catggttcta caacaaggaa aagtatcaga caatgtaagt         50

<210> SEQ ID NO 117
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 117
acactgacga catggttcta caacggtagc tcacacctgt aat               43

<210> SEQ ID NO 118
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 118
acactgacga catggttcta catggaagtc cctctctgat tgt               43

<210> SEQ ID NO 119
<211> LENGTH: 46
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 119
acactgacga catggttcta caactgactt tctgctcttg tctttc            46

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 120
acactgacga catggttcta caattctggg acagccaagt c                 41

<210> SEQ ID NO 121
<211> LENGTH: 41
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 121
acactgacga catggttcta caaggagttc aagaccagcc t                 41

<210> SEQ ID NO 122
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acactgacga catggttcta catctgtctc cttcctcttc ctac                    44

<210> SEQ ID NO 123
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gccttgccag cccgctcagc ctcttcccca aaagctct                           38

<210> SEQ ID NO 124
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gccttgccag cccgctcagt ctcgaactcc ttacttcagg t                       41

<210> SEQ ID NO 125
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gccttgccag cccgctcagc ccaacaccat gccagtg                            37

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gccttgccag cccgctcagt ccccagccct ccag                               34

<210> SEQ ID NO 127
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gccttgccag cccgctcaga ttgaagtctc atggaagcca g                       41

<210> SEQ ID NO 128
<211> LENGTH: 40
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 128
gccttgccag cccgctcagt caagtgatct tcccacctca                                40

<210> SEQ ID NO 129
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gccttgccag cccgctcaga caacctccgt catgtgc                                  37

<210> SEQ ID NO 130
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gccttgccag cccgctcaga cccatttact ttgcacatct ca                            42

<210> SEQ ID NO 131
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acactgacga catggttcta cattaagggt ggttgtcagt gg                            42

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acactgacga catggttcta cattgcagtg agctgagatc ac                            42

<210> SEQ ID NO 133
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acactgacga catggttcta caatctcctt actgctccca ct                            42

<210> SEQ ID NO 134
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
acactgacga catggttcta cattttatca cctttccttg cctctt                    46

<210> SEQ ID NO 135
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acactgacga catggttcta caactcgtcg taagttgaaa atattgtaag t              51

<210> SEQ ID NO 136
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
acactgacga catggttcta catcccaaag tgctgggatt ac                        42

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acactgacga catggttcta catccatcct cccagctcag                           40

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acactgacga catggttcta caatctcagc tcactgcagc                           40

<210> SEQ ID NO 139
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gccttgccag cccgctcaga gccaacctag gagataacac a                         41

<210> SEQ ID NO 140
<211> LENGTH: 38
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 140
gccttgccag cccgctcaga ggctccatct actcccaa                             38

<210> SEQ ID NO 141
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gccttgccag cccgctcagt tgataagagg tcccaagact tagta                     45

<210> SEQ ID NO 142
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gccttgccag cccgctcagt gggtgacaga gtgagact                             38

<210> SEQ ID NO 143
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gccttgccag cccgctcaga catcactgta atccagcctg                           40

<210> SEQ ID NO 144
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gccttgccag cccgctcaga gatcatgcca ctgcactc                             38

<210> SEQ ID NO 145
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gccttgccag cccgctcagg gcatgtgcct gtagtcc                              37

<210> SEQ ID NO 146
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 146
gccttgccag cccgctcagt ggtcttgaac tcctgacct                    39

<210> SEQ ID NO 147
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acactgacga catggttcta caaaacagca tggttgcatg aaag              44

<210> SEQ ID NO 148
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
acactgacga catggttcta caagtcgcat gcacatgtag tc                42

<210> SEQ ID NO 149
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
acactgacga catggttcta caaaaagtca gctgtatagg tacttgaag         49

<210> SEQ ID NO 150
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acactgacga catggttcta cacctcagtg tatccacaga aca               43

<210> SEQ ID NO 151
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
acactgacga catggttcta caatgcatgc ctgtaatccc ag                42

<210> SEQ ID NO 152
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
```
acactgacga catggttcta caaactcatg ttcaagacag aaggg    45

<210> SEQ ID NO 153
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
acactgacga catggttcta caattttctc taacttcaag gcccatat    48

<210> SEQ ID NO 154
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
acactgacga catggttcta catggatcca ccaagacttg ttttat    46

<210> SEQ ID NO 155
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
gccttgccag cccgctcagg attacaggtg tgagccact    39

<210> SEQ ID NO 156
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
gccttgccag cccgctcaga cagtacctga gttaaaagat ggttc    45

<210> SEQ ID NO 157
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
gccttgccag cccgctcagt gagaccctcc agctctg    37

<210> SEQ ID NO 158
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 158

```
gccttgccag cccgctcaga tcttccctta ccccatttta ctttatt          47
```

<210> SEQ ID NO 159
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159

```
gccttgccag cccgctcagt tcaaagaccc aaaacccaaa atg               43
```

<210> SEQ ID NO 160
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160

```
gccttgccag cccgctcagg tcaagttcta gaccccatgt aata              44
```

<210> SEQ ID NO 161
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161

```
gccttgccag cccgctcagt gtggtcccag ctactcc                      37
```

<210> SEQ ID NO 162
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162

```
gccttgccag cccgctcaga gcaaagtttt attgtaaaat aagagatcga t      51
```

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163

```
acactgacga catggttcta ca                                      22
```

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164

```
tacggtagca gagacttggt ct                                      22
```

<210> SEQ ID NO 165
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tacggtagca gagacttggt ctgcacacgc atattaaaat aggaa            45

<210> SEQ ID NO 166
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tacggtagca gagacttggt ctttcatctg cagacaggtc ca               42

<210> SEQ ID NO 167
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
tacggtagca gagacttggt ctccagcact ggcttgagac tt               42

<210> SEQ ID NO 168
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tacggtagca gagacttggt ctaggccaga ggagaatgag g                41

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tacggtagca gagacttggt ctatgaccct gccaaatgac ac               42

<210> SEQ ID NO 170
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tacggtagca gagacttggt cttggaaact gctctttgtg gtc              43

<210> SEQ ID NO 171
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tacggtagca gagacttggt cttggtggca ctaatgttcc cta            43

<210> SEQ ID NO 172
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tacggtagca gagacttggt ctgaggtccg tgtctacaac tgg            43

<210> SEQ ID NO 173
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tacggtagca gagacttggt ctccccctcac tcaccatctc c             41

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tacggtagca gagacttggt ctagtccgat gatgcctgct               40

<210> SEQ ID NO 175
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tacggtagca gagacttggt cttgagtgaa ggctacagac ccta           44

<210> SEQ ID NO 176
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tacggtagca gagacttggt ctagagggag gtggtcgatg t              41

<210> SEQ ID NO 177
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
tacggtagca gagacttggt cttctcccac tagtaccta accatc                46

<210> SEQ ID NO 178
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tacggtagca gagacttggt ctgcattcga ctcatctcag ca                    42

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tacggtagca gagacttggt ctcagcagct cgaatttctt cc                    42

<210> SEQ ID NO 180
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tacggtagca gagacttggt ctcctcttgg cagcaggata gt                    42

<210> SEQ ID NO 181
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tacggtagca gagacttggt ctaactccgg gatctggtca c                     41

<210> SEQ ID NO 182
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tacggtagca gagacttggt ctttctgtta gaaggaatcg ttttcc                46

<210> SEQ ID NO 183

```
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tacggtagca gagacttggt ctctcctgac agtccttgca ctt              43

<210> SEQ ID NO 184
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tacggtagca gagacttggt ctctttgtgt taggtagcct catatattc         49

<210> SEQ ID NO 185
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tacggtagca gagacttggt ctgccctgtg tcaagagtcc ag               42

<210> SEQ ID NO 186
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tacggtagca gagacttggt ctaccagaag ccatgctcaa ac               42

<210> SEQ ID NO 187
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tacggtagca gagacttggt cttgatctta tcctagcaac acagaag          47

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tacggtagca gagacttggt ctagaagtgc ccagtgaagc at               42

<210> SEQ ID NO 189
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tacggtagca gagacttggt ctcccaaagg aagtataagc caag                    44

<210> SEQ ID NO 190
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tacggtagca gagacttggt cttccaccta ctgctgtgtc tactg                   45

<210> SEQ ID NO 191
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tacggtagca gagacttggt cttctgatag gtccatctca tcttga                  46

<210> SEQ ID NO 192
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tacggtagca gagacttggt cttggtcatt caggcacttc ag                      42

<210> SEQ ID NO 193
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tacggtagca gagacttggt ctccttcttt cttcagaagc cact                    44

<210> SEQ ID NO 194
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
tacggtagca gagacttggt cttgggactt ccttctttgt atgg                    44

<210> SEQ ID NO 195
<211> LENGTH: 46
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 195
tacggtagca gagacttggt ctccagtgct attttgatgt ttatgc            46

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
tacggtagca gagacttggt ctttggcaag ctgcagtcac            40

<210> SEQ ID NO 197
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
tacggtagca gagacttggt ctgtactgac tgtcacggag ctg            43

<210> SEQ ID NO 198
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
tacggtagca gagacttggt cttccccgta ttaatgcatg gtat            44

<210> SEQ ID NO 199
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
tacggtagca gagacttggt ctttgttggc tatctggccc ta            42

<210> SEQ ID NO 200
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
tacggtagca gagacttggt ctgtctgttt ggagtctaat ttctgc            46

<210> SEQ ID NO 201
<211> LENGTH: 45
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 201
tacggtagca gagacttggt ctaatcaatt caccagcttt agcaa            45

<210> SEQ ID NO 202
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tacggtagca gagacttggt ctggctccct atacttgatt gtgg             44

<210> SEQ ID NO 203
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tacggtagca gagacttggt ctcgctggtc tacagagtta cttagga          47

<210> SEQ ID NO 204
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tacggtagca gagacttggt cttgaaggct cttaagaata gcaaatg          47

<210> SEQ ID NO 205
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tacggtagca gagacttggt ctttccctgt ggatattcaa ttttct           46

<210> SEQ ID NO 206
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tacggtagca gagacttggt ctatctctgc aaggcacagc tt               42

<210> SEQ ID NO 207
<211> LENGTH: 42
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 207
tacggtagca gagacttggt ctggaaagag cctcagcttg ac                          42

<210> SEQ ID NO 208
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tacggtagca gagacttggt ctcctctggg acacagacac ct                          42

<210> SEQ ID NO 209
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tacggtagca gagacttggt ctttcacagc atccgtgagc                             40

<210> SEQ ID NO 210
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tacggtagca gagacttggt ctccctcaga cccaggcatc                             40

<210> SEQ ID NO 211
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tacggtagca gagacttggt ctcccagccc agaattaagg t                           41

<210> SEQ ID NO 212
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tacggtagca gagacttggt ctgggcacat ggttcactgc                             40

<210> SEQ ID NO 213
<211> LENGTH: 47
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 213
gccttgccag cccgctcagg catgctacgg tagcagagac ttggtct              47

<210> SEQ ID NO 214
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gcctccctcg cgccatcagg catgcacact gacgacatgg ttctaca              47

<210> SEQ ID NO 215
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
gccttgccag cccgctcagc gtacgtacgg tagcagagac ttggtct              47

<210> SEQ ID NO 216
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
gcctccctcg cgccatcagc gtacgacact gacgacatgg ttctaca              47

<210> SEQ ID NO 217
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
gccttgccag cccgctcagg tcagctacgg tagcagagac ttggtct              47

<210> SEQ ID NO 218
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gcctccctcg cgccatcagg tcagcacact gacgacatgg ttctaca              47

<210> SEQ ID NO 219
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 219
gccttgccag cccgctcaga gctgctacgg tagcagagac ttggtct         47

<210> SEQ ID NO 220
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
gcctccctcg cgccatcaga gctgcacact gacgacatgg ttctaca         47

<210> SEQ ID NO 221
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gccttgccag cccgctcagt gcatctacgg tagcagagac ttggtct         47

<210> SEQ ID NO 222
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
gcctccctcg cgccatcagt gcatcacact gacgacatgg ttctaca         47

<210> SEQ ID NO 223
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gccttgccag cccgctcagc tgatgtacgg tagcagagac ttggtct         47

<210> SEQ ID NO 224
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
gcctccctcg cgccatcagc tgatgacact gacgacatgg ttctaca         47

<210> SEQ ID NO 225
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
gccttgccag cccgctcagg tagtctacgg tagcagagac ttggtct 47

<210> SEQ ID NO 226
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
gcctccctcg cgccatcagg tagtcacact gacgacatgg ttctaca 47

<210> SEQ ID NO 227
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gccttgccag cccgctcagg tcgattacgg tagcagagac ttggtct 47

<210> SEQ ID NO 228
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
gcctccctcg cgccatcagg tcgatacact gacgacatgg ttctaca 47

<210> SEQ ID NO 229
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gccttgccag cccgctcagg atacgtacgg tagcagagac ttggtct 47

<210> SEQ ID NO 230
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gcctccctcg cgccatcagg atacgacact gacgacatgg ttctaca 47

<210> SEQ ID NO 231
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gccttgccag cccgctcagt gatgctacgg tagcagagac ttggtct      47

<210> SEQ ID NO 232
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gcctccctcg cgccatcagt gatgcacact gacgacatgg ttctaca      47

<210> SEQ ID NO 233
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gccttgccag cccgctcaga gctgatacgg tagcagagac ttggtct      47

<210> SEQ ID NO 234
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
gcctccctcg cgccatcaga gctgaacact gacgacatgg ttctaca      47

<210> SEQ ID NO 235
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gccttgccag cccgctcaga ctgtatacgg tagcagagac ttggtct      47

<210> SEQ ID NO 236
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
gcctccctcg cgccatcaga ctgtaacact gacgacatgg ttctaca      47

<210> SEQ ID NO 237
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
gccttgccag cccgctcagt gcatgtacgg tagcagagac ttggtct        47

<210> SEQ ID NO 238
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gcctccctcg cgccatcagt gcatgacact gacgacatgg ttctaca        47

<210> SEQ ID NO 239
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gccttgccag cccgctcaga gtctatacgg tagcagagac ttggtct        47

<210> SEQ ID NO 240
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gcctccctcg cgccatcaga gtctaacact gacgacatgg ttctaca        47

<210> SEQ ID NO 241
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
gccttgccag cccgctcagt gtctgtacgg tagcagagac ttggtct        47

<210> SEQ ID NO 242
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
gcctccctcg cgccatcagt gtctgacact gacgacatgg ttctaca        47

<210> SEQ ID NO 243
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gccttgccag cccgctcagg ctagctacgg tagcagagac ttggtct        47

```
<210> SEQ ID NO 244
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
gcctccctcg cgccatcagg ctagcacact gacgacatgg ttctaca          47

<210> SEQ ID NO 245
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
gccttgccag cccgctcagg atagctacgg tagcagagac ttggtct          47

<210> SEQ ID NO 246
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctccctcg cgccatcagg atagcacact gacgacatgg ttctaca          47

<210> SEQ ID NO 247
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
gccttgccag cccgctcagg ctacttacgg tagcagagac ttggtct          47

<210> SEQ ID NO 248
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
gcctccctcg cgccatcagg ctactacact gacgacatgg ttctaca          47

<210> SEQ ID NO 249
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gccttgccag cccgctcagc tatgctacgg tagcagagac ttggtct          47
```

<210> SEQ ID NO 250
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
gcctccctcg cgccatcagc tatgcacact gacgacatgg ttctaca      47

<210> SEQ ID NO 251
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
gccttgccag cccgctcagg ctatgtacgg tagcagagac ttggtct      47

<210> SEQ ID NO 252
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
gcctccctcg cgccatcagg ctatgacact gacgacatgg ttctaca      47

<210> SEQ ID NO 253
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 253
gccttgccag cccgctcagc gtgcatacgg tagcagagac ttggtct      47

<210> SEQ ID NO 254
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 254
gcctccctcg cgccatcagc gtgcaacact gacgacatgg ttctaca      47

<210> SEQ ID NO 255
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 255
gccttgccag cccgctcaga tagcttacgg tagcagagac ttggtct      47

<210> SEQ ID NO 256
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 256
gcctccctcg cgccatcaga tagctacact gacgacatgg ttctaca           47

<210> SEQ ID NO 257
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 257
gccttgccag cccgctcagt gtagctacgg tagcagagac ttggtct           47

<210> SEQ ID NO 258
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 258
gcctccctcg cgccatcagt gtagcacact gacgacatgg ttctaca           47

<210> SEQ ID NO 259
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 259
gccttgccag cccgctcagg tgctatacgg tagcagagac ttggtct           47

<210> SEQ ID NO 260
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 260
gcctccctcg cgccatcagg tgctaacact gacgacatgg ttctaca           47

<210> SEQ ID NO 261
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 261
gccttgccag cccgctcagg tcatgtacgg tagcagagac ttggtct           47

<210> SEQ ID NO 262

<210> SEQ ID NO 262
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 262
gcctccctcg cgccatcagg tcatgacact gacgacatgg ttctaca        47

<210> SEQ ID NO 263
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
gccttgccag cccgctcaga tcgtgtacgg tagcagagac ttggtct        47

<210> SEQ ID NO 264
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
gcctccctcg cgccatcaga tcgtgacact gacgacatgg ttctaca        47

<210> SEQ ID NO 265
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
gccttgccag cccgctcagt gtacgtacgg tagcagagac ttggtct        47

<210> SEQ ID NO 266
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
gcctccctcg cgccatcagt gtacgacact gacgacatgg ttctaca        47

<210> SEQ ID NO 267
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 267
gccttgccag cccgctcaga gtgtatacgg tagcagagac ttggtct        47

<210> SEQ ID NO 268
<211> LENGTH: 47

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gcctccctcg cgccatcaga gtgtaacact gacgacatgg ttctaca                47

<210> SEQ ID NO 269
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
gccttgccag cccgctcagt gacagtacgg tagcagagac ttggtct                47

<210> SEQ ID NO 270
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gcctccctcg cgccatcagt gacagacact gacgacatgg ttctaca                47

<210> SEQ ID NO 271
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gccttgccag cccgctcagg atcactacgg tagcagagac ttggtct                47

<210> SEQ ID NO 272
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
gcctccctcg cgccatcagg atcacacact gacgacatgg ttctaca                47

<210> SEQ ID NO 273
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
gccttgccag cccgctcagc tagagtacgg tagcagagac ttggtct                47

<210> SEQ ID NO 274
<211> LENGTH: 47
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 274
gcctccctcg cgccatcagc tagagacact gacgacatgg ttctaca          47

<210> SEQ ID NO 275
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
gccttgccag cccgctcagc tagtctacgg tagcagagac ttggtct          47

<210> SEQ ID NO 276
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
gcctccctcg cgccatcagc tagtcacact gacgacatgg ttctaca          47

<210> SEQ ID NO 277
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
gccttgccag cccgctcaga gctagtacgg tagcagagac ttggtct          47

<210> SEQ ID NO 278
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gcctccctcg cgccatcaga gctagacact gacgacatgg ttctaca          47

<210> SEQ ID NO 279
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
gccttgccag cccgctcagt gactgtacgg tagcagagac ttggtct          47

<210> SEQ ID NO 280
<211> LENGTH: 47
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 280
gcctccctcg cgccatcagt gactgacact gacgacatgg ttctaca           47

<210> SEQ ID NO 281
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gccttgccag cccgctcagt gatagtacgg tagcagagac ttggtct           47

<210> SEQ ID NO 282
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
gcctccctcg cgccatcagt gatagacact gacgacatgg ttctaca           47

<210> SEQ ID NO 283
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gccttgccag cccgctcagc gtatctacgg tagcagagac ttggtct           47

<210> SEQ ID NO 284
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
gcctccctcg cgccatcagc gtatcacact gacgacatgg ttctaca           47

<210> SEQ ID NO 285
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gccttgccag cccgctcagg tctgatacgg tagcagagac ttggtct           47

<210> SEQ ID NO 286
<211> LENGTH: 47
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 286
gcctccctcg cgccatcagg tctgaacact gacgacatgg ttctaca                47

<210> SEQ ID NO 287
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
gccttgccag cccgctcagc atgactacgg tagcagagac ttggtct                47

<210> SEQ ID NO 288
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
gcctccctcg cgccatcagc atgacacact gacgacatgg ttctaca                47

<210> SEQ ID NO 289
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
gccttgccag cccgctcagc gatgatacgg tagcagagac ttggtct                47

<210> SEQ ID NO 290
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
gcctccctcg cgccatcagc gatgaacact gacgacatgg ttctaca                47

<210> SEQ ID NO 291
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
gccttgccag cccgctcagg ctgattacgg tagcagagac ttggtct                47

<210> SEQ ID NO 292
<211> LENGTH: 47
<212> TYPE: DNA
<213> ORGANISM: Artificial Sequence
<220> FEATURE:
<223> OTHER INFORMATION: Description of Artificial Sequence: Synthetic

```
                      primer

<400> SEQUENCE: 292
gcctccctcg cgccatcagg ctgatacact gacgacatgg ttctaca          47

<210> SEQ ID NO 293
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
gccttgccag cccgctcagc agtactacgg tagcagagac ttggtct          47

<210> SEQ ID NO 294
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
gcctccctcg cgccatcagc agtacacact gacgacatgg ttctaca          47

<210> SEQ ID NO 295
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
gccttgccag cccgctcagg cgacttacgg tagcagagac ttggtct          47

<210> SEQ ID NO 296
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
gcctccctcg cgccatcagg cgactacact gacgacatgg ttctaca          47

<210> SEQ ID NO 297
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
gccttgccag cccgctcagg tacgatacgg tagcagagac ttggtct          47

<210> SEQ ID NO 298
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 298
gcctccctcg cgccatcagg tacgaacact gacgacatgg ttctaca    47

<210> SEQ ID NO 299
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
gccttgccag cccgctcaga cgctatacgg tagcagagac ttggtct    47

<210> SEQ ID NO 300
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
gcctccctcg cgccatcaga cgctaacact gacgacatgg ttctaca    47

<210> SEQ ID NO 301
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gccttgccag cccgctcaga gcatctacgg tagcagagac ttggtct    47

<210> SEQ ID NO 302
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
gcctccctcg cgccatcaga gcatcacact gacgacatgg ttctaca    47

<210> SEQ ID NO 303
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gccttgccag cccgctcagg atgcttacgg tagcagagac ttggtct    47

<210> SEQ ID NO 304
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
gcctccctcg cgccatcagg atgctacact gacgacatgg ttctaca        47

<210> SEQ ID NO 305
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gccttgccag cccgctcagg tctgctacgg tagcagagac ttggtct        47

<210> SEQ ID NO 306
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
gcctccctcg cgccatcagg tctgcacact gacgacatgg ttctaca        47

<210> SEQ ID NO 307
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
gccttgccag cccgctcaga tgcgatacgg tagcagagac ttggtct        47

<210> SEQ ID NO 308
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
gcctccctcg cgccatcaga tgcgaacact gacgacatgg ttctaca        47

<210> SEQ ID NO 309
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
acactgacga catggttcta cattcttaga ccatccagga ggtg        44

<210> SEQ ID NO 310
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tacggtagca gagacttggt ctccagcctc tcaccctgta aa         42

<210> SEQ ID NO 311
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
acactgacga catggttcta caagctggaa agagtgctca cc         42

<210> SEQ ID NO 312
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
tacggtagca gagacttggt cttaggagct ggaggcagag at         42

<210> SEQ ID NO 313
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
acactgacga catggttcta cagcgtcatc agtttctcat catt       44

<210> SEQ ID NO 314
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
tacggtagca gagacttggt ctacatgggt ctgaggctgt tc         42

<210> SEQ ID NO 315
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
acactgacga catggttcta caccctggga aatgatccta cc         42

<210> SEQ ID NO 316
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
tacggtagca gagacttggt cttcttacca ggcagtcgct ct            42

<210> SEQ ID NO 317
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
acactgacga catggttcta caccagcgtg tcctctctcc t             41

<210> SEQ ID NO 318
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
tacggtagca gagacttggt ctgacaagga tgcctgacca gt            42

<210> SEQ ID NO 319
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
acactgacga catggttcta cacaaaggag gatggagcct ttc           43

<210> SEQ ID NO 320
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
tacggtagca gagacttggt ctgatgtgtt cctttggagg tgg           43

<210> SEQ ID NO 321
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
acactgacga catggttcta catccaacaa atgtgaacgg aat           43

<210> SEQ ID NO 322
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
tacggtagca gagacttggt ctcaagcaac tgaacctgtg actc          44

<210> SEQ ID NO 323
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
acactgacga catggttcta cagatcaata atcaccctgt tgtttg                    46

<210> SEQ ID NO 324
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
tacggtagca gagacttggt ctttccaagg gaacaggaaa tatg                      44

<210> SEQ ID NO 325
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
acactgacga catggttcta catcctacgt ggtgtgtgtc tga                       43

<210> SEQ ID NO 326
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tacggtagca gagacttggt ctgctttggc tgtggtcaac tt                        42

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
acactgacga catggttcta caccacatga tttttcttct ctcca                     45

<210> SEQ ID NO 328
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
tacggtagca gagacttggt ctcggtgact tactgcagct gtt                       43

<210> SEQ ID NO 329
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
acactgacga catggttcta cagctctgtc actgactgct gtg                43

<210> SEQ ID NO 330
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 330
tacggtagca gagacttggt ctgctataac aacaacctgg agcct             45

<210> SEQ ID NO 331
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 331
acactgacga catggttcta cagctgacgg gtttcctctt c                 41

<210> SEQ ID NO 332
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 332
tacggtagca gagacttggt ctgacgtgga tagcagcaag g                 41

<210> SEQ ID NO 333
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 333
acactgacga catggttcta cagcatgaac atttttctcc acct              44

<210> SEQ ID NO 334
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 334
tacggtagca gagacttggt ctttctgttc tccttcactt tccac             45

```
<210> SEQ ID NO 335
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
acactgacga catggttcta catttctctt tcacttccta cagatgc          47

<210> SEQ ID NO 336
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
tacggtagca gagacttggt ctccacagca gtgtggtcat tc               42

<210> SEQ ID NO 337
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
acactgacga catggttcta catggaatct gtcagcaacc tc               42

<210> SEQ ID NO 338
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tacggtagca gagacttggt ctcccaggac tggcactca                   39

<210> SEQ ID NO 339
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
acactgacga catggttcta cagctgaggt gacccttgtc tc               42

<210> SEQ ID NO 340
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
tacggtagca gagacttggt ctcccaccag accatgagag g                41

<210> SEQ ID NO 341
```

-continued

```
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
acactgacga catggttcta catcacaatt gccagttaac gtct                     44

<210> SEQ ID NO 342
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
tacggtagca gagacttggt ctccacacag caaagcagaa ac                       42

<210> SEQ ID NO 343
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
acactgacga catggttcta caccacactg acgtgcctct c                        41

<210> SEQ ID NO 344
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tacggtagca gagacttggt ctccgtatct cccttccctg at                       42

<210> SEQ ID NO 345
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
acactgacga catggttcta cacctcacag cagggtcttc tc                       42

<210> SEQ ID NO 346
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
tacggtagca gagacttggt ctctgaccta aagccacctc ctt                      43

<210> SEQ ID NO 347
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
acactgacga catggttcta cacactgcct catctctcac ca                           42

<210> SEQ ID NO 348
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
tacggtagca gagacttggt ctccagcttg gcctcagtac a                            41

<210> SEQ ID NO 349
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
acactgacga catggttcta cacatgatcc cactgccttc tt                           42

<210> SEQ ID NO 350
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
tacggtagca gagacttggt ctagtgtgga cagacccacc a                            41

<210> SEQ ID NO 351
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
acactgacga catggttcta cattccagtg ttctaattgc actgtt                       46

<210> SEQ ID NO 352
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
tacggtagca gagacttggt ctgagggact cttcccaatg ga                           42

<210> SEQ ID NO 353
<211> LENGTH: 46
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 353
acactgacga catggttcta cactaatagc ctcaaaatct ctgcac                    46

<210> SEQ ID NO 354
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
tacggtagca gagacttggt cttttgttca aatgagtaga cacagc                    46

<210> SEQ ID NO 355
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
acactgacga catggttcta cacattccat gggcaacttc tc                        42

<210> SEQ ID NO 356
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
tacggtagca gagacttggt ctttctggct tataaggtgt tcataca                   47

<210> SEQ ID NO 357
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
acactgacga catggttcta caccttccct catttcctcc tg                        42

<210> SEQ ID NO 358
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
tacggtagca gagacttggt cttccagaca agccactcac c                         41

<210> SEQ ID NO 359
<211> LENGTH: 45
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 359
acactgacga catggttcta cacctctgat ttctttccac tttca                       45

<210> SEQ ID NO 360
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
tacggtagca gagacttggt ctctaatttg gtggctgcct tt                          42

<210> SEQ ID NO 361
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
acactgacga catggttcta catgtcaaca gcacattcga cag                         43

<210> SEQ ID NO 362
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
tacggtagca gagacttggt ctggtcctgg gtatcgaaag agt                         43

<210> SEQ ID NO 363
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
acactgacga catggttcta catttcttcc agtttgccaa gg                          42

<210> SEQ ID NO 364
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
tacggtagca gagacttggt ctaggaaaat caaagtcacc aacc                        44

<210> SEQ ID NO 365
<211> LENGTH: 42
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 365
acactgacga catggttcta cactctcgcc ttgaacctgt tt                    42

<210> SEQ ID NO 366
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
tacggtagca gagacttggt ctcagcacag gcccagtctt                       40

<210> SEQ ID NO 367
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
acactgacga catggttcta cattccttgg tgccactaac taca                  44

<210> SEQ ID NO 368
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
tacggtagca gagacttggt ctgggagaat atgcagtgaa cctc                  44

<210> SEQ ID NO 369
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
acactgacga catggttcta catggattca cattaactct atgacca               47

<210> SEQ ID NO 370
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
tacggtagca gagacttggt ctttgcacaa taccagatag aacagac               47

<210> SEQ ID NO 371
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 371
acactgacga catggttcta catgagcttg ttggaataag gatg                    44

<210> SEQ ID NO 372
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
tacggtagca gagacttggt ctcgtctatg gaaattccct gtg                     43

<210> SEQ ID NO 373
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
acactgacga catggttcta cagaagctct ttccaccct tc                       42

<210> SEQ ID NO 374
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
tacggtagca gagacttggt cttgccagct gttagagatt cct                     43

<210> SEQ ID NO 375
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
acactgacga catggttcta catgtccttg taggttttcc caaa                    44

<210> SEQ ID NO 376
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
tacggtagca gagacttggt ctccccagca aagcatttta ag                      42

<210> SEQ ID NO 377
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
acactgacga catggttcta cagaaaattc cttggatttg tcatg                    45

<210> SEQ ID NO 378
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
tacggtagca gagacttggt ctcatgatag gatagaatct tccttacca                49

<210> SEQ ID NO 379
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
acactgacga catggttcta cagttttgtt tttatctccc ctcca                    45

<210> SEQ ID NO 380
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
tacggtagca gagacttggt ctttcaaatt gacagatgca acaa                     44

<210> SEQ ID NO 381
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
acactgacga catggttcta caggaaccat tgagttatat ccttttg                  47

<210> SEQ ID NO 382
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
tacggtagca gagacttggt ctttgttttc ttatacccat cagaagc                  47

<210> SEQ ID NO 383
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
acactgacga catggttcta cattggtgga aagaacctct caa         43

<210> SEQ ID NO 384
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
tacggtagca gagacttggt ctcaggtacc atgaaagcca ca          42

<210> SEQ ID NO 385
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
acactgacga catggttcta catgttgcca agctgtattc tgtt        44

<210> SEQ ID NO 386
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
tacggtagca gagacttggt cttttgagct gatgatttaa gacagtg     47

<210> SEQ ID NO 387
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
acactgacga catggttcta caggacccaa agtgctacaa cc          42

<210> SEQ ID NO 388
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
tacggtagca gagacttggt ctcaagaatc gacgacaatc ttaaac      46

<210> SEQ ID NO 389
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
acactgacga catggttcta cagcccatga tagccgtctt ta      42

<210> SEQ ID NO 390
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
tacggtagca gagacttggt ctcaacaatg tcacaaccca ctg      43

<210> SEQ ID NO 391
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
acactgacga catggttcta caccttcatc ttacagatca gtttcct      47

<210> SEQ ID NO 392
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tacggtagca gagacttggt ctgcttactg gaaaatcgta tttaacaaa      49

<210> SEQ ID NO 393
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
acactgacga catggttcta caacgcagtg ctaaccaagt tct      43

<210> SEQ ID NO 394
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
tacggtagca gagacttggt cttccacaag gggaaagtgt aaa      43

<210> SEQ ID NO 395
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
acactgacga catggttcta catgtctcca ccactggatt tct       43

<210> SEQ ID NO 396
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
tacggtagca gagacttggt ctggcttaca gctagtttgc cagt       44

<210> SEQ ID NO 397
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
acactgacga catggttcta catgcttttc taactctctt tgactgc    47

<210> SEQ ID NO 398
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
tacggtagca gagacttggt cttcctcctt gtcacttaat ttgga      45

<210> SEQ ID NO 399
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
acactgacga catggttcta cattctattt cagccacggg taa        43

<210> SEQ ID NO 400
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
tacggtagca gagacttggt ctagaggaga aactcagaga taaccaa    47

<210> SEQ ID NO 401
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
acactgacga catggttcta cactcacctc atctgtcctg tttct      45

<210> SEQ ID NO 402
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
tacggtagca gagacttggt ctggcatttc tgtaaaagta aagaacg         47

<210> SEQ ID NO 403
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
acactgacga catggttcta cacctgcctt caaagggtct ct              42

<210> SEQ ID NO 404
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
tacggtagca gagacttggt ctgtgtggac tgttgctttg aca             43

<210> SEQ ID NO 405
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
gccttgccag cccgctcagg catgctacgg tagcagagac ttggtct         47

<210> SEQ ID NO 406
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
gcctccctcg cgccatcagg catgcacact gacgacatgg ttctaca         47

<210> SEQ ID NO 407
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
gccttgccag cccgctcagc gtacgtacgg tagcagagac ttggtct         47

<210> SEQ ID NO 408
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 408
gcctccctcg cgccatcagc gtacgacact gacgacatgg ttctaca                47

<210> SEQ ID NO 409
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 409
gccttgccag cccgctcagg tcagctacgg tagcagagac ttggtct                47

<210> SEQ ID NO 410
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 410
gcctccctcg cgccatcagg tcagcacact gacgacatgg ttctaca                47

<210> SEQ ID NO 411
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 411
gccttgccag cccgctcaga gctgctacgg tagcagagac ttggtct                47

<210> SEQ ID NO 412
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 412
gcctccctcg cgccatcaga gctgcacact gacgacatgg ttctaca                47

<210> SEQ ID NO 413
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 413
gccttgccag cccgctcagt gcatctacgg tagcagagac ttggtct                47

<210> SEQ ID NO 414
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 414
gcctccctcg cgccatcagt gcatcacact gacgacatgg ttctaca      47

<210> SEQ ID NO 415
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 415
gccttgccag cccgctcagc tgatgtacgg tagcagagac ttggtct      47

<210> SEQ ID NO 416
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 416
gcctccctcg cgccatcagc tgatgacact gacgacatgg ttctaca      47

<210> SEQ ID NO 417
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 417
gccttgccag cccgctcagg tagtctacgg tagcagagac ttggtct      47

<210> SEQ ID NO 418
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 418
gcctccctcg cgccatcagg tagtcacact gacgacatgg ttctaca      47

<210> SEQ ID NO 419
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 419
gccttgccag cccgctcagg tcgattacgg tagcagagac ttggtct      47

<210> SEQ ID NO 420

```
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
gcctccctcg cgccatcagg tcgatacact gacgacatgg ttctaca           47

<210> SEQ ID NO 421
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
gccttgccag cccgctcagg atacgtacgg tagcagagac ttggtct           47

<210> SEQ ID NO 422
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
gcctccctcg cgccatcagg atacgacact gacgacatgg ttctaca           47

<210> SEQ ID NO 423
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
gccttgccag cccgctcagt gatgctacgg tagcagagac ttggtct           47

<210> SEQ ID NO 424
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
gcctccctcg cgccatcagt gatgcacact gacgacatgg ttctaca           47

<210> SEQ ID NO 425
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
gccttgccag cccgctcaga gctgatacgg tagcagagac ttggtct           47

<210> SEQ ID NO 426
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
gcctccctcg cgccatcaga gctgaacact gacgacatgg ttctaca        47

<210> SEQ ID NO 427
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
gccttgccag cccgctcaga ctgtatacgg tagcagagac ttggtct        47

<210> SEQ ID NO 428
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
gcctccctcg cgccatcaga ctgtaacact gacgacatgg ttctaca        47

<210> SEQ ID NO 429
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
gccttgccag cccgctcagt gcatgtacgg tagcagagac ttggtct        47

<210> SEQ ID NO 430
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
gcctccctcg cgccatcagt gcatgacact gacgacatgg ttctaca        47

<210> SEQ ID NO 431
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
gccttgccag cccgctcaga gtctatacgg tagcagagac ttggtct        47

<210> SEQ ID NO 432
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 432
gcctccctcg cgccatcaga gtctaacact gacgacatgg ttctaca                47

<210> SEQ ID NO 433
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
gccttgccag cccgctcagt gtctgtacgg tagcagagac ttggtct                47

<210> SEQ ID NO 434
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
gcctccctcg cgccatcagt gtctgacact gacgacatgg ttctaca                47

<210> SEQ ID NO 435
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
gccttgccag cccgctcagg ctagctacgg tagcagagac ttggtct                47

<210> SEQ ID NO 436
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
gcctccctcg cgccatcagg ctagcacact gacgacatgg ttctaca                47

<210> SEQ ID NO 437
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
acactctttc cctacacgac gctcttccga tct                               33

<210> SEQ ID NO 438
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 438
actgtccagc tttgtgcc                                                  18

<210> SEQ ID NO 439
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
acactctttc cctacacgac gctcttccga tctactgtcc agctttgtgc c             51

<210> SEQ ID NO 440
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
acactctttc cctacacgac gctcttccga tct                                 33

<210> SEQ ID NO 441
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
gatcatcata ggagttgcat tgttg                                          25

<210> SEQ ID NO 442
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
acactctttc cctacacgac gctcttccga tctgatcatc ataggagttg cattgttg      58

<210> SEQ ID NO 443
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
ctcggcattc ctgctgaacc gctcttccga tct                                 33

<210> SEQ ID NO 444
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 444
tcctctgcct aggcgtt                                                      17

<210> SEQ ID NO 445
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
ctcggcattc ctgctgaacc gctcttccga tcttcctctg cctaggcgtt                  50

<210> SEQ ID NO 446
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
ctcggcattc ctgctgaacc gctcttccga tct                                    33

<210> SEQ ID NO 447
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
gaaatgtaaa tgtggagcca aaca                                              24

<210> SEQ ID NO 448
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
ctcggcattc ctgctgaacc gctcttccga tctgaaatgt aaatgtggag ccaaaca          57

<210> SEQ ID NO 449
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
aatgatacgg cgaccaccga gatctacact ctttccctac acga                        44

<210> SEQ ID NO 450
<211> LENGTH: 47
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 450
caagcagaag acggcatacg agatcggtct cggcattcct gctgaac        47

<210> SEQ ID NO 451
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
cgtatcgcct ccctcgcgcc atcagacgag tgcgtacact gacgacatgg ttctaca    57

<210> SEQ ID NO 452
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
cgtatcgcct ccctcgcgcc atcagacgct cgacaacact gacgacatgg ttctaca    57

<210> SEQ ID NO 453
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
cgtatcgcct ccctcgcgcc atcagagacg cactcacact gacgacatgg ttctaca    57

<210> SEQ ID NO 454
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
cgtatcgcct ccctcgcgcc atcagtcgat agtgaacact gacgacatgg ttctaca    57

<210> SEQ ID NO 455
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
cgtatcgcct ccctcgcgcc atcagatcag acacgacact gacgacatgg ttctaca    57

<210> SEQ ID NO 456
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
cgtatcgcct ccctcgcgcc atcagatatc gcgagacact gacgacatgg ttctaca    57

<210> SEQ ID NO 457
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
cgtatcgcct ccctcgcgcc atcagcgtgt ctctaacact gacgacatgg ttctaca    57

<210> SEQ ID NO 458
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
cgtatcgcct ccctcgcgcc atcagctcgc gtgtcacact gacgacatgg ttctaca    57

<210> SEQ ID NO 459
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
cgtatcgcct ccctcgcgcc atcagtctct atgcgacact gacgacatgg ttctaca    57

<210> SEQ ID NO 460
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
cgtatcgcct ccctcgcgcc atcagtgata cgtctacact gacgacatgg ttctaca    57

<210> SEQ ID NO 461
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
cgtatcgcct ccctcgcgcc atcagcatag tagtgacact gacgacatgg ttctaca    57

<210> SEQ ID NO 462
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
cgtatcgcct ccctcgcgcc atcagcgaga gatacacact gacgacatgg ttctaca    57

<210> SEQ ID NO 463
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
cgtatcgcct ccctcgcgcc atcagatacg acgtaacact gacgacatgg ttctaca    57

<210> SEQ ID NO 464
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
cgtatcgcct ccctcgcgcc atcagtcacg tactaacact gacgacatgg ttctaca    57

<210> SEQ ID NO 465
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
cgtatcgcct ccctcgcgcc atcagcgtct agtacacact gacgacatgg ttctaca    57

<210> SEQ ID NO 466
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
cgtatcgcct ccctcgcgcc atcagtctac gtagcacact gacgacatgg ttctaca    57

<210> SEQ ID NO 467
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
cgtatcgcct ccctcgcgcc atcagtgtac tactcacact gacgacatgg ttctaca    57

<210> SEQ ID NO 468
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
cgtatcgcct ccctcgcgcc atcagacgac tacagacact gacgacatgg ttctaca       57

<210> SEQ ID NO 469
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
cgtatcgcct ccctcgcgcc atcagcgtag actagacact gacgacatgg ttctaca       57

<210> SEQ ID NO 470
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cgtatcgcct ccctcgcgcc atcagtacga gtatgacact gacgacatgg ttctaca       57

<210> SEQ ID NO 471
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
cgtatcgcct ccctcgcgcc atcagtactc tcgtgacact gacgacatgg ttctaca       57

<210> SEQ ID NO 472
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
cgtatcgcct ccctcgcgcc atcagtagag acgagacact gacgacatgg ttctaca       57

<210> SEQ ID NO 473
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
cgtatcgcct ccctcgcgcc atcagtcgtc gctcgacact gacgacatgg ttctaca       57

<210> SEQ ID NO 474
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
cgtatcgcct ccctcgcgcc atcagacata cgcgtacact gacgacatgg ttctaca    57

<210> SEQ ID NO 475
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
cgtatcgcct ccctcgcgcc atcagacgcg agtatacact gacgacatgg ttctaca    57

<210> SEQ ID NO 476
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
cgtatcgcct ccctcgcgcc atcagactac tatgtacact gacgacatgg ttctaca    57

<210> SEQ ID NO 477
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
cgtatcgcct ccctcgcgcc atcagtcgct gcgtaacact gacgacatgg ttctaca    57

<210> SEQ ID NO 478
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
cgtatcgcct ccctcgcgcc atcagagact atactacact gacgacatgg ttctaca    57

<210> SEQ ID NO 479
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
cgtatcgcct ccctcgcgcc atcagagcgt cgtctacact gacgacatgg ttctaca    57

<210> SEQ ID NO 480
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
cgtatcgcct ccctcgcgcc atcagagtac gctatacact gacgacatgg ttctaca    57

<210> SEQ ID NO 481
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
cgtatcgcct ccctcgcgcc atcagataga gtactacact gacgacatgg ttctaca        57

<210> SEQ ID NO 482
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
cgtatcgcct ccctcgcgcc atcagcacgc tacgtacact gacgacatgg ttctaca        57

<210> SEQ ID NO 483
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
cgtatcgcct ccctcgcgcc atcagcagta gacgtacact gacgacatgg ttctaca        57

<210> SEQ ID NO 484
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
cgtatcgcct ccctcgcgcc atcagcgacg tgactacact gacgacatgg ttctaca        57

<210> SEQ ID NO 485
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
cgtatcgcct ccctcgcgcc atcagtacac acactacact gacgacatgg ttctaca        57

<210> SEQ ID NO 486
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
cgtatcgcct ccctcgcgcc atcagtacac gtgatacact gacgacatgg ttctaca        57

<210> SEQ ID NO 487
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 487
cgtatcgcct ccctcgcgcc atcagtacag atcgtacact gacgacatgg ttctaca      57

<210> SEQ ID NO 488
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 488
cgtatcgcct ccctcgcgcc atcagtacgc tgtctacact gacgacatgg ttctaca      57

<210> SEQ ID NO 489
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 489
cgtatcgcct ccctcgcgcc atcagtctga cgtcaacact gacgacatgg ttctaca      57

<210> SEQ ID NO 490
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 490
cgtatcgcct ccctcgcgcc atcagtcgat cacgtacact gacgacatgg ttctaca      57

<210> SEQ ID NO 491
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 491
cgtatcgcct ccctcgcgcc atcagtcgca ctagtacact gacgacatgg ttctaca      57

<210> SEQ ID NO 492
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 492
cgtatcgcct ccctcgcgcc atcagtctag cgactacact gacgacatgg ttctaca      57

```
<210> SEQ ID NO 493
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
cgtatcgcct ccctcgcgcc atcagtctat actatacact gacgacatgg ttctaca      57

<210> SEQ ID NO 494
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
cgtatcgcct ccctcgcgcc atcagtgacg tatgtacact gacgacatgg ttctaca      57

<210> SEQ ID NO 495
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
cgtatcgcct ccctcgcgcc atcagtgtga gtagtacact gacgacatgg ttctaca      57

<210> SEQ ID NO 496
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
cgtatcgcct ccctcgcgcc atcagacagt atataacact gacgacatgg ttctaca      57

<210> SEQ ID NO 497
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
cgtatcgcct ccctcgcgcc atcagacgcg atcgaacact gacgacatgg ttctaca      57

<210> SEQ ID NO 498
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
cgtatcgcct ccctcgcgcc atcagactag cagtaacact gacgacatgg ttctaca      57

<210> SEQ ID NO 499
```

```
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ctatgcgcct tgccagcccg ctcagacgag tgcgttacgg tagcagagac ttggtct      57

<210> SEQ ID NO 500
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
ctatgcgcct tgccagcccg ctcagacgct cgacatacgg tagcagagac ttggtct      57

<210> SEQ ID NO 501
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
ctatgcgcct tgccagcccg ctcagagacg cactctacgg tagcagagac ttggtct      57

<210> SEQ ID NO 502
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
ctatgcgcct tgccagcccg ctcagtcgat agtgatacgg tagcagagac ttggtct      57

<210> SEQ ID NO 503
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
ctatgcgcct tgccagcccg ctcagatcag acacgtacgg tagcagagac ttggtct      57

<210> SEQ ID NO 504
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
ctatgcgcct tgccagcccg ctcagatatc gcgagtacgg tagcagagac ttggtct      57

<210> SEQ ID NO 505
<211> LENGTH: 57
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
ctatgcgcct tgccagcccg ctcagcgtgt ctctatacgg tagcagagac ttggtct        57

<210> SEQ ID NO 506
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
ctatgcgcct tgccagcccg ctcagctcgc gtgtctacgg tagcagagac ttggtct        57

<210> SEQ ID NO 507
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ctatgcgcct tgccagcccg ctcagtctct atgcgtacgg tagcagagac ttggtct        57

<210> SEQ ID NO 508
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ctatgcgcct tgccagcccg ctcagtgata cgtcttacgg tagcagagac ttggtct        57

<210> SEQ ID NO 509
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
ctatgcgcct tgccagcccg ctcagcatag tagtgtacgg tagcagagac ttggtct        57

<210> SEQ ID NO 510
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
ctatgcgcct tgccagcccg ctcagcgaga gatactacgg tagcagagac ttggtct        57

<210> SEQ ID NO 511
<211> LENGTH: 57
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 511
ctatgcgcct tgccagcccg ctcagatacg acgtatacgg tagcagagac ttggtct    57

<210> SEQ ID NO 512
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
ctatgcgcct tgccagcccg ctcagtcacg tactatacgg tagcagagac ttggtct    57

<210> SEQ ID NO 513
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
ctatgcgcct tgccagcccg ctcagcgtct agtactacgg tagcagagac ttggtct    57

<210> SEQ ID NO 514
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
ctatgcgcct tgccagcccg ctcagtctac gtagctacgg tagcagagac ttggtct    57

<210> SEQ ID NO 515
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
ctatgcgcct tgccagcccg ctcagtgtac tactctacgg tagcagagac ttggtct    57

<210> SEQ ID NO 516
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
ctatgcgcct tgccagcccg ctcagacgac tacagtacgg tagcagagac ttggtct    57

<210> SEQ ID NO 517
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 517
ctatgcgcct tgccagcccg ctcagcgtag actagtacgg tagcagagac ttggtct       57

<210> SEQ ID NO 518
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
ctatgcgcct tgccagcccg ctcagtacga gtatgtacgg tagcagagac ttggtct       57

<210> SEQ ID NO 519
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
ctatgcgcct tgccagcccg ctcagtactc tcgtgtacgg tagcagagac ttggtct       57

<210> SEQ ID NO 520
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ctatgcgcct tgccagcccg ctcagtagag acgagtacgg tagcagagac ttggtct       57

<210> SEQ ID NO 521
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
ctatgcgcct tgccagcccg ctcagtcgtc gctcgtacgg tagcagagac ttggtct       57

<210> SEQ ID NO 522
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ctatgcgcct tgccagcccg ctcagacata cgcgttacgg tagcagagac ttggtct       57

<210> SEQ ID NO 523
<211> LENGTH: 57
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 523
ctatgcgcct tgccagcccg ctcagacgcg agtattacgg tagcagagac ttggtct      57

<210> SEQ ID NO 524
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
ctatgcgcct tgccagcccg ctcagactac tatgttacgg tagcagagac ttggtct      57

<210> SEQ ID NO 525
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ctatgcgcct tgccagcccg ctcagtcgct gcgtatacgg tagcagagac ttggtct      57

<210> SEQ ID NO 526
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
ctatgcgcct tgccagcccg ctcagagact atacttacgg tagcagagac ttggtct      57

<210> SEQ ID NO 527
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
ctatgcgcct tgccagcccg ctcagagcgt cgtcttacgg tagcagagac ttggtct      57

<210> SEQ ID NO 528
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
ctatgcgcct tgccagcccg ctcagagtac gctattacgg tagcagagac ttggtct      57

<210> SEQ ID NO 529
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 529
ctatgcgcct tgccagcccg ctcagataga gtacttacgg tagcagagac ttggtct    57

<210> SEQ ID NO 530
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ctatgcgcct tgccagcccg ctcagcacgc tacgttacgg tagcagagac ttggtct    57

<210> SEQ ID NO 531
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ctatgcgcct tgccagcccg ctcagcagta gacgttacgg tagcagagac ttggtct    57

<210> SEQ ID NO 532
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
ctatgcgcct tgccagcccg ctcagcgacg tgacttacgg tagcagagac ttggtct    57

<210> SEQ ID NO 533
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
ctatgcgcct tgccagcccg ctcagtacac acacttacgg tagcagagac ttggtct    57

<210> SEQ ID NO 534
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ctatgcgcct tgccagcccg ctcagtacac gtgattacgg tagcagagac ttggtct    57

<210> SEQ ID NO 535
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
ctatgcgcct tgccagcccg ctcagtacag atcgttacgg tagcagagac ttggtct    57

<210> SEQ ID NO 536
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
ctatgcgcct tgccagcccg ctcagtacgc tgtcttacgg tagcagagac ttggtct    57

<210> SEQ ID NO 537
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
ctatgcgcct tgccagcccg ctcagtctga cgtcatacgg tagcagagac ttggtct    57

<210> SEQ ID NO 538
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ctatgcgcct tgccagcccg ctcagtcgat cacgttacgg tagcagagac ttggtct    57

<210> SEQ ID NO 539
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ctatgcgcct tgccagcccg ctcagtcgca ctagttacgg tagcagagac ttggtct    57

<210> SEQ ID NO 540
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ctatgcgcct tgccagcccg ctcagtctag cgacttacgg tagcagagac ttggtct    57

<210> SEQ ID NO 541
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
ctatgcgcct tgccagcccg ctcagtctat actattacgg tagcagagac ttggtct    57

<210> SEQ ID NO 542
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
ctatgcgcct tgccagcccg ctcagtgacg tatgttacgg tagcagagac ttggtct    57

<210> SEQ ID NO 543
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ctatgcgcct tgccagcccg ctcagtgtga gtagttacgg tagcagagac ttggtct    57

<210> SEQ ID NO 544
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ctatgcgcct tgccagcccg ctcagacagt atatatacgg tagcagagac ttggtct    57

<210> SEQ ID NO 545
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
ctatgcgcct tgccagcccg ctcagacgcg atcgatacgg tagcagagac ttggtct    57

<210> SEQ ID NO 546
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
ctatgcgcct tgccagcccg ctcagactag cagtatacgg tagcagagac ttggtct    57

<210> SEQ ID NO 547
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 547
acactgacga catggttcta cagtggttgc cctctccagt a    41

<210> SEQ ID NO 548
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 548
acactgacga catggttcta catcattctc caccctgacc tt    42

<210> SEQ ID NO 549
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 549
acactgacga catggttcta caaggccttg ttctcattgc at    42

<210> SEQ ID NO 550
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 550
acactgacga catggttcta cagggtcctt tctcttctaa cagg    44

<210> SEQ ID NO 551
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 551
acactgacga catggttcta cacagagggt gatggtgtgg a    41

<210> SEQ ID NO 552
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552
acactgacga catggttcta catgcttccc attcttcttc tcc    43

<210> SEQ ID NO 553
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553

```
acactgacga catggttcta catgcctctt atcttatcag ctcca                45
```

<210> SEQ ID NO 554
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554

```
acactgacga catggttcta cataagatcc gtggcaagaa cc                   42
```

<210> SEQ ID NO 555
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555

```
acactgacga catggttcta cagtccatgg ccagcttttg                      40
```

<210> SEQ ID NO 556
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556

```
acactgacga catggttcta caagggttcc tgggtctgtg ta                   42
```

<210> SEQ ID NO 557
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557

```
acactgacga catggttcta cacttcttgt tggtgggctc ag                   42
```

<210> SEQ ID NO 558
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558

```
acactgacga catggttcta catgagaggg caaaggtcac tt                   42
```

<210> SEQ ID NO 559
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559

```
acactgacga catggttcta cagttgagat gctgggagag gt                   42
```

<210> SEQ ID NO 560
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
acactgacga catggttcta cagacccgct tctctgaaag g            41

<210> SEQ ID NO 561
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
acactgacga catggttcta cacaggtttc cgcaccaaga             40

<210> SEQ ID NO 562
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
acactgacga catggttcta caaaccttgc taaaggagtg atttct      46

<210> SEQ ID NO 563
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 563
acactgacga catggttcta caacgtctcc acacatcagc ac          42

<210> SEQ ID NO 564
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 564
acactgacga catggttcta caccagagga ggaacgagct aa          42

<210> SEQ ID NO 565
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 565
acactgacga catggttcta cattccatgt ggttatgcca ag          42

<210> SEQ ID NO 566
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 566
acactgacga catggttcta cacaataagc agcagatata aggttgtt                    48

<210> SEQ ID NO 567
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 567
acactgacga catggttcta cattcaaagg tggttttggg ttg                         43

<210> SEQ ID NO 568
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 568
acactgacga catggttcta cattgggaaa catcattctt tgg                         43

<210> SEQ ID NO 569
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 569
acactgacga catggttcta catggtgtca ttgtggctag ttg                         43

<210> SEQ ID NO 570
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
acactgacga catggttcta catgaagttg atgaaacaga tattcctt                    48

<210> SEQ ID NO 571
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 571
acactgacga catggttcta cattggcagc atagcataaa taaca                       45

-continued

<210> SEQ ID NO 572
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 572
acactgacga catggttcta cactgcattt gacattcctt gttt                44

<210> SEQ ID NO 573
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 573
acactgacga catggttcta cagcagacag aatctccaaa gca                 43

<210> SEQ ID NO 574
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 574
acactgacga catggttcta caggttggag atcaagagct tcct                44

<210> SEQ ID NO 575
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 575
acactgacga catggttcta cagaaaccag cccaaaggtg t                   41

<210> SEQ ID NO 576
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 576
acactgacga catggttcta cagaattgtg agaaggaggc tctg                44

<210> SEQ ID NO 577
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 577
acactgacga catggttcta caccttgtcg gagtggctta tc                  42

<210> SEQ ID NO 578

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
acactgacga catggttcta caggagcttt aaggcaggga aa                              42

<210> SEQ ID NO 579
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
acactgacga catggttcta caagcgaggc agacaaatag aag                             43

<210> SEQ ID NO 580
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
acactgacga catggttcta catctgcatt ctggcatgtc tc                              42

<210> SEQ ID NO 581
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
acactgacga catggttcta caaaggtgag ctcttttcct gtctt                           45

<210> SEQ ID NO 582
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
acactgacga catggttcta catgcttctg tgacctcttg tgt                             43

<210> SEQ ID NO 583
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 583
acactgacga catggttcta cacataactc acaacagcct ccttc                           45

<210> SEQ ID NO 584
<211> LENGTH: 40
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
acactgacga catggttcta cagtggtgga actgccagga                    40

<210> SEQ ID NO 585
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
acactgacga catggttcta cacctccctt tcaaactttc tgtg               44

<210> SEQ ID NO 586
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
acactgacga catggttcta catgattatc ttgaagtcac ttgttgaa           48

<210> SEQ ID NO 587
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
acactgacga catggttcta cagtgtcttc ctggagcggt aa                 42

<210> SEQ ID NO 588
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 588
acactgacga catggttcta catctttcct aaagactttc tcctttg            47

<210> SEQ ID NO 589
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 589
acactgacga catggttcta caagtcctgg ggaatgaagg tt                 42

<210> SEQ ID NO 590
<211> LENGTH: 42
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 590
acactgacga catggttcta cagttcctcc tgtcaaccct ga                      42

<210> SEQ ID NO 591
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 591
acactgacga catggttcta catccttatc atcctcgctc ct                      42

<210> SEQ ID NO 592
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 592
acactgacga catggttcta caactccagc cacgacctca t                       41

<210> SEQ ID NO 593
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 593
acactgacga catggttcta caggtccagc ccacaacagt                         40

<210> SEQ ID NO 594
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 594
acactgacga catggttcta catcttccaa agctgggaac tg                      42
```